United States Patent
Head et al.

(10) Patent No.: US 6,197,794 B1
(45) Date of Patent: Mar. 6, 2001

(54) PHENYLALANINE DERIVATIVES

(75) Inventors: John Clifford Head; Sarah Catherine Archibald, both of Maidenhead; Graham John Warrellow, Northwood; John Robert Porter, Chinnor, all of (GB)

(73) Assignee: Celltech Therapeutics Limited (GB)

( * ) Notice: Subject to any disclaimer, the term of this patent is extended or adjusted under 35 U.S.C. 154(b) by 0 days.

(21) Appl. No.: 09/226,833

(22) Filed: Jan. 7, 1999

(30) Foreign Application Priority Data

Jan. 8, 1998 (GB) .................................................. 9800396
Dec. 2, 1998 (GB) .................................................. 9826499

(51) Int. Cl.$^7$ ...................... C07D 401/02; C07D 277/06; A61K 31/44; A61K 38/05

(52) U.S. Cl. ...................... 514/342; 546/269.7; 514/365; 548/200

(58) Field of Search ........................ 546/269.7; 514/342, 514/365; 548/200

(56) References Cited

U.S. PATENT DOCUMENTS

| | | | |
|---|---|---|---|
| 4,470,973 | 9/1984 | Natarajan et al. ..................... | 424/177 |
| 4,554,273 | 11/1985 | Bayssat et al. ....................... | 514/221 |
| 5,510,346 | 4/1996 | Martin et al. ......................... | 514/221 |
| 5,698,691 | 12/1997 | Yukimasa et al. .................... | 540/490 |
| 6,093,696 | 7/2000 | Head et al. ............................ | 514/19 |

FOREIGN PATENT DOCUMENTS

| | | |
|---|---|---|
| 28 37 264 A1 | 3/1979 | (DE) . |
| 0 288 176 | 10/1988 | (EP) . |
| 0 710 657 A1 | 5/1996 | (EP) . |
| 56 090045 | 7/1981 | (JP) . |
| WO 93/00095 | 1/1993 | (WO) . |
| WO 93/08174 | 4/1993 | (WO) . |
| WO 95/19356 | 7/1995 | (WO) . |
| WO 96/26190 | 8/1996 | (WO) . |
| WO 97/08145 | 3/1997 | (WO) . |
| WO 98/00395 | 1/1998 | (WO) . |
| WO 98/54207 | 12/1998 | (WO) . |
| WO 99/37618 | 7/1999 | (WO) . |
| WO 99/43642 | 9/1999 | (WO) . |
| WO 99/48879 | 9/1999 | (WO) . |

OTHER PUBLICATIONS

Clausen, K., et al., "Studies on amino acids and peptides. II. Synthesis of protected endothiodipeptides," *J. Chem. Scr.,* 1982, 20(1–2), 14–18, doc. No. 97:163474 (abstract only, 1 page).

Frank, R., et al., "Extremely mild reagent for Boc deprotection," *J. Chem. Commun.* (Cambridge), 1996, 22, 2509–2510, doc. No. 126:104395 (abstract only, 3 pages).

Kobayashi, A., et al., "Syntheses of 2–dialkylamino–4, 4–disubstituted 5 (4H)–thiazolones," *J. Yakugaku Zasshi,* 1970, 90(11), 1377–1380, doc. No. 74:31713 (abstract only, 3 pages).

Koenig, H.B., et al., ".beta–Lactam antibiotics," *Ger. Offen.,* 41 pages, doc. No. 83:97276 (abstract only, 5 pages), 1975.

Masuda, T., *Jpn. Kodai Tokkyo Koho,* 22 pages, doc. No. 115:280022 (abstract only, 1page), 1991.

Pfeifer, T., et al., "Specific fragmentation of thioxo peptides facilitates the assignment of the thioxylated amino acid," *J. Mass Spectrom,* 1997, 32(10), 1064–1071, doc. No. 127:331738 (abstract only 2 pages).

Sawa, N., et al., "Preparation of 4(5)–thiocarbamoylimoylimidazole compounds," *Jpn. Kokai Tokkyo Koho,* 33 pages, doc. No. 115:183296 (abstract only, 2 pages), 1991.

Schutkowski, M., et al., "Inhibition of peptidyl–prolyl cis/trans isomerase activity by substrate analog structures: thioxo tetrapeptide–4–nitroanilides," *Biochemistry,* 1995, 34(40), 13016–13026, doc. No. 123:221511 (abstract only, 4 pages).

(List continued on next page.)

*Primary Examiner*—Zinna Northington Davis
(74) *Attorney, Agent, or Firm*—Woodcock Washburn Kurtz Mackiewicz & Norris LLP

(57) ABSTRACT

Phenylalanine derivatives of formula (1) are described:

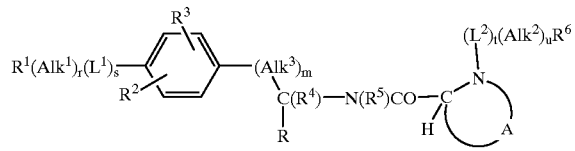

(1)

in which
$L^1$ is a linker atom or group;
A is a chain —[C(R$^7$)(R$^8$)]$_p$Y[C(R$^9$)(R$^{10}$)]$_q$— in which Y is a sulphur atom or a —S(O)— or —S(O)$_2$— group, R$^7$, R$^8$, R$^9$ and R$^{10}$, which may be the same or different, is each a hydrogen atom or a straight or branched alkyl or optionally substituted aromatic group, or R$^7$ and R$^8$ together with the carbon atom to which they are attached, or R$^9$ and R$^{10}$ together with the carbon atom to which they are attached, each forms a C$_{3-7}$cycloalkyl group, and p and q, which may be the same or different, is each zero or an integer 1 or 2, provided that when one of p or q is zero the other is an integer 1 or 2;
$L^2$ is a linker group selected from —C(O)—, —C(O)O—, —C(S)—, —S(O)$_2$—, —CON(R$^{11}$)—, [where R$^{11}$ is a hydrogen atom or a straight or branched alkyl group], —CSN(R$^{11}$)—, —SON(R$^{11}$)— or SO$_2$N(R$^{11}$)—;
R is a carboxylic acid or a derivative thereof;
and the salts, solvates and hydrates thereof.

The compounds are able to inhibit the binding of α$_4$ integrins to their ligands and are of use in the prophylaxis and treatment of immune or inflammatory disorders.

24 Claims, No Drawings

OTHER PUBLICATIONS

"Cephalosporins," *Jpn. Kokai Tokkyo Koho*, 40 pages, doc. No. 99:5433 (abstract only, 2 pages), 1982.

Buckle, D.R., et al., "Non Thiazolidinedione Antihyperglycaemic Agents. 1: α–Heteroatom Substituted β–Phenylpropanoic Acids," *Bioorg. Med. Chem. Lett.*, 1996, 6(17), 2121–2126.

Keenan, R.M. et al., "Discovery of Potent Nonpeptide Vitronectin Receptor (avβ$_3$) Antagonists," *J. Med. Chem.*, 1997, 40(15), 2289–2292.

McDowell, R.S. et al., "From Peptide to Non–Peptide. 2. The *de Novo* Design of Potent, Non–Peptidal Inhibitors of Platelet Aggregation Based on a Benzodiazepinedione Scaffold," *J. Am. Chem. Soc.*, 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.*, 1996, 6(21), 2481–2486.

Ukai, Y. et al., "A novel synthetic inhibitor of endopeptidase–24;15," *Chemical Abstracts*, 1997, 127(2), 1 page.

Venturella, V.S. et al., "Substituted 1,3–Dihydro–4H–furo [3,4–d]–1,3–benzodiazepin–3–ones: Synthesis and Scope of the Method," *J. Heterocyclic Chem.*, 1969, 6(5), 671–679.

Wojciechowska, H. et al., "Preparation of 2,4–dinitrophenyl derivatives of tyrosine," *Chemical Abstracts*, 1968, 68(25), Abstract No. 114926r, 1 page.

Lobb, R.R., et al., "Small molecule antagonists of alpha4 integrins: novel drugs for asthma," *Exp. Opin, Invest. Drugs*, 1999, XP000885957, 8(7), 935–945.

Samanen, J., et al., "Vascular indications for integrin alpha V antagonists," *Current Pharm. Design.*, 1997, 3, 545–584.

Šavrda, J., "CIS–TRANS isomerism of N–ACYL derivatives of proline and its analogues, linear peptides with CIS peptide bonds,"*Proc. 14$^{th}$ European Peptide Symposium*, Loffet, A. (ed.), 1976, 653–656.

Azzouny, A.E., et al., "Synthesis of some N–substituted salicylamides structurally related to certain antimicrobials," *Pharmazie*, 1977, 32(6), 318–323 (abstract).

Badshah, A., et al., "Catalytic reduction of azlactones in alkaline media. Synthesis of amino acids," *J. of Organic Chemistry*, 1972, 37(18), 2916–2918.

Tous, G., et al., "O'–(Epoxyalkyl) tyrosines and (Epoxyalkyl) phenylalanine as irreversible inactivators of serine proteases: synthesis and inhibition mechanism," *J. of Medicinal Chemistry*, 1990, 33(6), 1620–1634.

PHENYLALANINE DERIVATIVES

This invention relates to a series of phenylalanine derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T. A. Nature, 346. 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus the integrin termed α4β1 consists of the integrin alpha 4 chain associated with the integrin beta 1 chain, but is also widely referred to as Very Late Antigen 4 or VLA4. Not all of the potential pairings of integrin alpha and beta chains have yet been observed in nature and the integrin family has been subdivided into a number of subgroups based on the pairings that have been recognised [Sonnenberg, A. ibid].

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al Am. J. Physiol. 263, L723, (1992); Binns, R. M. et al J. Immunol. 157, 4094, (1996)]. A number of monoclonal antibodies which block adhesion molecule function are currently being investigated for their therapeutic potential in human disease.

One particular integrin subgroup of interest involves the α4 chain which can pair with two different beta chains α1 and β7 [Sonnenberg, A. ibid]. The α4β1 pairing occurs on many circulating leukocytes (for example lymphocytes, monocytes and eosinophils) although it is absent or only present at low levels on circulating neutrophils. α4β1 binds to an adhesion molecule (Vascular Cell Adhesion Molecule-1 also known as VCAM-1) frequently up-regulated on endothelial cells at sites of inflammation [Osborne, L. Cell, 62, 3, (1990)]. The molecule has also been shown to bind to at least three sites in the matrix molecule fibronectin [Humphries, M. J. et at. Ciba Foundation Symposium, 189, 177, (1995)]. Based on data obtained with monoclonal antibodies in animal models it is believed that the interaction between (α4β1 and ligands on other cells and the extracellular matrix plays an important role in leukocyte migration and activation [Yednock, T. A. et al, Nature, 356, 63, (1992); Podolsky, D. K. et al. J. Clin. Invest. 92, 373, (1993); Abraham, W. M. et al. J. Clin. Invest. 93, 776, (1994)].

The integrin generated by the pairing of α4 and β37 has been termed LPAM-1 [Holzmann, B and Weissman, I. EMBO J. 8, 1735, (1989)] and like α4β1, binds to VCAM-1 and fibronectin. In addition, α4β7 binds to an adhesion molecule believed to be involved in the homing of leukocytes to mucosal tissue termed MAdCAM-1 [Berlin, C. et al, Cell, 74, 185, (1993)]. The interaction between α4β7 and MAdCAM-1 may also be important at sites of inflammation outside of mucosal tissue [Yang, X-D. et al, PNAS, 91, 12604 (1994)].

Regions of the peptide sequence recognised by α4β1 and α4β7 when they bind to their ligands have been identified. α4β1 seems to recognise LDV, IDA or REDV peptide sequences in fibronectin and a QIDSP sequence in VCAM-1 [Humphries, M. J. et al, ibid] whilst α4β7 recognises a LDT sequence in MAdCAM-1 [Briskin, M. J. et al, J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6, 2495, (1996); Vanderslice, P. J. Immunol. 158, 1710, (1997)]. It has also been reported that a short peptide sequence derived from the α4β1 binding site in fibronectin can inhibit a contact hypersensitivity reaction in a trinitrochlorobenzene sensitised mouse [Ferguson, T. A. et al, PNAS 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is very important to be able to identify selective inhibitors of the alpha 4 subgroup.

We have now found a group of compounds which are potent and selective inhibitors of α4 integrins. Members of the group are able to inhibit α4 integrins such as α4β1 and/or α4β7 at concentrations at which they generally have no or minimal inhibitory action on ax integrins of other subgroups. The compounds are thus of use in medicine, for example in the prophylaxis and treatment of immune or inflammatory disorders as described hereinafter.

Thus according to one aspect of the invention we provide a compound of formula (1):

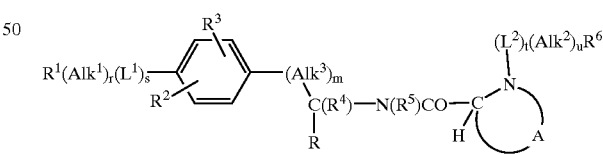

(1)

wherein

R$^1$ is a hydrogen atom or an optionally substituted cycloaliphatic, polycycloaliphatic, heterocycloaliphatic, polyheterocycloaliphatic, aromatic or heteroaromatic group;

Alk$^1$ and Alk$^2$, which may be the same or different, is each an optionally substituted aliphatic or heteroaliphatic chain;

L$^1$ is a linker atom or group;

r, s, t and u is each zero or an integer 1;

Alk$^3$ is a straight or branched alkylene chain;

m is zero or an integer 1;
$R^4$ is a hydrogen atom or a methyl group;
$R^5$ is a hydrogen atom or a straight or branched alkyl group;
A is a chain —$[C(R^7)(R^8)]_p Y[C(R^9)(R^{10})]_q$— in which Y is a sulphur atom or a —S(O)— or —S(O)$_2$— group, $R^7$, $R^8$, $R^9$ and $R^{10}$, which may be the same or different, is each a hydrogen atom or a straight or branched alkyl or optionally substituted aromatic group, or $R^7$ and $R^8$ together with the carbon atom to which they are attached, or $R^9$ and $R^{10}$ together with the carbon atom to which they are attached, each forms a $C_{3-7}$cycloalkyl group, and p and q, which may be the same or different, is each zero or an integer 1 or 2, provided that when one of p or q is zero the other is an integer 1 or 2;
$L^2$ is a linker group selected from —C(O)—, —C(O)O—, —C(S)—, —S(O)$_2$—, —CON($R^{11}$)—, [where $R^{11}$ is a hydrogen atom or a straight or branched alkyl group], —CSN($R^{11}$)—, —SON($R^{11}$)— or SO$_2$N($R^{11}$)—;
$R^2$ and $R^3$, which may be the same or different is each an atom or group —$L^3(CH_2)_p L^4(R^{2a})_q$ in which $L^3$ and $L^4$ is each a covalent bond or a linker atom or group, p is zero or the integer 1, q is an integer 1, 2 or 3 and $R^{2a}$ is a hydrogen or halogen atom or a group selected from straight or branched alkyl, —OR$^{12}$ [where $R^{12}$ is a hydrogen atom or an optionally substituted straight or branched alkyl group], —SR$^{12}$, —NR$^{12}$R$^{13}$, [where $R^{13}$ is as just defined for $R^{12}$ and may be the same or different], —NO$_2$, —CN, —CO$_2$R$^{12}$, —SO$_3$H, —SO$_2$R$^{12}$, —OCO$_2$R$^{12}$, —CONR$^{12}$R$^{13}$, —OCONR$^{12}$R$^{13}$, —CSNR$^{12}$R$^{13}$, —COR$^{12}$, —N(R$^{12}$)COR$^{13}$, N(R$^{12}$)CS$^{13}$, —SO$_2$N(R$^{12}$)(R$^{13}$), —N(R$^{12}$)SO$_2$R$^{13}$, —N(R$^{12}$)CONR$^{13}$R$^{14}$ [where $R^{14}$ is a hydrogen atom or an optionally substituted straight or branched alkyl group], —N(R$^{12}$)CSNR$^{13}$R$^{14}$ or —N(R$^{12}$)SO$_2$NR$^{13}$R$^{14}$;
R is a carboxylic acid or a derivative thereof;
$R^6$ is a hydrogen atom or an optionally substituted cycloaliphatic, polycycloaliphatic, heterocycloaliphatic, polyheterocycloaliphatic, aromatic or heteroaromatic group, provided that:
(1) when $R^1(Alk^1)_r(L^1)_s$— is $R^1(Alk^1)_r$O—, $R^1(Alk^1)_r$C(O)O—, $R^1(Alk^1)_r$NHC(O)O— or $R^1(Alk^1)_r$S(O)$_2$O—, [in which $R^1$ is a hydrogen atom or an optionally substituted aromatic group and Alk$^1$ is an optionally substituted alkyl group] and $R^6(Alk^2)_u(L^2)_t$— is $R^6(Alk^2)_u$CO—, $R^6(Alk^2)_u$C(O)O—, $R^6(Alk^2)_u$NHCO— or $R^6(Alk^2)_u$S(O)$_2$— [in which Alk$^2$ is an optionally substituted alkyl chain], then $R^6$ is an optionally substituted cycloaliphatic, polycycloaliphatic, heterocycloaliphatic or heteroaromatic group; and
(2) Alk$^2$, when present is not a —(CH$_2$)$_n$S—, —(CH$_2$)$_n$SS— or —(CH$_2$)$_n$SC(O)— chain, where n is an integer 1, 2 or 3;
and the salts, solvates and hydrates thereof.

It will be appreciated that compounds of formula (1) may have one or more chiral centres. Where one or more chiral centres is present, enantiomers or diastereomers may exist, and the invention is to be understood to extend to all such enantiomers, diasteromers and mixtures thereof, including racemates. Formula (1) and the formulae hereinafter are intended to represent all individual isomers and mixtures thereof, unless stated or shown otherwise.

In the compounds of formula (1), derivatives of the carboxylic acid group R include carboxylic acid esters and amides. Particular esters and amides include —CO$_2$R$^{12}$ and CONR$^{12}$R$^{13}$ groups as described herein.

Alk$^3$ in the compounds of the invention may be for example a straight or branched $C_{1-3}$alkylene chain. Particular examples include —CH$_2$—, —CH(CH$_3$)— and —(CH$_2$)$_2$—.

When each of $R^{2a}$, $R^5$, $R^7$, $R^8$, $R^9$, $R^{10}$, $R^{11}$, $R^{12}$, $R^{13}$ and/or $R^{14}$ in the compounds of formula (1) is a straight or branched alkyl group it may be a straight or branched $C_{1-6}$alkyl group, e.g. a $C_{1-3}$alkyl group such as a methyl or ethyl group. When the $R^{12}$, $R^{13}$ and/or $R^{14}$ group is optionally substituted, the substituent may be selected for example from one, two, three or more of the optional substituents described below in relation to the aliphatic groups represented by Alk$^1$.

When in the compounds of the invention $L^1$, $L^3$ and/or $L^4$ is present as a linker atom or group it may be any divalent linking atom or group. Particular examples include —O— or —S— atoms or —C(O)—, —C(O)O—, —C(S)—, —S(O)—, —S(O)$_2$—, —N(R$^{11}$)— [where $R^{11}$ is as defined previously], —CON(R$^{11}$)—, —OC(O)N(R$^{11}$)—, —CSN(R$^{11}$)—, —N(R$^{11}$)CO—, —N(R$^{11}$)C(O)O—, —N(R$^{11}$)CS—, —S(O)N(R$^{11}$)—, —S(O)$_2$N(R$^{11}$)—, —N(R$^{11}$)S(O)—, —N(R$^{11}$)S(O)$_2$—, —N(R$^{11}$)CON(R$^{11}$), —N(R$^{11}$)CSN(R$^{11}$), —N(R$^{11}$)SON(R$^{11}$)— or —N(R$^{11}$)SO$_2$N(R$^{11}$)— groups. Where the linker group contains two $R^{11}$ substituents, these may be the same or different.

When Alk$^1$ and/or Alk$^2$ compounds of formula (1) is an optionally substituted aliphatic chain it may be an optionally substituted $C_{1-10}$ aliphatic chain. Particular examples include optionally substituted straight or branched chain $C_{1-6}$ alkyl, $C_{2-6}$ alkenyl, or $C_{2-6}$ alkynyl chains.

Heteroaliphatic chains represented by Alk$^1$ or Alk$^2$ include the aliphatic chains just described but with each chain additionally containing one, two, three or four heteroatoms or heteroatom-containing groups. Particular heteroatoms or groups include atoms or groups $L^5$ where $L^5$ is as defined above for $L^1$ when $L^1$ is a linker atom or group. Each $L^5$ atom or group may interrupt the aliphatic chain, or may be positioned at its terminal carbon atom to connect the chain to the atom or group $R^1$ or $R^6$.

Particular examples of aliphatic chains represented by Alk$^1$ or Alk$^2$ include optionally substituted —CH$_2$—, —CH$_2$CH$_2$—, —(CH$_2$)$_2$CH$_2$—, —CH(CH$_3$)CH$_2$—, —(CH$_2$)$_3$CH$_2$—, —CH(CH$_3$)CH$_2$CH$_2$—, —CH$_2$CH(CH$_3$)CH$_2$—, —C(CH$_3$)$_2$CH$_2$—, —(CH$_2$)$_4$CH$_2$—, —(CH$_2$)$_5$CH$_2$—, —CHCH—, —CHCHCH$_2$—, —CH$_2$CHCH—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$—, or —(CH$_2$)$_2$CC— chains. Where appropriate each of said chains may be optionally interrupted by one or two atoms and/or groups $L^5$ to form an optionally substituted heteroaliphatic chain. Particular examples include optionally substituted —L$^5$CH$_2$—, —CH$_2$L$^5$CH$_2$—, —L$^5$(CH$_2$)$_2$—, —CH$_2$L$^5$(CH$_2$)$_2$—, —(CH$_2$)$_2$L$^5$CH$_2$—, —L$^5$(CH$_2$)$_3$— and —(CH$_2$)$_2$L$^5$(CH$_2$)$_2$— chains.

When $R^1$ and/or $R^6$ is present in compounds of formula (1) as an optionally substituted cycloaliphatic group it may be an optionally substituted $C_{3-10}$ cycloaliphatic group. Particular examples include optionally substituted $C_{3-10}$ocycloalkyl, e.g. $C_{3-7}$cycloalkyl, $C_{3-10}$ cycloalkenyl e.g. $C_{3-7}$cycloalkenyl or $C_{3-10}$ocycloalkynyl e.g. $C_{3-7}$cycloalkynyl groups.

Optionally substituted heterocycloaliphatic groups represented by $R^1$ or $R^6$ include the optionally substituted cycloaliphatic groups just described for $R^1$ and $R^6$ but with each group additionally containing one, two, three or four heteroatoms or heteroatom-containing groups $L^3$ as just defined.

Optionally substituted polycycloaliphatic groups represented by $R^1$ and/or $R^6$ include optionally substitued $C_{7-10}$ bi- or tricycloalkyl or $C_7l_{10}$bi- or tricycloalkenyl groups.

Optionally substituted polyheterocycloaliphatic groups represented by $R^1$ and/or $R^6$ include the optionally substituted polycycloalkyl groups just described, but with each group additionally containing one, two, three or four $L^3$ atoms or groups.

Particular examples of $R^1$ or $R^6$ cycloaliphatic, polycycloaliphatic, heterocycloaliphatic and polyheterocycloaliphatic groups include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, 2,4-cyclopentadien-1-yl, 3,5,-cyclohexadien-1-yl, adamantyl, norbornyl, norbornenyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,2-oxadiazinyl groups.

The optional substituents which may be present on the $Alk^1$, $Alk^2$, $R^1$ or $R^6$ aliphatic heteroaliphatic, cycloaliphatic, polycycloaliphatic or heterocycloaliphatic or polyheterocycloaliphatic groups include one, two, three or more substituents selected from halogen atoms, e.g. fluorine, chlorine, bromine or iodine atoms, or hydroxyl, $C_{1-6}$alkoxy, e.g. methoxy or ethoxy, thiol, $C_{1-6}$alkylthio e.g. methylthio or ethylthio, amino or substituted amino groups. Substituted amino groups include $-NHR^{11}$ and $-N(R^{11})_2$ groups where $R^{11}$ is as defined above.

In the compounds of formula (1), optionally substituted aromatic groups represented by the group $R^1$ and/or $R^6$ include for example optionally substituted monocyclic or bicyclic fused ring $C_{6-12}$ aromatic groups, such as optionally substituted phenyl, 1- or 2-naphthyl, 1- or 2-tetrahydronaphthyl, indanyl or indenyl groups.

Optionally substituted aromatic groups represented by the group $R^1$ or $R^6$ in compounds of formula (1) include for example optionally substituted monocyclic or bicyclic fused ring $C_{6-12}$ aromatic groups, such as optionally substituted phenyl, 1 - or 2-naphthyl, 1 - or 2-tetrahydronaphthyl, indanyl or indenyl groups.

Optionally substituted heteroaromatic groups, represented by the group $R^1$ or $R^6$ in compounds of formula (1) include for example optionally substituted $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered fused-ring heteroaromatic groups containing one, two or more heteroatoms selected from oxygen, sulphur or nitrogen atoms.

Particular examples of heteroaromatic groups of these types include optionally substituted pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, isobenzofuryl, benzothienyl, benzoriazolyl, isobenzothienyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on aromatic or heteroaromatic groups of the above types include one, two, three or more substituents selected from the group $-L^3(CH_2)_p L^4(R^{2a})_q$ where $L^3$, $L^4$, p and q are as defined previously and $R^{2a}$ is as previously defined but is other than an hydrogen atom when $L^3$ and $L^4$ is each a covalent bond and p is zero.

Examples of the substituents represented by $R^2$ and $R^3$ in compounds of formula (1) and which may be present on aromatic or heteroaromatic groups represented by $R^1$ and $R^6$ include atoms or groups $-L^3(CH_2)_p L^4 R^{2a}$, $-L^3(CH_2)_p R^{2a}$, $-L^3 R^{2a}$, $-(CH_2)_p R^{2a}$ and $-R^{2a}$ wherein $L^3$, $(CH_2)_p$, $L^4$ and $R^{2a}$ are as defined above. Particular examples of such substituents include $-L^3 CH_2 L^3 R^{2a}$, $-L^3 CH(CH_3) L^4 R^{2a}$, $-L^3 CH(CH_2)_2 L^4 R^{2a}$, $-L^3 CH_2 R^{2a}$, $-L^3 CH(CH_3) R^{2a}$, $-L^3(CH_2)_2 R^{2a}$, $-CH_2 R^{2a}$, $-CH(CH_3) R^{2a}$ and $-(CH_2)_2 R^{2a}$ groups.

Thus each of $R^2$ and $R^3$ and, where present, substituents on $R^1$ and $R^6$ aromatic or heteroaromatic groups in compounds of the invention may be for example selected from a hydrogen atom, a halogen atom, e.g. a fluorine, chlorine, bromine or iodine atom, or a $C_{1-6}$alkyl, e.g. methyl, ethyl, n-propyl, i-propyl, n-butyl or t-butyl, $C_{1-6}$alkylamino, e.g. methylamino or ethylamino, $C_{1-6}$hydroxyalkyl, e.g. hydroxymethyl, hydroxyethyl or $-C(OH)(CF_3)_2$, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, halo$C_{1-6}$alkyl, e.g. $-CF_3$, $CCl_3$, $-CHF_2$, $-CHCl_2$, $-CH_2F$, $-CH_2Cl$, halo$C_{1-6}$alkoxy, e.g. $-OCF_3$, $-OCCl_3$, $-OCHF_2$, $-OCHCl_2$, $-OCH_2F$, $-OCH_2Cl$, $C_{1-6}$alkyl-amino, e.g. methylamino or ethylamino, amino ($-NH_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, isopropylaminoethoxy, or dimethylaminopropoxy, nitro, cyano, amidino, hydroxyl ($-OH$), formyl [HC(O)—], carboxyl ($-CO_2H$), $-CO_2R^{12}$, $C_{1-6}$ alkanoyl e.g. acetyl, thiol ($-SH$), thio$C_{1-6}$alkyl, e.g. thiomethyl or thioethyl, sulphonyl ($-SO_3H$), $C_{1-6}$alkylsulphonyl, e.g. methylsulphonyl, aminosulphonyl ($-SO_2NH_2$), $C_{1-6}$alkylaminosulphonyl, e.g. methylaminosulphonyl or ethylamino-sulphonyl, $C_{1-6}$dialkylaminosulphonyl, e.g. dimethylaminosulphonyl or diethylaminosulphonyl, phenylaminosulphonyl, carboxamido ($-CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino ($-NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkyamino, e.g. acetamidoethylamino, $C_{1-6}$alkoxycarbonylamino, e.g. methoxycarbonylamino, ethoxycarbonylamino or t-butoxycarbonylamino group.

In one group of compounds of the invention $R^2$ and $R^3$ may each be a hydrogen or halogen atom or a straight or branched alkyl, haloalkyl, alkoxy, haloalkoxy, hydroxyl or nitro group as defined herein.

The chain represented by A in compounds of the invention may for example be a chain $-Y[C(R^9)(R^{11})]_2-$, $-[C(R^7)(R^8)]Y[C(R^9)(R^{10})]-$, $-[C(R^7)(R^8)]_2Y-$, $-[C(R^7)(R^8)]_2Y[C(R^9)(R^{10})]-$ or $-[C(R)^7(R)^8]Y[C(R^9)(R^{10})]_2-$ where Y, $R^7$, $R^8$, $R^9$ and $R^{10}$ are as described above for compounds of formula (1). Particular examples of such chains include $-Y(CH_2)_2-$, $-(CH_2)_2Y-$, $-CH_2YCH_2-$, $-[C(R^7)(R^8)]YCH_2-$ e.g. $-C(CH_3)_2YCH_2-$ and $-CH_2Y[C(R^9)(R^{10})]-$ e.g. $-CH_2YC(CH_3)_2-$ chains.

When in the chain represented by A, $R^7$, $R^8$, $R^9$ and/or $R^{10}$ is an optionally substituted aromatic group it may be an optionally substituted phenyl group. Particular examples of optional substituents include one, two or three substituents selected from halogen atoms, e.g. fluorine, bromine, chlorine or iodine atoms or $C_{1-6}$alkyl, e.g. methyl or ethyl, $C_{1-6}$alkoxy, e.g. methoxy or ethoxy, hydroxy, nitro or cyano groups. When one of $R^7$, $R^8$, $R^9$ or $R^{10}$ is an optionally substituted aromatic group, the remainder for example may each be a hydrogen atom or a straight or branched alkyl group as defined herein.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

R in compounds of the invention is preferably a $-CO_2H$ group.

$Alk^3$ in compounds of formula (1) is preferably a $-CH_2-$ chain and m is preferably an integer 1. In compounds of this type, the carbon atom to which $Alk^3$ and R are attached forms a chiral centre and is preferably in the L configuration.

$R^4$ and $R^5$ in compounds of the invention is each preferably a hydrogen atom.

One particular class of compounds of the invention is that wherein each of $R^7$, $R^8$, $R^9$ and $R^{10}$ in the chain A is as defined for formula (1) other than an optionally substituted aromatic group. In general in compounds of formula (1) the chain A is one in which Y is preferably a sulphur atom. Particularly useful chains represented by A include $-C(R^7)(R^8)SC(R^9)(R^{10})-$ chains, especially $-CH_2SCH_2-$, $-CH(CH_3)SCH_2-$, $-C(CH_3)_2SCH_2-$, $-CH_2SCH(CH_3)-$ and $-CH_2SC(CH_3)_2-$ chains. Compounds of the invention in which A is $-CH_2SCH_2-$ are particularly preferred.

When the linker group $L^1$ is present in compounds of the invention [i.e. when s is an integer 1] it is preferably an oxygen atom or a $-C(O)O-$, $-C(O)NH-$, $-C(O)N(CH_3)-$, $-C(S)NH-$, $-NH-$, $-N(CH_3)-$, $-NHC(O)O-$, $-SO_2-$, $-SO_2NH-$, $-SO_2N(CH_3)-$, $-OC(O)NH-$, $-NHC(O)NH-$ or $-NHC(S)NH-$ group. Especially useful $L^1$ groups include $-SO_2NH-$, $-C(O)O-$, $-NH-$ and, in particular, $-CONH-$.

The aliphatic chain represented by $Alk^1$ in compounds of formula (1) is preferably a $-CH_2-$ chain.

In general in compounds of the invention the group $R^1$ is preferably an optionally substituted aromatic or heteroaromatic group. Particularly useful groups of these types include optionally substituted six-membered monocyclic groups, especially optionally substitued phenyl, pyridyl or pyrimidinyl groups.

Compounds of the invention in which a linker group $L^2$ is present (i.e. when t is an integer 1) are preferred. Compounds of this type in which $L^2$ is a $-C(O)-$ group are particularly useful.

$Alk^2$ in compounds of formula (1) is preferably present (i.e. u is preferably an integer 1) and in particular is a $-CH_2-$ chain. Compounds of this type in which $R^6$ is a hydrogen atom or an optionally substituted aromatic or heteroaromatic group, especially an optionally substituted phenyl, pyridyl or imidazolyl group are particularly preferred.

A particularly useful class of compounds according to the invention has the formula (1) in which $R^1(Alk^1)_r(L^1)_s-$ is a $R^1CH_2L^1$ or $R^1L^1$ group where $R^1$ is an optionally substituted aromatic or heteroaromatic group and $L^1$ is a linker atom or group, $Alk^3$ is a $-CH_2-$ chain, m is an integer 1, $R^4$ is a hydrogen atom, $R^5$ is a hydrogen atom and $-(L^2)_t(Alk^2)_uR^6$ is preferably a $-L^2CH_2R^6$ group where $R^6$ is a hydrogen atom or an optionally substituted aromatic or heteroaromatic group and is especially a $-C(O)CH_2R^6$ group where $R^6$ is as just defined. A particular group of compounds in this class include compounds in which $R^6$ is an optionally substituted heteroaromatic group, particularly an optionally substituted pyridyl group. In general in compounds in this class $R^1CH_2L^1$ is preferably a $R^1CH_2S$, $R^1CH_2S(O)$—, $R^1CH_2S(O)_2$, $R^1CH_2C(O)$, $R^1CH_2N(R^{11})$— or, especially, a $R^1CH_2O$— group; and $R^1L^1$ is preferably a $R^1CSN(R^{11})$—, $R^1N(R^{11})CO$—, $R^1N(R^{11})CS$—, $R^1S(O)N(R^{11})$—, $R^1S(O)_2N(R^{11})$—, $R^1N(R^{11})SO$—, $R^1N(R^{11})S(O)_2$— or, especially, a $R^1CON(R^{11})$— group, particularly a $R^1CONH$— group.

In the compounds of the just mentioned class R is especially a —$CO_2H$ group.

An especially useful group of compounds according to the invention has the formula (1a):

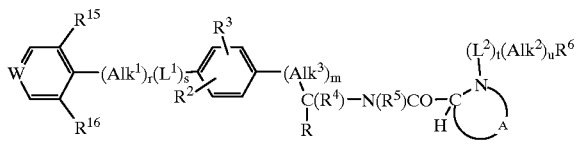

(1a)

wherein —W= is —CH= or —N=; $R^{15}$ and $R^{16}$, which may be the same or different, is each an atom or group —$L^3(CH_2)_pL^4(R^{2a})_q$ as defined for $R^2$ and $R^3$ in formula (1): $Alk^1$, r, $L^1$, s, $R^2$, $R^3$, $Alk^3$, m, R, $R^4$, $R^5$, A, $L^2$, t, $Alk^2$, u and $R^6$ are as defined generally and particularly for formula (1); and the salts, solvates, hydrates and N-oxides thereof.

It will be appreciated that the various preferences stated above in relation to groups present in compounds of formula (1) apply equally to the same groups when present in compounds of formula (1a).

Additionally, in the compounds of formula (1a) the group $(Alk^1)_r(L^1)s$ is preferably a —$SO_2NH$—, —$C(O)O$—, —NH— or, especially a —CONH— group.

One of $R^{15}$ or $R^{16}$ in compounds of formula (1a) may be a hydrogen atom and the other a substituent —$L^3(CH_2)_pL^4(R^{2a})_q$ in which $R^{2a}$ is not a hydrogen atom when $L^3$ and $L^4$ is each a covalent bond and p is zero, but preferably each of $R^{15}$ and $R^{16}$ is a substituent —$L^3(CH_2)_pL^4(R^{2a})_q$ as just defined. Particularly useful $R^{15}$ or $R^{16}$ substituents include halogen atoms, especially fluorine or chlorine atoms, methyl, ethyl, methoxy, ethoxy, —$CF_3$, —OH, —CN, —$NO_2$, —$NH_2$, —$NHCH_3$, —$N(CH_3)_2$, —$COCH_3$, —$SCH_3$, —$CO_2H$ or —$CO_2CH_3$ groups.

—W= in compounds of formula (1a) is preferably —N=.

Particularly useful compounds according to the invention include the following:
N-(Pyrid-3-ylacetyl)-D-thioproline-(N-2,6-dichlorobenzoyl)-L-4-aminophenylalanine;
N-Acetyl-D-thioproline-(N-3,5-dichloroisonicotinoyl)-L-4-amino phenylalanine;
N-(Pyrid-3-ylacetyl)-D-thioproline-O-(2,4,6-trichlorobenzyl)-L-tyrosine;
N-(Pyrid-3-ylacetyl)-D-thioproline-(O-2,4,6-trichlorobenzoyl)-L-tyrosine;
N-(Pyrid-3-ylacetyl)-D-thioproline-(O-2,6-dichlorobenzoyl)-L-tyrosine;
N-Acetyl-D-thioproline-(N'-2,6-dichlorobenzoyl)-L-4-aminophenylalanine;
N-Acetyl-D-thioproline-[N'-2-fluoro-6-(trifluoromethyl)benzoyl]-L-4-aminophenylalanine;
N-Acetyl-D-thioproline-(N'-2,4,6-trichlorobenzoyl)-L-4-aminophenylalanine;
N-Acetyl-D-thioproline-(N'-2,6-trichlorobenzyl)-L-4-aminophenylalanine; and the salts, solvates, hydrates and N-oxides thereof.

It will be appreciated that where appropriate the provisos applying to compounds of general formula (1) apply equally to the above-mentioned specific classes of compounds of formula (1).

Compounds according to the invention are potent and selective inhibitors of α4 integrins. The ability of the compounds to act in this way may be simply determined by employing tests such as those described in the Examples hereinafter.

The compounds are of use in modulating cell adhesion and in particular are of use in the prophylaxis and treatment of diseases or disorders involving inflammation in which the extravasation of leukocytes plays a role. Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $R^1$–$R^6$, $L^1$, $L^2$, $Alk^1$, $Alk^2$, $Alk^3$, m, r, s, t, u and A when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) may be obtained by hydrolysis of an ester of formula (2):

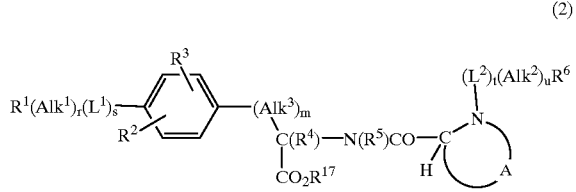

(2)

where $R^{17}$ is an alkyl group.

The hydrolysis may be performed using either an acid or a base depending on the nature of $R^{12}$, for example an organic acid such as trifluoroacetic acid or an inorganic base such as lithium hydroxide or potassium carbonate optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

Esters of formula (2) may be prepared by coupling an amine of formula (3):

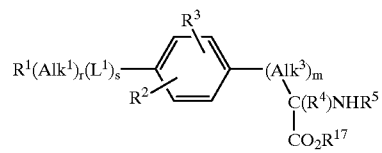

(3)

(where $R^{12}$ is as just described) or a salt thereof with an acid of formula (4):

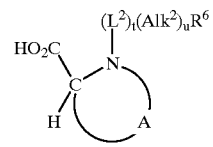

(4)

or an active derivative thereof.

Active derivatives of acids of formula (4) include anhydrides, esters and halides. Particular esters include pentafluorophenyl or succinyl esters.

The coupling reaction may be performed using standard conditions for reactions of this type. Thus for example the reaction may be carried out in a solvent, for example an inert organic solvent such as an amide, e.g. a substituted amide such as dimethylformamide, an ether, e.g. a cyclic ether such as tetrahydrofuran, or a halogenated hydrocarbon, such as dichloromethane, at a low temperature, e.g. around −30° C. to around ambient temperature, optionally in the presence of a base, e.g. an organic base such as an amine, e.g. triethylamine, pyridine, or dimethylaminopyridine, or a cyclic amine, such as N-methylmorpholine.

Where an acid of formula (4) is used, the reaction may additionally be performed in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively, the acid may be reacted with a chloroformate, for example ethylchloroformate, prior to reaction with the amine of formula (3).

Where appropriate the coupling reaction may be carried out earlier in the synthesis of the compound of the invention, for example by using an acid of formula (4) where $R^6(Alk^2)_u(L^2)_t$— is a hydrogen atom and manipulating the resulting ester to introduce any desired $R(^6Alk^2)_u(L^2)_t$— group. Similarly, intermediate esters of formula (2), or compounds of formula (1), may be manipulated to introduce particular $R^6(Alk^2)_t(L^1)_s$—, $R^2$ and/or $R^3$ groups or modify existing $R^1$ and/or $R^6$ substituents. Typically, such manipulation may involve standard substitution approaches employing for example alkylation, arylation, acylation, halogenation, sulphonylation, nitration or coupling reactions.

Thus in one example, a compound wherein $R^1(Alk^1)_r(L^1)_s$— is a —$L^1$ H group may be alkylated or arylated using a reagent $R^1(Alk^1)_rX$ in which $R^1$ is other than a hydrogen atom and X is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group.

The alkylation or arylation reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran.

In another example, a compound where $R^1(Alk^1)_r(L^1)_s$ is a —$L^1H$ group and/or $R^6(Alk^2)_2(L^2)_2$— is a hydrogen atom may be functionalised by acylation, for example by reaction with a reagent $R^1(Alk^1)_rL^1X$ [wherein $L^1$ is a —C(O)—, —CH$_2$C(O)— or —NHC(O)— group], $R^6(Alk^2)_u$COX or $R^6(Alk^2)_u$NHCOX in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature, or by reaction with $R^1(Alk^1)_rCO_2H$ or $R^6(Alk^2)_uCO_2H$ or an activated derivative thereof, for example as described above for the preparation of esters of formula (2).

In a further example a compound may be obtained by sulphonylation of a compound where $R^1(Alk^1)_r(L^1)_s$ is an —OH group by reaction with a reagent $R^1(Alk^1)_rL^1$Hal [in which $L^1$ is —SO$_2$— and Hal is a halogen atom such as a chlorine atom] in the presence of a base, for example an inorganic base such as sodium hydride in a solvent such as an amide, e.g. a substituted amide such as dimethylformamide at for example ambient temperature.

In another example, a compound where $R^1(Alk^1)_r(L^1)s$ is a —$L^1H$ group, may be coupled with a reagent $R^1OH$ (where $R^1$ is other than a hydrogen atom) or $R^1 Alk^1 OH$ in a solvent such as tetrahydrofuran in the presence of a phosphine, e.g. triphenylphosphine and an activator such as diethyl, diisopropyl- or dimethylazodicarboxylate to yield a compound containing a $R^1(Alk^1)_rO$— group.

Intermediates of formulae (3) and (4), $R^1(Alk^1)_rX$, $R^1((Alk^1)_rL^1X$, $R^6(Alk^2)_uCOX$, $R^6(Alk^2)_uNHCOX$, $R^1(Alk^1)_rCO_2H, R^6(Alk^2)_uCO_2H, R^1OH$ and $R^1Alk^1OH$ are either known compounds or may be prepared from known starting materials by use of analogous processes to those used for the preparation of the known compounds and/or by treating known compounds using standard substitution approaches, for example by one or more of the alkylation, acylation, arylation, sulphonylation, hydrogenation and other manipulations described herein, such as particularly described for the preparation of the Intermediates in the exemplification section hereinafter.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

The following Examples illustrate the invention. All temperatures are in ° C. The following abbreviations are used:
EDC—1-(3-dimethylaminopropyl)3-ethycarbodiimide;
DMF—dimethylformamide; DMSO—dimethylsulphoxide;
HOBT—1-hydroxybenzotriazole; THF—tetrahydrofuran;
TFA—trifluoroacetic acid; NMM—N-methylmorpholine;
DCM—dichloromethane; Ph—phenyl;
Boc—tert-butoxycarbonyl; EtOAc—ethyl acetate;
MeOH—methanol; LDA—lithium diisopropylamide
tyr—tyrosine; Ar—aryl;
HetAr—heteroaryl; pyr—pyridine;
thiopro—thioproline; Bu—butyl
app.—apparent; AcOH—acetic acid;
Et$_2$O—diethylether; sym.—symmetrical;
EtOH—ethanol
DBU—1,8-diazabicyclo[5.4.0]undec-7-ene

INTERMEDIATE 1

N-Boc-D-thioproline-L-4-aminophenylalanine methyl ester

EDC (11.31 g, 59 mmol) was added over a period of 5 mins to an ice cold solution of 4-aminophenylalanine methyl ester dihydrochloride (14.3 g, 54 mmol), HOBT (8.67 g, 64 mmol), NMM (16.2 g, 17.6 ml, 160 mmol) and N-Boc-D-thioproline (13.74 g, 59 mmol) in DMF (150 ml). The reaction was warmed to room temperature and stirred for 16 h. The volatiles were evaporated in vacuo and the residue partitioned between EtOAc (200 ml) and saturated Na$_2$CO$_3$ solution (100 ml). The organic layer was separated, washed with saturated Na$_2$CO$_3$ (2×100 ml) and brine (50 ml), dried over MgSO$_4$ and the solvent evaporated in vacuo. The product was purified by chromatography (SiO$_2$; DCM MeOH 97:3) to give the title compound as a pale orange foam (15 g, 64%). δH (DMSO-d$^6$, 360K) 7.87 (1 H, d, J 8.0 Hz, NH), 6.84 (2 H, d, J 8.3Hz, Ar—H), 6.50 (2 H, d, J 8.3 Hz, Ar—H), 4.62 (1 H, d, J 9.1 Hz, NCH$_A$H$_B$S), 4.60 (1 H, m, CHα-thiopro), 4.48 (1 H, dt, J 5.8, 8.2 Hz, CH$_α$Ph), 4.27 (1 H, d, J 9.1 Hz, NCH$_A$H$_B$S), 3.62 (3 H, s, CO$_2$CH$_3$), 3.23 (1 H, dd, J 7.5, 11.6 Hz, CHCH$_A$H$_B$S), 2.91–2.75 (3 H, m, CHCH$_A$CH$_B$S and CH$_2$Ar) and 1.40 (9 H, s, $^t$Bu). m/z (ESI, 15 V) 410 (MH$^+$).

INTERMEDIATE 2

N-Boc-D-thioproline-(N'-2,6-dichlorobenzoyl)-L-4-aminophenylalanine methyl ester 2,6-Dichlorobenzoyl chloride (0.61 g, 2.9 mmol) was added to a solution of Intermediate 1 (1.0 g, 2.4 mmol) and NMM (0.28 g, 2.88 mmol) in DCM (10 ml). The reaction was stirred at room temperature for 16 h then partitioned between CM (50 ml) and saturated Na$_2$CO$_3$ solution (20 ml). The aqueous layer was separated and extracted with DCM (2×50 ml). The combined organic layers were washed with brine (50 ml), dried over MgSO$_4$ and the solvent evaporated in vacuo to give a foam which was purified by chromatography (SiO$_2$; DCM/MeOH 97:3) to give the title compound as a white foam (1.3 g, 91%). δH (DMSO-d$^6$, 350K) 10.41 (1 H, s, NH), 8.08 (1 H, d, J 8.2 Hz, NH), 7.59 (2 H, d, J 8.5 Hz, Ar—H), 7.55 –7.44 (3 H, m, Ar—H), 7.19 (2 H, d, J 8.5 Hz, Ar—H), 4.62–4.56 (2 H, m, CH$_{6O}$-thiopro and CH__—Ph), 4.62 (1 H, d, J 9.1 Hz, NCH$_A$H$_B$S), 4.27 (1 H, d, J 9.1 Hz, NCH$_A$H$_B$S), 3.66 (3 H, S, CO$_2$CH$_3$), 3.23 (1 H, dd, J 11.5, 7.5 Hz, CHCH$_A$H$_B$S), 2.91–2.75 (3 H, m, CHCH$_A$H$_B$S and CH$_2$Ar) and 1.39 (9 H, s, $^t$Bu). m/z (ESI, 15 V) 582 (MH+).

INTERMEDIATE 3

D-Thioproline-(N'-2,6-dichlorobenzoyl)-L-4-aminophenylalanine methyl ester hydrochloride A solution of Intermediate 2 (1.3 g, 2.2 mmol) in EtOAc (20 ml) was treated with a solution of anhydrous EtOAc/hydrochloric acid (~4M, 10 ml) and stood for 2.5 h at room temperature. The volatiles were evaporated in vacuo to give the title compound as an off-white solid (1.2 g, 98%). δH (CD$_3$OD) 8.86 (1 H, d, J 8.6 Hz, NH), 7.61 (2 H, d, J 8.6 Hz, Ar—H), 7.50–7.39 (3 H, m, Ar—H), 7.23 (2 H, d, J 8.6 Hz, Ar—H), 4.87 (1 H, m, CH$_\alpha$-thiopro), 4.49 (1 H, t, J 7.4Hz, CHα-Ph), 4.35 (2 H, s, NCH$_2$S), 3.64 (3 H, s, CO$_2$CH$_3$), 3.42–3.27 (2 H, m, CHCH$_A$H$_B$S and ArCH$_A$H$_B$), and 3.00–2.73 (2 H, m, CHCH$_A$H$_B$S and ArCH$_A$H$_B$). m/z (ESI, 15 V), 482, 484 (MH+)

INTERMEDIATE 4

N-(Pyrid-3-ylacetyl)-D-thioproline-(N'-2,6-dichlorobenzoyl)-L-4-aminophenylalanine methyl ester EDC (0.48 g, 2.5 mmol) was added to a solution of Intermediate 3 (1.2 g, 2.3 mmol), HOBT (0.38 g, 2.8 mmol) NMM (0.51 g, 5.1 mmol) and 3-pyridylacetic acid hydrochloride (0.40 g, 2.3 mmol) in DMF (10 ml) and the reaction stirred at room temperature for 16 h. The volatiles were evaporated in vacuo and the residue partitioned between saturated Na$_2$CO$_3$ solution (30 ml) and EtOAc (50 ml). The organic layer was separated, washed with saturated Na$_2$CO$_3$ solution (30 ml) and brine (30 ml) and dried over MgSO$_4$. The solvent was evaporated in vacuo and the residue was purified by chromatography (SiO$_2$; DCM/MeOH 95:5) to give the title compound as a white foam (1.06 g, 76%). δH (DMSO-d$^6$, 390K) 10.20 (1 H, s, NH), 8.44 (2 H, m, Ar—H), 7.63–7.17 (9 H, m, pyr-H, Ar—H), 4.93 (1 H, dd, J 4.0, 7.4 Hz, CH$_\alpha$-thiopro), 4.87 (1 H, d, J 9.2 Hz, NCH$_A$H$_B$S), 4.61 (1 H, dt, J 5.7, 8.2 Hz, CH$_\alpha$-Ph), 4.46 (1 H, d, J 9.2 Hz, NCH$_A$H$_B$S), 3.74 (2 H, m, CH$_2$pyr), 3.66 (3 H, S, CO$_2$CH$_3$) and 3.32–2.95 (4 H, m, CHCH$_2$S and Ar—CH$_9$). m/z (ESI, 15 V), 601 (MH+).

INTERMEDIATE 5

N-Acetyl-D-thioproline-L-4-aminophenylalanine methyl ester

NMM (1.13 g, 1.24 ml, 11.19 mmol), HOBT (0.61 g, 4.52 mmol), N-acetyl-D-thioproline (0.72 g, 4.11 mmol) and EDC (0.79 g, 4.11 mmol) were added sequentially to a stirred solution of L-4-aminophenylalanine methyl ester dihydrochloride (1.0 g, 3.75 mmol) in dry DMF (10 ml). After stirring at room temperature for 4 h the solvent was removed in vacuo. The residue was partitioned between EtOAc (70 ml) and 10% aqueous Na$_2$CO$_3$ (30 ml). The phases were separated and the aqueous phase repeatedly extracted with EtOAc (4×30 ml). The combined organic extracts were washed with brine (10 ml), dried (Na$_2$SO$_4$) and evaporated in vacuo. The resulting oil was chromatographed (SiO$_2$; 3:97 to 5:95 MeOH/DCM) affording the title compound as a white foamy solid (0.97 g, 74%): δH (CD$_3$OD) (two rotameric species) 6.93 (d, J 8.3 Hz), and 6.91 (d, J 8.3 Hz) together (2 H, ArH), 6.64 (2 H, d, J 8.3 Hz, ArH), 4.81–4.60 (3H, m, CH$_\alpha$-thiopro, CH$_\alpha$-Ph, NCH$_A$H$_B$S), 4.53 (d, J 10 Hz), and 4.43 (d, J 10 Hz) together (1 H, NCH$_A$H$_B$S), 3.71 (s) and 3.69 (s) together (3H, CO$_2$CH$_3$), 3.37–2.81 (4 H, m, CHCH$_2$S and CH$_2$Ar), 2.14 (s) and 1.90 (s) together (3H, COCH$_3$); m/z (ESI, 27 V) 352 (MH+).

INTERMEDIATE 6

3.5-Dichloro-isonicotinic acid

A solution of 3,5-dichloropyridine (5.00 g, 33.8 mmol) in THF (25 ml) was added to a solution of LDA [generated from nBuLi (2.5M solution in hexanes, 14.9 ml, 37.2 mmol) and diisopropylamine (4.10 g, 5.7 ml, 40.6 mmol)] in THF (25 ml) at −78° under nitrogen, to give a yellow/brown slurry. The reaction was stirred for 30 min at −78° then CO$_2$ gas was bubbled through to give a clear brown solution that slowly gave a precipitate, warmed to room temperature over 2 h, then quenched with water (20 ml) and partitioned between diethylether (100 ml) and 1M NaOH (100 ml). The aqueous layer was separated and acidified to pH1 with concentrated hydrochloric acid and then extracted with 10% MeOH in DCM (100 ml×3). The combined organic layers were dried over MgSO$_4$ and the solvent removed under vacuum to give a brown solid that was recrystallised from ethanol and dried under vacuum to give the title compound as pinkish crystals (2.63 g, 41%). δH (DMSO-d$^6$) 8.74 (2 H, s, pyr-H). δC (DMSO-d$^6$) 163.5, 147.7, 141.0, 126.7

INTERMEDIATE 7

N-Acetyl-D-thioproline-(N'-3,5-dichloro-isonicotinoyl)-L-4-aminophenylalanine methyl ester A suspension of Intermediate 6 (0.50 g, 2.6 mmol) in DCM (10 ml) was treated with thionyl chloride (1.55 g, 0.95 ml, 13.0 mmol) and a drop of DMF, then heated to reflux for 1.5 h. The volatiles were removed under vacuum to give a yellow solid that was dissolved in DCM. NMM (0.53 g, 0.57 ml, 5.2 mmol) was added followed by Intermediate 5 (0.40 g, 1.37 mmol). The reaction was stirred for 16 h then partitioned between DCM (20 ml) and water (20 ml). The aqueous layer was extracted with DCM, the combined organic layers washed with NaHCO$_3$ solution (50 ml), dried over MgSO$_4$ and the solvent removed under vacuum, to give a brown gum, which was triturated with boiling methanol to give the title compound as a pale brown solid (0.13 g). δH (DMSO-d$^6$, 300K) two rotamers observed: 10.85 (1 H, s, NH), 8.79 (2 H, s, pyr-H), 8.59 (d, J 8.2 Hz) and 8.32 (d, J 8.2 Hz), together (1 H, NH), 7.56 (2 H, m, Ar—H), 7.22 (2 H, m, Ar—H), 4.80–4.70 (m), and 4.58–4.44 (m) and 4.47 (d, J 8.6 Hz) and 4.24 (d, J 9.6 Hz), together (4 H, 2×CH$_{60}$ and NCH$_2$S), 3.31 (3 H, s, CO$_2$CH$_3$), 3.20–2.82 (4 H, m, CH$_\alpha$CH$_2$Ar and CH$_\alpha$CH$_2$S), 2.06 (s) and 1.85 (s) together (3H, COCH$_3$). m/z (ESI, 60 V) 525 (MH$^+$).

INTERMEDIATE 8

N-Boc-D-thioproline-L-tyrosine methyl ester

NMM (0.39 g, 0.43 ml, 3.9 mmol), HOBT (0.57 g, 4.2 mmol), Boc-D-thioproline (0.91 g, 3.9 mmol), and EDC (0.75 g, 3.9 mmol) were added sequentially to a stirred solution of L-tyrosine methyl ester hydrochloride (0.82 g, 3.5 mmol) in dry DMF (10 ml). The reaction mixture was stirred at room temperature for 0.75 h. The DMF was removed in vacuo and the residue partitioned between EtOAc (70 ml) and 10% aqueous Na$_2$CO$_3$ (30 ml). The phases were separated and the aqueous phase re-extracted with EtOAc (2×20 ml). The combined organic extracts were washed with brine (10 ml), dried ($Na_2SO_4$) and evaporated in vacuo to afford the crude product as a viscous oil. Purification by flash chromatography ($SiO_2$; 5:95 MeOH/DCM) afforded the title compound as a white solid (1.1 g, 76%): δH ($CDCl_3$) 6.96 (2 H, d, J 8.5 Hz, ArH), 6.85 (1 H, br s NH), 6.72 (2 H, d, J 8.5 Hz, ArH), 5.95 (1 H. br s, OH), 4.81 (1 H, apparent dt, J 5.8, 8 Hz, $CH_α$-tyr), 4.73 (1 H, br s, CHα-thiopro), 4.63 (1 H, br d, J 9.0 Hz, $NCH_AH_BS$), 4.28 (1 H, d, J 9.0 Hz, $NCH_AH_BS$), 3.71 (3 H, s, $CO_2CH_3$), 3.37–3.28 (1 H, br m, $CHCH_AH_BS$), 3.21–3.10 (1 H, m, $CHCH_AH_BS$), 3.09–2.97 (2 H, m, $CH_2Ar$), and 1.45 (9 H, s, tBu); m/z (ESI, 27 V) 411 ($MH^+$).

INTERMEDIATE 9

D-Thioproline-L-tyrosine methyl ester hydrochloride

Hydrogen chloride gas was briefly bubbled through a stirred solution of Intermediate 8 [1.0 g in warm EtOAc (50 ml)]. The reaction mixture was stirred at ambient temperature for 1 h during which time the product precipitated from the solution. The solvent was removed in vacuo to afford the title compound as a white powder (0.85 g): δH ($CD_3OD$) 8.83 (1 H, d, J 8.3 Hz, NH), 7.02 (2 H, d, J 8.5 Hz, ArH), 6.71 (2 H, d, J 8.5 Hz, ArH), 4.74 (1 H, m, CHα-tyr), 4.54 (1 H, apparent t, 7.2Hz, CHα-thiopro), 4.36 (2 H, m, $NCH_2S$), 3.73 (3 H, s, $CO_2CH_3$), 3.42 (1 H, dd, J 7.4, 12 Hz, $CHCH_AH_BS$), 3.15 (1 H, dd, J 5.2, 14 Hz, $CH_AH_BAr$), 2.88 (1 H, dd, J 9.6, 14 Hz, $CH_AH_BAr$) and 2.79 (1 H, dd, J 7.0, 12.0 Hz, $CHCH_AH_BS$); m/z (ESI, 27 V) 311 $MH^+$).

INTERMEDIATE 10

N-(Pyrid-3-ylacetyl)-D-thioproline-L-tyrosine methyl ester

NMM (532 mg, 580 μL, 5.27 mmol), HOBT (388 mg, 2.87 mmol) 3-pyridylacetic acid hydrochloride (457 mg, 2.63 mmol) and EDC (506 mg, 2.63 mmol) were added sequentially to a stirred solution of Intermediate 9 in dry DMF (15 ml). The reaction mixture was stirred at room temperature for 5 h. The solvent was removed in vacuo and the residue partitioned between EtOAc (75 ml) and saturated aqueous $NaHCO_3$ (30 ml). The phases were separated and the aqueous phase re-extracted with EtOAc (3 ×30ml). The combined organic extracts were washed with brine (10 ml) dried ($Na_2SO_4$) and evaporated in vacuo to afford an off-white solid (1.06 g). This was heated in boiling EtOAc (40 ml) and, after cooling, the title compound was filtered off as a white powder (0.66 g, 64%) δH (DMSO-$d^6$, 400K) 8.64 (1 H, br s, OH), 8.44 (2 H, m, pyr-H), 7.84 (1 H, br d, J 7 Hz, NH), 7.60 (1 H, dd, J 2.1, 7.8 Hz, pyrH), 7.28 (1 H, dd, J 4.7, 7.8 Hz, pyrH), 6.98 (2 H, d, J 8.3 Hz, ArH) 6.86 (2 H, d, J 8.3 Hz, ArH), 4.93 (1 H, dd, J 4, 7.4 Hz, CHαthiopro), 4.85 (1 H, d, J 9.2 Hz, $NCH_AH_BS$), 4.54 (1 H, ddd, J 6.0, 7.3, 8.2 Hz, CHαtyr), 4.45 (1 H, d, J 9.2 Hz, $NCH_AH_BS$), 3.75 (1 H, d, J 16 Hz, $CH_AH_Bpyr$), 3.66 (1 H, d, J 16 Hz, $CH_AH_Bpyr$), 3.64 (3 H, S, $CO_2CH_3$), 3.29 (1 H, dd, J 7.4, 11.5 Hz, $CHCH_AH_BS$), 3.05–2.97 (2 H, m, $CHCH_AH_BS$ and $CH_AH_BAr$) and 2.88 (1 H, dd, J 8.2, 14.2 Hz, $CH_AH_BAr$); m/z (ESI, 27 V) 430 ($MH^+$).

INTERMEDIATE 11

N-(Pyrid-3-ylacetyl)-D4hioproline-(O-2,4,6-trichlorobenzoyl)-L-tyrosine methyl ester Sodium hydride (61 mg, 1.5 mmol) was added to a solution of Intermediate 10 (0.50 g, 1.2 mmol) in anhydrous DMF (10 ml). When the vigorous reaction had ceased 2,4,6-trichlorobenzoyl chloride (0.35 g, 1.44 mmol) was added and the reaction stirred for 16 h at room temperature. The reaction was poured into saturated $NaHCO_3$ solution (50 ml) and extracted with EtOAc (3×50 ml). The combined organic layers were washed with saturated $NaHCO_3$ solution (2×20 ml), brine (20 ml) and dried over $MgSO_4$. The solvent was evaporated in vacuo and the residue purified by chromatography ($SiO_2$; DCM/MeOH 95:5) to give the title compound as an orange oil (0.65 g, 74%) containing about 30% of the diastereomer at the thioproline stereocentre. δH (DMSO-$d^6$, 390K) 8.43 (2 H, m, pyr-H), 7.97 (1 H, m, NH), 7.77 (2 H, s, Ar—H), 7.62 (1 H, m, pyr-H), 7.36–7.16 (5 H, m, pyr-H, Ar—H), 4.92 (1 H, m, $CH_α$-thiopro), 4.86 (1 H, m, $NCH_AH_BS$), 4.65 (1 H, m, $CH_α$-tyr), 4.47 (1 H, m, $NCH_AH_BS$), 3.74 (2 H, m, $CH_2$pyr), 3.66 (3 H, s, $CO_2CH_3$), 3.36–2.98 (4 H, m, $ArCH_2$ and $CHCH_2S$). m/z (ESI, 30 V) 638 (MH+).

INTERMEDIATE 12

N-Boc-(Opyrimidin-2-yl)-L-tyrosine methyl ester

A solution of N-Boc tyrosine methyl ester (591 mg, 2 mmol) in DMF (5 ml) was added to a suspension of sodium hydride (60% in oil, 88 mg, 2.2 mmol) in DMF (5 ml) at room temperature. After 5 min, a solution of 2-chloropyrimidine (288 mg, 2.5 mmol) in DMF (3 ml) was added and the mixture stirred for 5 h. The reaction mixture was quenched with water and the DMF evaporated in vacuo. The residue was dissolved in EtOAc (150 ml) and washed with water (2×50 ml) and brine (50 ml), dried ($Na_2SO_4$) and evaporated in vacuo. The residue was purified by chromatography ($SiO_2$; EtOAc/hexane 60:40) to give the title compound as a colourless gum (470 mg, 63%): δH ($CDCl_3$) 8.55 (2 H, d, J 4.7 Hz, HetArH), 7.21–7.11 (4 H, m, ArH), 7.02 (1 H, t, J 4.7 Hz, HetArH), 5.00 (1 H, br d, CONH), 4.62 (1 H, br q, CHα), 3.72 (3 H, s, $CO_2CH_3$), 3.17–3.06 (2 H, m, $CH_2Ar$) and 1.42 (9 H, s, tBu); m/z (ESI, 15 V) 374 (MH+).

INTERMEDIATE 13

(O-Pyrimidin-2-yl)-L-tyrosine methyl ester hydrochloride

Gaseous HCl was bubbled through a solution of Intermediate 12 (460 mg, 1.23 mmol) in EtOAc (25 ml) for about 30 seconds. After 20 min the EtOAc was removed in vacuo to give the title compound as a white foam. δH (DMSO, 300K) 8.63 (2 H, d, J 4.9 Hz, HetArH), 7.32–7.25 (3 H, m, ArH+HetArH), 7.15 (2 H, d, J 8.5 Hz, ArH), 4.29 (1 H, br q, CHα), 3.69 (3 H, s, $CO_2CH_3$), 3.22 (1 H, dd, J 6.0, 14.1 Hz, $CH_AH_BAr$) and 3.14 (1 H, dd, J 7.1, 14.1 Hz, $CH_AH_BAr$).

INTERMEDIATE 14

N-Acetyl-D-thioproline-(O-pyrimidin-2-yl)-L-tyrosine methyl ester

EDC (259 mg, 1.35 mmol) was added to a solution of Intermediate 13 (1.23 mmol), N-acetyl-D-thioproline (215 mg, 1.23 mmol), HOBT (182 mg, 1.35 mmol) and NMM (285 μl, 2.6 mmol) in DCM (15 ml). The reaction mixture was stirred at room temperature overnight then diluted with DCM (150 ml). The DCM solution was washed with 10% citric acid (50 ml), saturated aqueous $NaHCO_3$ (50 ml) and water (50 ml), dried ($Na_2SO_4$) and evaporated in vacuo. The residue was purified by chromatography (SiO$_2$; DCM/MeOH, 93:7) to give the title compound as a slightly yellow gum (484 mg, 92%). δH (DMSO-d$^6$, 400K) 8.60 (2 H, dd, J 4.8 Hz, HetArH), 7.25 (2 H, s, J 8.7 Hz, ArH), 7.20 (1 H, t, J 4.8 Hz, HetArH), 7.09 (2 H, d, J 8.7 Hz, ArH), 4.83 (1 H, dd, J 4.0, 7.4 Hz, CHαthiopro), 4.77 (1 H, d, J 9.2 Hz, NCH$_A$H$_B$S), 4.63 (1 H, dt, J 5.6, 8.3 Hz, CHαtyr), 4.39 (1 H, d, J 9.1 Hz, NCH$_A$H$_B$S), 3.68 (3 H, s, CO$_2$CH$_3$), 3.26 (1 H, dd, J 7.4, 11.6 Hz CHCH$_A$H$_B$S), 3.16 (1 H, dd, J 5.7, 14.1 Hz, CH$_A$H$_B$Ar), 3.09–2.99 (2 H, m, CH$_A$H$_B$Ar+ CHCH$_A$H$_B$S) and 2.00 (3 H, s, CH$_3$CO); m/z (ESI, 27 V) 431 (MH+).

INTERMEDIATE 15

N-(Pyrid-3-ylacetyl)-D-thioproline-(O-2,6-dichlorobenzoyl)-L-tyrosine methyl ester To a suspension of NaH (60%, 103 mg, 2.56 mmol) in anhydrous DMF (25 ml) under argon was added Intermediate 10 (1.0 g, 2.33 mmol) in one portion. After 3 min. 2,6-dichlorobenzoyl chloride (0.54 mg, 0.37 ml, 2.56 mmol) was added and the mixture allowed to warm up to room temperature. After 2 h at room temperature a further portion of NaH (60%, 19 mg, 0.47 mmol) and 2,6-dichlorobenzoyl chloride (0.067 ml, 98 mg, 0.47 mmol) was added to the pale yellow mixture and the reaction stirred at room temperature over the weekend (60 h). The reaction mixture was poured into half-saturated NH$_4$Cl/ice and EtOAc added. The layers were separated and the aqueous layer extracted with EtOAc (2×50 ml). The combined organic layers were washed with saturated NaHCO$_3$ (1×100 ml), brine (1×100 ml) and dried over MgSO$_4$. The solvent was removed in vacuo to afford a pale yellow foam. Purification by flash chromatography (SiO$_2$; 1:99 to 3:97 MeOH/DCM) gave the title compound as an off-white foam (1.1 g, 78%). 5 H (DMSO-d$^6$, 400K) 8.48–8.43 (2 H, m, pyr-H), 8.01 (1 H, br d, NH), 7.63–7.52 (4 H, m, Ar(Cl)-H and pyrH), 7.34 (2 H, d, J 8.6 Hz, ArH), 7.34–7.26 (1 H, m, pyrH), 7.19 (2 H, d, J 8.6 Hz, ArH), 4.93 (1 H, dd, J 7.3, 4.0 Hz, CHαthiopro), 4.86 (1 H, d, J 9.2 Hz, NCH$_A$H$_B$S), 4.68–4.61 (1 H, m, CHαctyr), 4.46 (1 H, d, J 9.2 Hz, NCH$_A$H$_B$S), 3.76 (1 H, d, J 16 Hz, CH$_A$H$_B$pyr), 3.68 (1 H, d, J 16 Hz, CH$_A$H$_B$pyr), 3.67 (3 H, s, CO$_2$CH$_3$), 3.29 (1 H, dd, J 11.6, 7.3 Hz, CHCH$_A$H$_B$S), 3.19 (1 H, dd, J 14, 5.7 Hz, CH$_A$H$_B$Ar) and 3.09–3.00 (2 H, m, CHCH$_A$H$_B$S and CH$_A$H$_B$Ar).

INTERMEDIATE 16

N-Acetyl-D-thioproline-(N'-2,6-dichlorobenzoyl)-L-4-aminophenyl alanine methyl ester NMM (104 μg, 113 ml, 1.02 mmol), 2,6-dichlorobenzoyl chloride (216 mg, 148 μL, 1.02 mmol) and 4-dimethylaminopyridine (10 mg) were added sequentially to a stirred solution of Intermediate 5 (302 mg, 0.86 mmol) in dry DCM (10 ml). The reaction mixture was stirred at room temperature for 18 h under N$_2$. The solvent was removed in vacuo and the residue treated with 5% aqueous hydrochloric acid (~50 ml). The obtained solid was collected by filtration, with further aqueous hydrochloric acid washing followed by water and diethyl ether washing. The product was treated with hot MeOH (~10 ml) then cooled and filtered off to afford the title compound as a white powder (205 mg, 45%): δH (DMSO-d$^6$) (two rotamers observed) 10.95 (1 H, s, ArNHCO), 8.58 (d. J 7.9 Hz) and 8.31 (d, J 8.2 Hz) together (1 H, CHNHCO), 7.69–7.45 (5 H, m, ArH), 7.23–7.12 (2 H, m, ArH), 4.81–4.65 (m) and 4.58–4.48 (m) and 4.23 (d, J 9.5 Hz), together (4 H, NCH$_2$S and CHα-thiopro and CHαPh), 3.64 (3 H, s, CO$_2$CH$_3$), 3.18–2.75 (4 H, m, CHCH$_2$S and CH$_2$Ar), 2.05 (s) and 1.84 (s) together (3 H, COCH$_3$); m/z (ESI, 27 V) 524 (MH+).

INTERMEDIATE 17

N-Boc-D-thioproline-(O-benzyl)-L-tyrosine methyl ester

NMM (1.73 g, 1.9 ml, 17.13 mmol), HOBT (2.53 g, 18.74 mmol) N-Boc-D-thioproline (4.0 g, 17.17 mml) and EDC (3.30 g, 17.19 mmol) were added sequentially to a stirred solution of O-benzyl-L-tyrosine methyl ester hydrochloride (5.02 g, 15.59 mmol) in dry DMF (50 ml). The reaction mixture was stirred at room temperature under N$_2$ for 3 h. The DMF was removed in vacuo and the residue partitioned between EtOAc (150 ml) and 5% aqueous Na$_2$CO$_3$ (50 ml). The phases were separated and the aqueous phase re-extracted with EtOAc (2×50 ml). The combined organic extracts were washed consecutively with 5% aqueous hydrochloric acid (30 ml), 5% aqueous Na$_2$CO$_3$ (30 ml) and brine (20 ml) then dried (Na$_2$SO$_4$) and evaporated in vacuo to afford the title compound as a straw coloured oil (7.8 g). This was used without further purification but can be purified by flash chromatography (SiO$_2$; 2:98 MeOH/DCM). δH (DMSO-d$^6$), 7.48–7.28 (5 H, m, ArH), 7.03 (2 H, d, J 8.6 Hz, ArH), 6.88 (2 H, d, J 8.6 Hz, ArH), 6.82 (1 H, br s NH), 5.02 (2 H, s, PhCH$_2$O), 4.81 (1 H, apparent, dt, J 5.8 Hz, CHα-tyr), 4.73 (1 H, m, CHα-thiopro), 4.64 (1 H, br d J 9 Hz, NCH$_A$H$_B$S), 4.25 (1 H, d, J 9.2 Hz, NCH$_A$H$_B$S), 3.69 (3 H, s, CO$_2$CH$_3$), 3.34 (1 H, br d, J 11 Hz, CHCH$_A$H$_B$S), 3.13 (1 H, br d, CHCH$_A$H$_B$S) 3.06 (1 H, d, J 5.8 Hz, CH$_2$Ar) and 1.45 (9 H, s tBu); m/z (ESI, 15 V) 501 (MH+).

INTERMEDIATE 18

D-Thioproline-(O-benzyl)-L-tyrosine methyl ester

Intermediate 17 (8.2 g) was stirred in trifluoroacetic acid (50 ml) and DCM (50 ml) at room temperature for 1 h. The solvent was removed in vacuo and the residue partitioned between EtOAc (150 ml) and saturated aqueous NaHCO$_3$ (50 ml). The phases were separated and the aqueous phase re-extracted with EtOAc (32×50 ml). The combined organic extracts were washed with brine (30 ml), dried (Na$_2$SO$_4$) and evaporated in vacuo. The obtained solid was treated with diethyl ether (50 ml) and filtered off with a little ether washing affording the title compound as white needles (5.3 g, 81%): m.p. 138–140° . 5 H (1:1, CDCl$_3$/CD$_3$OD) 7.42–7.23 (5 H, m, PhH), 7.03 (2 H, d, J 8 Hz, ArH), 6.86 (2 H, d, J 8.7 Hz, ArH), 5.02 (2 H, s, OCH$_2$Ph), 4.68 (1 H, dd, J 7.5, 5.5 Hz, CHα-tyr), 4.10 (1 H, d, J 9.6 Hz, NCH$_A$H$_B$S), 3.96 (1 H, d, J 9.6 Hz, NCH$_A$H$_B$S), 3.96–3.94 (1 H, m, CHα-thiopro), 3.69 (3 H, s, CO$_2$CH$_3$), 3.13–3.04 (2 H, m) and 3.01–2.92 (2 H, m) together (4 H, CHCH$_2$S and CH$_2$Ar). m/z (ESI, 27 V) 401 (MH+).

INTERMEDIATE 19

N-(Pyrid-3-ylacetyl)-D-thioproline-(O-benzyl)-L-tyrosine methyl ester

HOBT (134 mg, 0.99 mmol), 3-pyridylacetic acid hydrochloride (157 mg, 0.90 mmol), and EDC (175 mg, 0.90 mmol) were added sequentially to a stirred solution of Intermediate 18 (330 mg, 0.83 mmol) in dry DMF(5 ml). The reaction mixture was stirred at room temperature for 6 h. The DMF was removed in vacuo and the residue partitioned between EtOAc (50 ml) and 5% aqueous Na$_2$CO$_3$ (30 ml). The phases were separated and the aqueous phase re-extracted with EtOAc (2×30 ml). The combined organic extracts were washed with brine (10 ml), dried ($Na_2SO_4$) and evaporated in vacuo. The obtained glassy solid was chromatographed ($SiO_2$; 2.5:97.5 MeOH/DCM) to yield the title compound as a colourless foam (240 mg, 56%): AH ($CDCl_3$) (two rotameric species) 8.52–8.31 (2 H, br m, pyrH), 7.56–7.43 (distorted br d, J ~8 Hz) and 7.40–7.23 (br m) and 7.27 (m) together (7 H, PhH, pyrHt and CONH), 7.01 (1 H, m, pyrH), 6.98 (2 H, d, J 8.3 Hz, ArH), 6.84 (2 H, d, J 8.3 Hz, ArH), 5.08–4.88 (m) and 4.82–4.38 (m) together (6 H, $CH_2O$, $NCH_2S$, CHα-thiopro and CHα-tyr), 3.78–3.62 (m and br s) and 3.44–2.92 (m) together (9 H, $CO_2CH_3$, $CH_2$pyr, $CH_2Ar$ and $CHCH_2S$); m/z (ESI) 520 (MH+).

INTERMEDIATE 20

N-Acetyl-D-thioproline-L-(4-benzoylphenylalanine) methyl ester

HOBT (240 mg, 1.78 mmol), N-acetyl-D-thioproline (286 mg, 1.63 mmol) and EDC (313 mg, 1.63 mmol) were added sequentially to a stirred solution of L-4-benzoylphenylalanine methyl ester (420 mg, 1.48 mmol) in dry DMF (10 ml). The reaction mixture was stirred at room temperature under $N_2$ for 2 h. The DMF was removed in vacuo and the residue partitioned between EtOAc (70 ml) and 5% aqueous $Na_2CO_3$ (30 ml). The phases were separated and the aqueous phase re-extracted with EtOAc (2×20 ml). The combined organic extracts were washed consecutively with 5% aqueous HCl (20 ml), 5% aqueous $Na_2CO_3$ (10 ml) and brine (10 ml), then dried ($Na_2SO_4$) and evaporated in vacuo to afford the crude product. Chromatography (silica; 55:95 MeOH/EtOAc) afforded the title compound as a colourless oil (610 mg, 93%): δH ($CDCl_3$,) (approximate 3:1 mixture of rotameric species) 7.8–7.7 (4 H, m), 7.62–7.57 (1 H, m), 7.52–7.45 (2 H, m), 7.29–7.22 (2 H, m), 7.10 and 6.70 (1 H, d, J 7.7 Hz), 5.05–5.00 (1 H, narrow m), 4.94–4.82 (1 H, m), 4.72 and 4.58 (1 H, d, J 8.7 Hz), 4.50 and 4.43 (1 H, d, J 8.7 Hz), 3.77 and 3.73 (3 H, s), 3.45 (1 H, dd, J 11.6, 2.9 Hz), 3.40–3.05 (3 H, m's), 2.16 and 1.90 (3 H, s); and m/z (ESI, 27 V) 441 (MH+).

INTERMEDIATE 21

N-Acetyl-D-thioproline-(N'-2,6-dichlorobenzyl)-L-4-aminophenylalanine methyl ester A solution of Intermediate 5 (1 g, 2.85 mmol), NMM (374 mg, 407 μl, 3.7 mmol) and 2,6-dichlorobenzyl bromide (889 mg, 3.70 mmol) in dry DCM (20 ml) was stirred at room temperature under $N_2$ for 18 h. The reaction was diluted with DCM (80 ml) and washed with saturated aqueous $NaHCO_3$ (30 ml). The phases were separated and the aqueous layer extracted with DCM (2×30 ml). The combined organic extracts were washed with brine (10 ml), dried ($Na_2SO_4$) and evaporated in vacuo. The obtained yellow oil was purified by flash chromatography (silica; EtOAc) affording the title compound as a colourless glass (0.78 g, 54%). 8 H (DMSO-$d^6$) (0.66:0.33 ratio of rotamers) 7.32 (2 H, app.d, J 7.8 Hz), 7.16 (1 H, app.t, J 7.8 Hz), 6.92 (2 H, distorted t, J 8.4 Hz), 6.83 and 6.48 (1 H, br d, J 8.0 Hz), 6.67 (2 H, d, J 8.4 Hz), 5.08–5.04 (0.66 H, m), 4.81–4.68 (1.33 H,m), 4.59–4.55 (2 H, br, s), 4.55–4.4 (2 H, m), 4.02–3.94 (0.66 H, br s), 3.75 and 3.70 (3 H, s), 3.42 (0.66 H, dd), 3.27 (0.66 H, dd), 3.16–2.90 (3 H m), 2.15 and 1.84 (3 H, s); m/z (ESI, 30 V) 510 and 510 (MH+).

INTERMEDIATE 22

N-(N-Acetyl-D-5,5-dimethyl-1,3-thiazolia-4-oyl)

NMM (111 mg, 120 μl, 1.10 mmol), HOBT (162 mg, 1.20 mmol), Intermediate 42 (b) (223 mg, 1.10 mmol) and EDC (211 mg, 1.10 mmol) were added sequentially to a stirred solution of O-benzyl-L-tyrosine methyl ester hydochloride (322 mg, 1 mmol) in dry DMF (5 ml). The reaction mixture was stirred at room temperature for 3 h and crude product obtained therefrom as described for Intermediate 17. Chromatography ($SiO_2$, 60:40 to 90:10 EtOAc/hexane) afforded the title compound as a colourless glass (355mg, 76%). 5 H ($CDCl_3$) 7.43–7.28 (5 H, m), 7.03–6.94 (2 H, m), 6.93–6.82 (2 H, m), 6.64 and 6.32 (1 H, d, J 8.0 Hz), 5.04 and 5.03 (2 H, s), 4.86–4.80 (1 H, m), 4.64–4.46 (2 H, m), 4.37 and 4.00 (1 H, s), 3.74 and 3.72 (3 H, s), 3.13–2.91 (2 H, m's), 2.04 and 1.81 (3 H, s), 1.48, 1.42 and 1.35 (6 H, s); m/z (ESI, 60 V) 471 (MH+).

INTERMEDIATE 23

N-(4-Morpholinoacetyl)-D-thioproline-O-(2,6-dichlorobenzyl)-L-tyrosine methyl ester Bromoacetyl bromide (1.20 g, 0.52 ml, 5.97 mmol) was added dropwise to a stirred, ice-bath cooled solution of D-thioproline-O-(2,6-dichlorobenzyl) tyrosine methyl ester (2.80 g, 5.97 mmol) and NMM (0.603 g, 0.66 ml, 5.97 mmol) in dry DCM (40 ml). The reaction mixture was stirred under $N_2$ for 2 h. The reaction was partitioned between DCM (100 ml) and 10% aqueous HCl (40 ml). The phases were separated and the aqueous phase re-extracted with DCM (40 ml). The combined organic extracts were washed consecutively with 10% aqueous HCl (20 ml), water (20 m) and brine (10 ml), dried ($Na_2SO_4$) and evaporated in vacuo. The obtained oil was chromatographed ($SiO_2$; 50:50 to 65:35, EtOAc/hexane; applied in DCM) to afford the N-bromoacetyl derivative as a white foam (1.95 g, 55%). (ESI, 60 V) 589 (MH+). This intermediate (840 mg, 1.42 mmol) was stirred with morpholine (248 mg, 250 μl, 2.84mmol) in MeOH (10 ml) for 18 h. The solvent was removed in vacuo and the residue partitioned between saturated aqueous $NaHCO_3$ (30 ml) and EtOAc (70 ml). The phases were separated and the aqueous phase re-extracted with EtOAc (3×30 ml). The combined organic extracts were washed with brine (10 ml), dried ($Na_2SO_4$) and evaporated in vacuo. The obtained crude oil was chromatographed [silica; DCM (400), MeOH (20), AcOH (3), $H_2O$ (2)] to afford the title compound as a foam (620 mg, 73%). δH (DMSO-$d^6$) (1:1 mixture of rotamers) 8.51 and 8.30 (1 H, d, J 8.0 Hz), 7.52 (2 H, d, J 8.0 Hz),7.42 (1 H, d, J 8.0 Hz), 7.13 (2 H, t, J 8.0 Hz), 6.95 (2 H, d, J 8.0 Hz), 5.18 (2 H, s), 5.19–5.10 (0.5 H, m), 4.90 (0.5 H, d, J 9.0 Hz), 4.80–4.72 (1 H, m), 4.62–4.47 (1.5 H, m), 4.24 (0.5 H, d, J 9.0 Hz), 3.62 (3 H, s), 3.6–3.46 (4 H, br m), 3.35–2.6 (6 H, m) and 2.48–2.25 (4H, br m).

INTERMEDIATE 24

L-4-(Methylamino)phenylalanine methyl ester dihydrochloride

Iodomethane (7.75 g, 3.4 ml, 54.6 mmol) was added to a stirred solution of N-Boc-L-4-aminophenylalanine methyl ester (10.7 g, 36.4 mmol) in dry DCM (60 ml), and stirred at room temperature for 24 h. NMM (1.83 g, 1.99 ml, 18.1 mmol) was added and the reaction stirred for 18 h. The volatiles were removed in vacuo and the residue partitioned between EtOAc (150ml) and saturated aqueous $NaHCO_3$ (100 ml). The phases were separated and the aqueous phase extracted with EtOAc (100 ml). The combined organic extracts were washed with brine (20 ml), dried ($Na_2SO_4$) and evaporated in vacuo to afford a dark oil. This was a mixture of the desired mono N-methylated product contaminated with more polar starting material and less polar N,N-dimethylated by-product. Chromatography (SiO$_2$, 40:60 to 75:25 Et$_2$O/hexane) afforded the desired N-Boc-L-4-(methylamino)phenyl alanine methyl ester (3.1 g) as a white crystalline solid. AH ( CDCl$_3$) 6.92 (2 H, d, J 8.0 Hz), 6.53 (2 H, d, J 8.0 Hz), 4.94 (1 H, br d, J 7.0 Hz), 4.50 (1 H, m), 3.70 (3 H, s), 2.98 (1 H, d, J 5.5 Hz), 2.81 (3 H, s) and 1.42 (9 H, s). This intermediate (3.05 g) was dissolved in methanol (100 ml) and HCl gas bubbled through the solution for 30 seconds. The reaction mixture was allowed to stand for 1 h. The volatiles were removed in vacuo to afford the title compound as an off white solid (2.56 g, 25% over 2 steps). δH (CD$_3$OD) 7.60 (2 H, d, J 8.0 Hz), 7.52 (2 H, d, J 8.0 Hz), 4.41 (1 H, t, J 6.8 Hz), 3.80 (3 H, s), 3.34 (2 H, m) and 3.08 (3 H, s).

INTERMEDIATE 25

N-Acetyl-D-thioproline-L-4-(methylamino) phenylalanine methyl ester

Intermediate 24 was reacted with N-acetyl-D-thioproline in a similar manner to that described for Intermediate 5. Chromatography (SiO$_2$; 3:97 to 5:95 MeOH/DCM) afforded the title compound as a white foam (1.34 g). 6 H (CDCl$_3$) (0.66:0.33 ratio of rotamers) 6.98–6.82 (3 H, m), 6.52 (2 H, d, J 8.4 Hz), 5.09–5.04 (0.66 H, m), 4.80–4.70 (0.66 H, m), 4.55 (0.66 H, d, J 8.7 Hz), 4.50–4.40 (0.33 H×2, obscured m), 4.41 (0.66 H, d, J 8.7 Hz), 3.74 (3 H×0.33, s), 3.70 (3 H,×0.66, s), 3.42 (0.66 H, dd), 3.27 (0.66 H, dd), 3.14–2.93 (2.66 H, m), 2.79 (3 H, s), 2.16 (3 H×0.66, s) and 1.88 (3 H×0.33); m/z (ESI) 366 (MH+).

INTERMEDIATE 26

N-(Diphenylmethylene)-4-(carbobenzyloxy) phenylalanine ethyl ester

A mixture of N-(diphenylmethylene)glycine ethyl ester (6.6 g, 24.9 mmol), benzyl 4-(bromomethyl)benzoic acid (7.61 g, 24.9 mmol) and potassium carbonate (50 mmol, 6.9 g) in acetonitrile (300 ml) was refluxed overnight. The solvent was removed in vacuo and the residue partitioned between EtOAc and water. The aqueous layer was extracted with EtOAc and the combined organic extracts were dried (Na$_2$SO$_4$) and concentrated in vacuo to give the title compound as an oil (13.0 g) δH (CDCl$_3$) 7.90 (2 H, d, J 8.3 Hz), 7.58 (2 H, d, J 7.3 Hz), 7.50–7.25 (11 H, m), 7.14 (2 H, d, J 8.1 Hz), 6.65 (2 H, d, J 6.8 Hz), 5.33 (2 H, m), 4.30–4.15 (3 H, br m), 3.32 (2 H, v br s) and 1.26 (3 H, t, J 7.1 Hz); m/z (ESI, 60 V) 492 (MH+).

INTERMEDIATE 27

4-(Carbobenzyloxy)phenylalanine ethyl ester

A solution of Intermediate 26 (13.0 g) in dilute hydrochloric acid (2M, 20 ml) and THF (200 ml) was stirred for 2 h at room temperature. The solvent was removed in vacuo. The residue was triturated with Et$_2$O to give a white solid, and recrystallisation from EtOH/EtOAc gave the HCl salt of the title compound as a white solid (4.24 g, 46.8%). The mother liquors were concentrated in vacuo to give a glassy solid, which was dissolved in EtOAc and washed with saturated NaHCO$_3$. The aqueous layer was re-extracted with EtOAc and the combined organic extracts dried (Na$_2$SO$_4$) and evaporated in vacuo. Chromatography (SiO$_2$, EtOAc) gave the title compound as a glassy solid (2.75 g, 33.8%). For the HCl salt: δH (DMSO-d$^6$) 7.96 (2 H, dd, J 6.6, 1.7 Hz), 7.48–7.37 (7 H, m), 5.35 (2 H, s), 4.29 (1 H, dd, J 7.7, 5.1 Hz), 4.10 (2 H, q, J 7.1 Hz), 3.27 (1 H, dd, J 14.0, 5.9 Hz), 3.15 (1 H, dd, J 14.0, 7.7 Hz) and 1.08 (3 H, t, J 7.1 Hz); m/z (ESI, 60 V) 328 (MH+).

INTERMEDIATE 28

N-Boc-4-(carbobenzyloxy)phenylalanine ethyl ester

NaOH (1M, 15.1 ml) was addd to Intermediate 27 (5 g, 13.75 mmol) in ten-butanol (110 ml). After a solution had been obtained, a solution of di-tert-butyl dicarbonate (3.6 g, 1 equivalent) in tert-butanol (50 ml) was added in portions. The reaction mixture was stirred at room temperature overnight then the solvent removed in vacuo. The resulting oil was taken up in water (200 ml) and the pH adjusted to pH3 with citric acid (10%). After extraction [EtOAc (3×250 ml)], the combined organic extracts were washed with saturated NaHCO$_3$ and water, dried (Na$_2$SO$_4$) and concentrated in vacuo to give the title compound as a yellow oil (6.1 g, 100%). δH (CDCl$_3$, 300 MHz) 7.9 (2 H, d, J 8.2 Hz), 7.5–7.35 (7 H, m containing d, J 8.2 Hz), 5.3 (2 H, s), 4.20–4.0 (3 H, m), 3.1–2.9 (2 H,m), 1.3 (9 H, s) and 1.2 (3 H, m); m/z (ESI, 60 V) 450 (MNa+).

INTERMEDIATE 29

N-Boc-4-carboxyphenylalanine ethyl ester

A mixture of Intermediate 28 (6.1 g, 14.3 mmol) and palladium on charcoal (10% Pd, 610 mg) in ethanol (150 ml) was stirred under a hydrogen atmosphere (balloon) at room temperature overnight. The catalyst was removed by filtration and the filtrate concentrated in vacuo to give the title compound as a white waxy solid (4.2 g. 87%) AH (CDCl$_3$) 8.0 (2 H, d, J 8.0 Hz), 7.3 (2 H, d, J 8.0 Hz), 4.8 (1 H, s), 4.4 (1 H, m), 4.1 (2 H,m), 3.2–3.1 (1 H, m), 3.0–2.8 (1 H, m), 1.3 (9 H, s) and 1.2 (3 H,m); m/z (ESI) 360 (MNa+).

INTERMEDIATE 30

N-Boc-4-[(3,5-dichlorophenyl)carboxamido] phenylalanine ethyl ester

Carbon tetrachloride (4.3 ml, 44.5 mmol) was added to a solution of Intermediate 29 (1.5 g, 4.45 mmol) and triphenylphosphine (1.4 g, 5.34 mmol) in acetonitrile (80 ml). The mixture was stirred for 2 h at room temperature. 3,5-Dichloroaniline (1.44 g, 8.9 mmol) was added and the reaction continued at room temperature for 20 h. The solvent was removed in vacuo and the residue partitioned between water and EtOAc. The aqueous layer was re-extracted with EtOAc and the combined organic extracts washed with dilute HCl, water and saturated NaHCO$_3$, dried (Na$_2$SO$_4$) and concentrated in vacuo. Chromatography (SiO$_2$; EtOAc/hexane, 1:4) gave the title compound as an off-white solid (1.20 g, 56%), δH (CDCl$_3$) 7.96 (1 H, brs), 7.76 (2 H, d, J 8.3 Hz), 7.62 (2 H, d, J 1.5 Hz), 7.24 (2 H, d, J8.5 Hz), 7.13 (1 H, t, J 1.5 Hz),5.03 (1 H, v br), 4.55 (1 H, brm), 4.17 (2 H,q, J 7.1 Hz), 3.2–3.0 (2 H, br m), 1.42 (9 H, s) and 1.42 (3 H, t, J 7.1 Hz); m/z (ESI, 60 V) 503 (MNa+).

INTERMEDIATE 31

N-Boc-4-(N'-thioacetyl)amino-L-phenylalanine methyl ester

To a solution of N-Boc-4-(N'-acetyl)amino-L-phenylalanine methyl ester (1.64 g, 4.88 mmol) in THF was added Lawesson's Reagent (1.08 g, 2.68 mmol, 0.55 eq).

The resulting suspension was heated to reflux for 3 h and then the reaction mixture was left stirring at room temperature overnight. The volatiles were then removed in vacuo and the oil obtained purified by column chromaography (SiO$_2$; DCM/EtOAc 100:0 to 80:20) to give the title compound as a yellow oil (1.72 g, 100%) δH (CDCl$_3$) 9.93 (br s) and 9.52 (br s) together (1 H, NHAr), 7.60 (2 H, d, J 8.3 Hz, ArH), 7.16–7.03 (2 H, m, ArH), 5.13–5.05 (1 H, m, NHBoc), 4.54–4.43 (1 H, m, CH), 3.65 (s) and 3.67 (s) together (3 H, CO$_2$Me), 3.13–2.90 (2 H, m, CH$_2$), 2.62 (s) and 2.52 (s) together (3 H, CSCH$_3$) and 1.36 (9 H, s, tBu); m/z (ESI, 60 V) 353 (MH+).

INTERMEDIATE 32

N-Boc-O-(trifluoromethylsulphonyl)-L-tyrosine methyl ester

Trifluoromethanesulphonic anhydride (4 ml, 23 mmol) was added to a mixture of N-Boc tyrosine methyl ester (5.9 g, 20 mmol) and pyridine (8 ml, 100 mmol) in DCM (30 ml) at 0°. After 30 min the reaction mixture was diluted with water (60 ml) and DCM (100 ml) and washed with aqueous NaOH (0.5M, 50 ml), water (60 ml), citric acid (10% solution, 2×75 ml) and water (60 ml), dried (Na$_2$SO$_4$) and evaporated in vacuo. Purification by column chromatography (SiO$_2$; EtOAc/hexane, 2:1) gave the title compound (7.76 g, 91%) as a colourless oil which solidified on standing. δH (CDCl$_3$) 7.25–7.18 (4 H, m, ArH), 5.01 (1 H, brd, CONH), 4.60 (1 H, brq, CHα), 3.71 (3 H, s, CO$_2$Me), 3.17 (1 H, dd, J 13.8, 5.8 Hz, CH$_A$H$_B$Ar), 3.03 (1 H, dd, J 13.6, 6.3 Hz, CH$_A$H$_B$Ar) and 1.41 (9 H, s, $^t$Bu); m/z (ESI, 15 V) 428 (MH+).

INTERMEDIATE 33

N-Boc-4-phenyl-L-phenylalanine methyl ester

Tetrakis(triphenylphosphine)palladium (0) (3 mol %, 69 mg) was added to a nitrogen purged mixture of Intermediate 32 (854 mg, 2 mmol), phenylboronic acid (488 mg, 4 mmol) and potassium carbonate (414 mg, 3 mmol) in toluene (20 ml). The mixture was heated at 85–90° for 2 h then diluted with EtOAc (150 ml) and washed with saturated aqueous NaHCO$_3$ (50 ml), water (50 ml), citric acid (10%, 50 ml), water (50 ml) and brine (50 ml), dried (Na$_2$SO$_4$) and evaporated in vacuo. Column chromatography (SiO$_2$; EtOAc/hexane; 20:80) gave the title compound (685 mg, 96%) as a colourless oil which solidified on standing. δH (CDCl$_3$, 300 MHz) 7.60–7.20 (9 H, m, ArH), 5.07 (1 H, br d, J 8.0 Hz, CONH), 4.65 (1 H, br q, CHα), 3.75 (3 H, s, CO$_2$Me), 3.19 (1 H, dd, J 13.8, 5.8 Hz, CH$_A$H$_B$Ar), 3.10 (1 H, dd, J 13.8, 6.1 Hz, CH$_A$H$_B$Ar) and 1.44 (9 H, s, $^t$Bu); m/z (ESI,15 V) 356 (MH+),

INTERMEDIATE 34

N-Boc-4-(3-prop-1-enyl)-L-phenylalanine methyl ester

Bistriphenylphosphine palladium (II) chloride (70 mg, 0.1 mmol) was added to a nitrogen purged mixture of Intermediate 32 (21.4 g, 5 mmol), allyltributyltin (1.55 ml, 5 mmol), and lithium chloride (425 mg, 10 mmol) in DMF (15 ml). The mixture was heated at 900 for 1 h then evaporated in vacuo. The residue was dissolved in Et$_2$O (200 ml) and washed with water (2×50 ml) and saturated potassium fluoride (50 ml), dried (Na$_2$SO$_4$) and evaporated in vacuo. Purification by column chromatography (SiO$_2$; EtOAc/hexane; 10:90 to 20:80) gave the title compound (1.49 g, 94%) as a colourless oil which solidified on standing. δH (CDCl$_3$) 7.12 (2 H, d, J 8.1 Hz,ArH), 7.05 (2 H, d, J 8.0 Hz, ArH), 6.02–5.88 (1 H, m, CH$_2$CH=CH$_2$), 5.10–5.04 (2 H, m, CH$_2$CH=CH$_2$), 4.95 (1 H, v br d, CONH), 4.57 (1 H, br q, CHα), 3.71 (3 H, s,CO$_2$Me), 3.36 (2 H, br d, J 6.7 Hz, CH$_5$CH=CH$_2$), 3.12–2.95 (2 H, m, CHCH$_2$Ar), and 1.42 (9 H, s, $^t$Bu); m/z (ESI, 15 V) 320 (MH+).

INTERMEDIATE 35

N-Boc-4-(2-benzo[b]furanyl)-L-phenylalanine methyl ester

Tetrakis(triphenylphosphine)palladium(0) (347 mg, 30 mol %) was added to a nitrogen purged mixture of Intermediate 32 (427 mg, 1 mmol) benzo[b]furan-2-boronic acid (324 mg, 2 mmol) and potassium carbonate (207 mg, 1.5 mmol) in toluene (10 ml). The mixture was heated at 90° for 4 h, diluted with EtOAc (100 ml), washed with saturated NaHCO$_3$ (30 ml), water (30 ml), citric acid (10%, 30 ml), water (30 ml) and brine (30 ml), dried (Na$_2$SO$_4$) and evaporated in vacuo. Column chromatography (SiO$_2$; DCM) gave the title compound (277 mg, 70%) as a white waxy solid. δH (CDCl$_3$) 7.79 (2 H, d, J 8.3 Hz, ArH), 7.59–7.50 (2 H, m, ArH), 7.31–7.20 (4 H, m, ArH), 6.99 (1 H, s, C=CH), 5.04 (1 H, br d J 7.7 Hz, CONH), 4.63 (1 H, br q, CHα), 3.73 (3 H, s,CO$_2$Me), 3.17 (1 H, dd, J 13.8, 5.7 Hz, CH$_A$H$_B$Ar), 3.08 (1 H, dd, J 13.7, 6.0 Hz, CH$_A$H$_B$Ar) and 1.43 (9 H, s,$^t$Bu); m/z (ESI, 15 V) 396 (MH+).

INTERMEDIATE 36

N-Boc-4[2-(1-phenylethenyl)]phenylalanine methyl ester

A mixture of N-Boc-4-iodo-L-phenylalanine methyl ester (1.22 g, 3 mmol) (Lei, H et al, J. Org. Chem (1994), 59, 4206–4210), palladium (II) acetate (67 mg, 0.3 mmol), tetrabutylammonium chloride (1.07 g, 3.6 mmol), tri(O-tolyl)phosphine (183 mg, 0.6 mmol), potassium carbonate (2.07 g, 15 mmol) and styrene (51 mg, 4.5 mmol) was heated in DMF (20 ml) at 90° for 22 h. The solvent was removed in vacuo, the residue dissolved in EtOAc (100 ml) and washed with water (30 ml), dilute HCl (1M, 30 ml), saturated NaHCO$_3$ (30 ml) and water (30 ml), dried (Na$_2$SO$_4$) and evaporated in vacuo. Column chromatography (SiO$_2$; MeOH/DCM, 1:99) gave the title compound (500 mg, 44%) as a light brown solid. δH (CDCl$_3$) 7.52–7.08 (11 H, m, ArH +CH=CH), 4.97 (1 H, br d, CONH), 4.60 (1 H, br q, CH$_α$), 3.72 (3 H, s, CO$_2$Me), 3.20–3.00 (2 H, m, CH$_2$Ar) and 1.49 (9H, s, $^t$Bu); m/z (ESI, 27 V) 382 (MH+).

INTERMEDIATE 37

N Boc-4-(3-pyridyl)phenylalanine methyl ester

A mixture of N-Boc-4-iodo-L-phenylalanine methyl ester (810 mg, 2 mmol, Lei, H et al, ibid) tetrakis (triphenylphosphine)palladium (0) (231 mg, 0.2 mmol), aqueous sodium carbonate (4 mmol, 2 ml of a 2M solution) and diethyl(3-pyridyl)borane (294 mg, 2 mmol) in dimethoxyethane (30 ml) was refluxed for 6 hr. The solvent was removed in vacuo, the residue dissolved in EtOAc (100 ml) and washed with water (30 ml) aqueous sodium thiosulphate (20 ml) and brine (30 ml) dried (Na$_2$SO$_4$)and evaporated in vacuo. Purification by column chromatography (SiO$_2$, EtOAc/hexane 30:70) gave the title compound (335 mg,47%) as a yellow oil. δH (CDCl$_3$) 8.81 (1 H, d, J 1.7 Hz, PyrH), 8.56 (1 H, dd, J 4.8, 1.6 Hz, PyrH), 7.84 (1 H, dt, J 7.9, 2.0 Hz, PyrH), 7.49 (2 H, d, J 8.2 Hz, ArH), 7.34 (1 H, ddd, J 7.9, 4.8, 0.6 Hz, PyrH), 7.23 (2 H, d, J 8.2 Hz, ArH), 5.09 (1 H, br d, J 7.8 Hz, CONH), 4.62 (1 H, br q, J 6.8 Hz, CHα), 3.73 (3 H, s, $CO_2Me$), 3.18 (1 H, dd, J 13.8, 5.6 Hz, $CH_AH_BAr$), 3.07 (1 H, dd, J 13.8, 5.8 Hz, $CH_AH_BAr$) and 1.40 (9 H, s, $^tBu$); m/z (ESI, 15 V) 357 (MH+).

INTERMEDIATE 38

2,6-Dichlorophenylacetylene

The title compound was prepared from 2,6-dichlorobenzaldehyde by the method of E. J. Corey and P. L. Fuchs, Tetrahedron Letters, (1972), 3769–3772 as off-white needles (hexane). m.p. 97–98°. δH ($CDCl_3$) 7.35–7.32 (2 H, m, ArH), 7.20 (1 H. dd, J 8.9, 7.2 Hz, ArH) and 3.68 (1 H, s, C≡CH); m/z (ESI) 170 (MH+).

INERMEDIATE 39

N-Acetyl-D-thioproline-4-(2,6-dichlorophenylacetylene)-L-phenylalanine methyl ester A solution of N-acetyl-D-thioproline-4-iodo-L-phenylalanine methyl ester (4.62 mg, 1 mmol), [prepared from N-Boc-4-iodo-L-phenylalnine methyl ester (Lei, H et al, ibid) deprotected by a similar method to that described for Intermediate 13 and then reacted with N-acetyl-D-thioproline according to the method described for Intermediate 14] in triethylamine (5 ml) and toluene (10 ml) was purged with nitrogen. Bis(triphenylphosphine) palladium dichloride (36 mg, 5mol %) and copper (I) iodide (20 mg, 10 mol %) were added. A solution of Intermediate 38 (257 mg, 1.5 mmol) in toluene (5 ml) was added over a period of 2 h via syringe pump. The mixture was stirred for a further 1 h at room temperature, then diluted with EtOAc (100 ml) and washed with dilute HCl (30 ml) and brine (30 ml), dried ($Na_2SO_4$) and evaporated in vacuo. Purification by column chromatography ($SiO_2$; MeOH/DCM, 3:97 to 5:95) gave the title compound (452 mg, 90%) as an orange solid. Recrystallisation from EtOAc gave an off-white solid (220 mg). δH (DMSO-$d^6$, 300K) (mixture of two rotameric species observed) 8.62 (d, J 8.3 Hz) and 8.34 (d, J 8.1 Hz) (together 1 H, CONH), 7.60 (2 H, d, J 8.3 Hz, $Cl_2ArH$), 7.51–7.49 (2 H, m, ArH), 7.43 (1 H, dd, J 8.9. 7.5 Hz, $Cl_2ArH$), 7.35–7.29 (2 H, m, ArH), 4.8–4.7 (2 H, m, CHα+$NCH_AH_BS$), 4.57–4.5 (1 H, m, CHα), 4.47 (d, J 8.7 Hz) and 4.23 (d, J 9.5 Hz) (together 1 H, $NCH_AH_BS$), 3.65 (3 H, s, $CO_2Me$), 3.35–2.80 (4 H, m, 2×$CHCH_2$) and 2.06 and 1.85 (3 H, each s, $COCH_3$); m/z (ESI) 505 (MH+).

INTERMEDIATE 40

N-Boc-4-(phenylacetylene)-L-phenylalanine methyl ester

The title compound was prepared in a similar manner to Intermediate 39 using N-Boc-4-iodo-L-phenylalanine methyl ester and phenylacetylene. Purification by column chromatography ($SiO_2$; EtOAc/hexane, 20:80) gave the title compound as a yellow gum (1.45 g, 77%). δH (DMSO-$d^6$) 7.55–7.27 (10 H, m, ArH+CONH), 4.25–4.18 (1 H, m, CHα), 3.62 (3 H, s, $CO_2Me$), 3.04 (1 H, dd, J 13.8, 5.1 Hz, $CH_AH_BAr$), 2.89 (1 H, dd, J 13.7, 10.1 Hz, $CH_AH_BAr$) and 1.33 (9 H, s, $^tBu$); m/z (ESI, 30 V) 380 (MH+).

INTERMEDIATE 41

N-Boc-4-[2-(1-phenylethyl)]-L-phenylalanine methyl ester

A mixture of Intermediate 40 (340 mg, 0.9 mmol) and palladium on charcoal (10% Pd wt/wt. 300 mg) in methanol (10 ml) was stirred under a hydrogen atmosphere (balloon) overnight. The catalyst was filtered off and the filtrate evaporated in vacuo. Column chromatography ($SiO_2$, EtOAc/hexane, 20:80) gave the title compound as a colourless gum (255 mg, 74%). δH ($CDCl_3$, 300 MHz) 7.31–7.02 (9 H, m, ArH), 4.96 (1 H, br d, CONH), 4.59 (1 H, br q, CHα), 3.71 (3 H, s, $CO_2Me$), 3.12–2.98 (2 H, m, $CHCH_2Ar$), 2.90 (4 H, s, $CH_2CH_2$) and 1.43 (9 H, s,$^tBu$); m/z (ESI, 15 V) 384 (MH+).

INTERMEDIATE 42 a) N-Acetyl-5,5-L-dimethyl-1,3-thiazolidine-4-carboxylic acid

Acetic anhydride (614 μl, 6.5 mmol) was added to a suspension of L-5,5-dimethylthiazolidine-4-carboxylic acid (1 g, 6.20 mmol) in DMF (6 ml). The mixture was stirred for 2 h at room temperature to give a colourless solution. The solvent was removed in vacuo to give a white solid. Recrystallisation (acetone) gave the title compound as white cubes (585 mg, 47%). δH (DMSO-$d^6$, 300K) (2 rotameric species observed) 4.80 (d J 8.8 Hz) and 4.70 (d, J 9.9 Hz) together (1 H, $NCH_AH_BS$), 4.71 (d, J 8.7 Hz) and 4.50 (3, J 9.9 Hz) together (1 H, $NCH_AH_BS$), 4.47 (s) and 4.25 (s) together (1 H, CHα), 2.06 (s) and 1.93 (s) together (3 H, $COCH_3$),1.53 (s) and 1.51 (s) together (3 H, $CMe_AMe_BS$), 1.41 (s) and 1.37 (s) together (3 H, $CMe_AMe_BS$) (acid proton not observed).

b) N-Acetyl-5,5-D-dimethyl-1,3-thiazolidine-4carboxylic acid

The title compound was prepared using the same procedure from the corresponding D-acid.

INTERMEDIATE 43

N-(Pyrid-3-ylacetyl)-D-thioproline-O-2,4,6-trichlorobenzyl)-L-tyrosine methel ester A solution of Intermediate 10 (429 mg, 1 mmol) in DMF (5 ml) was added to a suspension of sodium hydride (60% in mineral oil, 44 mg, 1.1 mmol) in DMF (5 ml) at 0°. After 10 min a solution of Intermediate 45 (302 mg, 1.1 mmol) in DMF (5 ml) was added. The reaction mixture was stirred at 0° for 2 h then at room temperature for 1 h, quenched with water (~1 ml) acid the solvents removed in vacuo. The residue was dissolved in EtOAc (150 ml) and washed with water (2×50 ml) and brine (50 ml), dried ($Na_2SO_4$) and evaporated in vacuo. Column chromatography ($SiO_2$:MeOH/$CH_2Cl_2$, 8:92) gave the title compound (435 mg, 70%). SH (DMSO-$d^6$, 300K) (2 rotameric species observed) 8.75 (d, J 7.9 Hz, CONH) and 8.44–8.35 (m) together (3 H, 2×PyrH+CONH), 7.76 (2 H,s, $Cl_3ArH_2$), 7.63–7.54 (1 H, m, PyrH), 7.34–7.30 (1 H, m, PyrH), 7.20–7.11 (2 H, m, ArH), 6.94–0.90 (2 H, m, ArH), 5.13 (s) and 5.11 (3) together (2 H, $OCH_2Ar$), 4.86–4.74 (2 H, m, CHα+$NCH_AH_BS$), 4.6–4.45 (m) and 4.29 (d. J 9.7 Hz) together (2 H, $NCH_AH_BS$+CHα), 3.83 (2 H, s, $PyrCH_2CO$), 3.63 (3 H, 9, $CO_2Me$), 3.20–2.69 (4 H, m, 2×$CHCH_2$) (acid proton not observed); m/z (ESI, 60 V) 622 (MH+).

INTERMEDIATE 44

2,4,6-Trichlorobenzylalcohol

A solution of lithium aluminium hydride (1M in THF, 18 ml, 18 mmol) was added to a solution of 2,4,6-trichlorobenzoyl chloride (4.35 g, 17.8 mmol ) in THF (70 ml) at 0°. After 1 h, water (685 μl), aqueous NaOH (3M, 685 μl) and water (2.06 ml) were added. The mixture was stirred vigorously for 1 h, the precipitate filtered off and the filtrate evaporated in vacuo to give a yellow solid. Recrystallisation from diisopropylether gave the title compound as white needles (2.63 g, 70%), m.p. 100–101°. δH (CDCl$_3$) 7.35 (2 H, s, ArH), 4.91 (2 H, br s, CH$_2$OH), 2.07 (1 H, br s, CH$_2$OH).

INTERMEDIATE 45

2,4,6-Trichlorobenzylbromide

Triphenylphosphine (1.57 g, 6 mmol) and carbon tetrabromide (1.99 g, 6 mmol) were added to a solution of Intermediate 44 (1.06 g, 5 mmol) in Et$_2$O (25 ml). The mixture was stirred at room temperature overnight. The precipitate was filtered off and the filtrate evaporated in vacuo. Chromatography (SiO$_2$, DCM) gave the title compound as a mobile colourless oil which crystallised on standing (1.17 g, 85%) m.p. 51–52°, δH (CDCl$_3$) 7.35 (2 H, s, ArH) and 4.70 (2 H, s,CH$_2$Br).

INTERMEDIATE 46

N-Acetyl-D-thioproline-O-(2-chloropyrimidin-4-yl)-L-tyrosine methyl ester

A solution of N-acetyl-D-thioproline-L-tyrosine methyl ester (1.76 g, 5 mmol), [prepared from N-acetyl-D-thioproline and tyrosine methyl ester by a similar method to the preparation of Intermediate 5] in DMF (10 ml) was added to a suspension of sodium hydride (60% in mineral oil, 210 mg, 5.25 mmol) in DMF (5 ml) at room temperature. After 10 min a solution of 2,4-dichloropyrimidine (782 mg, 5.25 mmol) in DMF (5 ml) was added. After 1 h water (1 ml) was added and the solvent evaporated in vacuo. The residue was dissolved in EtOAc (200 ml) and washed with water (3×50 ml) and brine (30 ml), dried (Na$_2$SO$_4$) and evaporated in vacuo. Chromatography (SiO$_2$, MeOH/DCM 5:95) gave the title compound as a white foam (1.59 g, 68%). δH (DMSO-d$^6$, 400K) 8.56 (1 H, d, J 5.7 Hz, PyrH), 7.9 (1 H, br d, CONH),7.32 (2 H, d,J 8.7 Hz, ArH), 7.15 (2 H, d, J 8.7 Hz, ArH), 6.99 (1 H, d, J 5.7 Hz, PyrH), 4.83 (1 H, dd, J 7.4, 3.9 Hz, CHαthiopro), 4.77 (1 H, d, J 9.2 Hz, NCHH$_B$S), 4.64 (1 H,dt, J 8.5, 5.6 Hz, CHαtyr),4.39 (1 H, d, J 9.2 Hz, NCH$_A$H$_B$S), 3.67 (3 H, s, CO$_2$Me), 3.26 (1 H, dd, J 11.6, 7.4 Hz, CHCH$_A$H$_B$S), 3.19 (1 H, dd, J 14.0, 5.7 Hz, CHCH$_A$H$_B$Ar), 3.09–3.00 (2 H, m, CHCH$_A$H$_B$S+ CHCH$_A$H$_B$Ar) and 2.00 (3 H, s,COCH$_3$); m/z (ESI, 15 V) 465 (MH+).

INTERMEDIATE 47

N-Acetyl-D-thioproline-O-[2-(4-methoxythiophenoxy)pyrimidin-4-yl]L-tyrosine methyl ester 4-Methoxythiophenol (129 μl, 1.05 mmol) was added to a suspension of sodium hydride (42 mg, 1.05 mmol) in DMF(5 ml) at 0°. After 10 min a solution of Intermediate 46 (465 mg, 1 mmol) in DMF (5 ml) was added. The mixture was stirred at room temperature overnight. The solvent was removed in vacuo, the residue dissolved in EtOAc (100 ml) and washed with water (2×50 ml) and brine (30 ml), dried (Na$_2$SO$_4$) and evaporated in vacuo. Column chromatography (SiO$_2$, MeOH/DCM, 5:95) gave the title compound as a colourless gum (327 mg, 58%). δH (DMSO-d$^6$, 300K) (2 rotameric species observed) 8.63 (d, J 7.9 Hz) and 8.4 (d) together (1 H, CONH), 8.40 (1 H, d, J 5.7 Hz, pyrH), 7.40 (2 H, d, J 8.1 Hz, ArH),7.22 (2 H, t, J 7.5 Hz, ArH), 7.05–7.01 (2 H, m, ArH), 6.93 (2 H, d, J 8.9 Hz,ArH),6.69 (1 H, d, J 5.7 Hz, PyrH), 4.78–4.68 (2 H, m, CHα+ NCH$_A$H$_B$S), 4.6–4.45 (1 H, m, CHαtyr), 4.46 (d, J 8.6 Hz) and 4.23 (d, J 9.7 Hz) together (1 H, NCH$_A$H$_B$S), 3.80 (3 H, s, ArOMe),3.65 (s) and 3.64 (s) together (3 H, CO$_2$Me), 3.18–2.72 (4 H, m, 2×CHCH$_2$), 2.05 (s) and 1.84 (s) together (3 H, COCH$_3$); m/z (ESI, 15 V) 569 (MH+).

INTERMEDIATE 48

N-Boc-N'-phthaloyl-4-amino-L-phenylalanine methyl ester

Phthaloyl dichloride (3.78 ml, 26.25 mmol) was added to a mixture of N-Boc-4-amino-L-phenylalanine methyl ester (7.35 g, 25 mmol), NMM (6.05 ml, 55 ml) and 4-dimethylaminopyridine (300 mg, 2.5 mmol) in THF (125 ml) at room temperature. The mixture was stirred at room temperature for 5 days. The bulk of the THF was removed in vacuo, the residue diluted with EtOAc (800 ml) and washed with dilute HCl (100 ml) and brine (100 ml), dried (Na$_2$SO$_4$) and evaporated in vacuo to give a pale yellow solid. Recrystallisation from EtOAc gave the title compound as white needles (7.91 g, 75%) m.p. 171–1720. δH (DMSO-d$^6$) 8.76–8.11 (4 H, m, ArH), 7.35–7.23 (5 H, m, ArH+ CONH), 4.2 (1 H,m, CHα), 3.62 (3 H, s, CO$_2$Me), 3.05–2.84 (2 H, m,CH$_2$Ar) and 1.33 (9 H, s, $^t$Bu); m/z (ESI, 60 V) 425 (MH+).

INTERMEDIATE 49

N-Boc-methyl-N'-phthaloyl-4-amino-L-phenylalanine methyl ester

A solution of Intermediate 48 (7.96, 18.8 mmol) in DMF (90 ml) was added via cannula to a suspension of sodium hydride (60% in mineral oil, 827 mg, 20.68 mmol) and methyl iodide (2.34 ml, 37.6 mmol) in DMF (100 ml) at 0°. The mixture was allowed to warm to room temperature and stirred overnight. Water (~2 ml) was added and the solvent removed in vacuo. The residue was dissolved in EtOAc (400 ml) and washed with water (2×100 ml) and brine (50 ml), dried (Na$_2$SO$_4$) and evaporated in vacuo. Column chromatography (SiO$_2$; EtOAc/hexane, 40:60) gave the title compound as a pale yellow gum. Recrystallaisation from MeOH/ isopropanol gave the title compound as pale yellow needles (5.44 g, 66%) m.p, 110–111°. δH (DMSO-d$^6$, 390K,) 7.94–7.86 (4 H, m, ArH(CO)$_2$),7.37 (4 H, s,ArH), 4.78 (1 H, dd, J 10.0, 5.4 Hz, CHα), 3.71 (3 H, s, CO$_2$Me), 3.29 (1 H, dd, J 14.4, 5.4 Hz, CH$_A$H$_B$Ar), 3.11 (1 H, dd, J 14.4, 10.0 Hz, CH$_A$H$_B$Ar), 2.72 (3 H, s,NMe) and 1.36 (9 H, s, $^t$Bu); m/z (ESI, 60 V) 461 (MNa+).

INTERMEDIATE 50

N-Boc-N-methyl-L-4-amino-L-phenylalanine methyl ester

Hydrazine monohydrate (366 μl, 7.54 mmol) was added to Intermediate 49 (3.00 g, 6.85 mmol) in absolute EtOH (70 ml). The mixture was stirred overnight at room temperature then refluxed for 4 h. After cooling to room temperature, the solid was filtered off and the filtrate evaporated in vacuo. DCM was added to the residue, the solid filtered off and the filtrate evaporated in vacuo. Column chromatography (SiO$_2$, EtOAc/hexane, 50:50) gave the title compound (2.04 g, 97%) as a colourless oil. 5 H (DMSO-d$^6$, 390K) 6.86 (2 H, d, J 8.4 Hz, ArH), 6.53 (2 H, d,J 8.4 Hz,ArH), 4.59 (1 H, dd, J 9.9, 5.5 Hz, CHα), 4.45 (2 H, br s, ArNH$_2$), 3.66 (3 H, s, CO$_2$Me), 3.04 (1 H, dd, J 14.4, 5.5 Hz, CH$_A$H$_B$Ar), 2.86 (1 H, dd, J 14.4, 9.9 Hz, CH$_A$H$_B$Ar), 2.67 (3 H, s, NMe) and 1.35 (9 H, s,$^t$Bu); m/z (ESI, 60 V) 331 (MNa+).

INTERMEDIATE 51

N-Boc-N-methyl-N'-3,5-dichloro-isonicotinoyl)-L-4-amino phenylalanine methyl ester A solution of 3,5-dichloro-isonicotinoyl chloride (1.53 g, 7.29 mmol) in THF (30 ml) was added to a solution of Intermediate 50 (2.04 g, 6.62 mmol) and NMM (800 μl, 7.29 mmol) in THF (40 ml) at 0°. The mixture was stirred overnight at room temperature and the bulk of the THF removed in vacuo. The residue was dissolved in DCM (200 ml) and washed with dilute HCl (50 ml) and saturated NaHCO$_3$ (50 ml), dried (Na$_2$SO$_4$) and evaporated in vacuo. Column chromatography (SiO$_2$, MeOH/CH$_2$Cl$_2$ 5:95 to 7:93) gave a white foam. Recrystallisation from EtOAc gave the title compound (2.53 g, 80%) as small white crystals m.p. 167–168°. δH (DMSO-d$^6$, 390K) 10.38 (1 H, br s, CONH), 8.67 (2 H, s, PyrH), 7.54 (2 H, br d, J 7.4 Hz, ArH), 7.22 (2 H, d, J 8.4 Hz, ArH), 4.71 (1 H, dd, J 9.9, 5.4 Hz, CHα), 3.70 (3 H, s, CO$_2$Me), 3.21 (1 H, dd, J 14.4, 5.4 Hz, CH$_A$H$_B$Ar), 3.02 (1 H, dd, J 14.4, 10.0 Hz, CH$_A$H$_B$Ar), 2.70 (3 H, s, NMe) and 1.38 (9 H, s,$^t$Bu); m/z (ESI, 60 V) 504 (MNa+).

INTERMEDIATE 52

2-Phenyl-D-1,3-thiazolidine-4-carboxylic acid

A solution of D-cysteine (5 g, 28.5 mmol) in pyridine (50 ml) was treated with benzaldehyde (4.61 ml, 45.4 mmol) and stirred at 500 for 4 h. The mixture was concentrated in vacuo and triturated with MeOH to give the title compound as a white solid (4.1 g, 69%) (55:45 mixture of diastereoisomers) δH (DMSO-d$^6$) 7.39 (5 H, m), 5.68 (s) and 5.51 (s) together (1 H, NCH(Ph)S), 4.24 (t, J 4.6 Hz) and 3.91 (dd, J 8.4, 7.4 Hz) together (1 H, CHα), 3.39 (1 H, m, CH$_A$H$_B$S) and 3.17 (1 H, m, CH$_A$H$_B$S).

INTERMEDIATE 53

N-Acetyl-2-phenyl-D-1,3-thiazolidine-4-carboxylic acid

A suspension of Intermediate 52 (3.6 g, 17.2 mmol) in DMF (50 ml) was treated dropwise with acetic anhydride (1.8 ml., 18.9 mmol) and stirred for 3 h at room temperature. The reaction was concentrated in vacuo to give a solid that was recrystallised from EtOAc/Et$_2$O to give the title compound as a single diastereomer (3.30 g, 76%) δH (DMSO-d$^6$, 390K) 7.64 (2 H, d, J 7.1 Hz, Ar—H), 7.32 (3 H, m, Ar—H), 6.31 (1 H, s, NCH(Ph)S), 4.97 (1 H, t, J 6.2 Hz, CHα), 3.44 (1 H, dd, J 11.8, 6.8 Hz, CHCH$_A$H$_B$S), 3.26 (1 H, dd, J 11.8, 5.9 Hz, CHCH$_A$H$_B$S) and 1.94 (3 H, s, COMe). m/z (ESI, 60 V) 252 (MH+).

INTERMEDIATE 54

5-Phenyl-1,3-thiazolidine-4-carboxylic acid

A mixture of β-phenyl-DL-cysteine hydrochloride [HT Nagasawa et al, J. Med. Chem (1987) 30, 1373] (1.32 g, 5.65 mmol) in acetic acid (11 ml) and formaldehyde (37 wt % aqueous solution, 0.43 ml) was heated to 80° to give a cloudy solution that was cooled to 30° and stirred for 2.5 h, then stood at room temperature for 16 h. The white precipitate was collected by filtration, washed with Et$_2$O and dried in vacuo to give the title compound (1.04 g, 88%). δH (DMSO-d$^6$) 7.57–7.54 (2 H, m, Ar—H), 7.40–7.29 (3 H, m, Ar—H), 4.90 (1 H, d, CHα-Thiopro), 4.59 (2 H, d, J 9.3 Hz, NCH$_2$S), 4.46 (1 H, d, J 9.8 Hz, CHPh). m/z (ESI, 60 V) 210 (MH+).

INTERMEDIATE 55

N-Acetyl-5-phenyl-1,3-thiazolidine-4-carboxylic acid

Acetic anhydride (0.27 g, 0.25 ml, 2.6 mmol) was added to a solution of Intermediate 54 (0.50 g, 2.4 mmol) in NMM (0.30 g, 0.33 ml, 3.0 mmol) and DMF (10 ml) and stirred for 7 h at room temperature. The solvent was removed in vacuo, the residue partitioned between DCM and 5% HCl, the organic layer dried (MgSO$_4$) and concentrated in vacuo to give a solid that was recrystallised from EtOAc to afford the title compound as a white solid (0.29 g, 48%) δH (CDCl$_3$) (two diastereomeric species observed) 7.38–7.26 (5 H, m, Ar—H), 5.19 (d, J 3.8 Hz) and 5.08 (d, J 9.6 Hz) togther (1 H, CHα-thiopro), 4.87 (d, J 3.8 Hz) and 4.60 (d, J 9.6 Hz) together (1 H, CHPh), 4.74 (2 H, s, NCH$_2$S), 2.22 (s) and 2.01 (s) together (3 H, COMe).

INTERMEDIATE 56

1-Thia-3-azaspiro[4,4]nonane-4-carboxylic acid

A mixture of β,β-tetramethylene-DL-cysteine (1.09 g, 5.15 mmol); [H. T. Nagasawa et al, ibid] in acetic acid (10 ml) and formaldehyde (37% aqueous solution, 0.39 ml) was heated to 80°, cooled to 30° when solution had occurred then stirred at this temperature for 1 h. The reaction was concentrated in vacuo to give the title compound as a white solid that was used without further purification (0.72 g, 75%). δH (DMSO-d$^6$) 4.44 (1 H, s, CHα), 4.36 (2 H, dd, J 13.6, 9.9 Hz, NCH$_2$S) and 2.33–1.69 (8 H, m, CH$_2$).

INTERMEDIATE 57

N-Acetyl-1-thia-3-azaspiro[4,4]nonane carboxylic acid

A solution of Intermediate 56 (300 mg, 1.60 mmol) in DMF (1 5 ml) and acetic anhydride (172 mg, 1.69 mmol) was stirred overnight at room temperature, concentrated in vacuo and partitioned between water (25 ml) and DCM (25 ml). The organic fraction was dried (MgSO$_4$) and concentrated in vacuo to give the title compound as a brown oil (0.31 g, 85%) which was used without further purification. δH (CDCl$_3$) 4.68 (3 H, m, CHα and NCH$_2$S), 2.19 (3 H, s, COMe) and 2.17–1.71 (8 H,m).

INTERMEDIATE 58

3,5-Dichloro-4-hydroxymethyl-pyridine

A solution of 3,5-dichloropyridine-4-carboxaldehyde (1.34 g, 7.6 mmol) in MeOH (10 ml) was treated with NaBH$_4$ (0.29 g, 7.6 mmol) and stirred at room temperature for 2 h. The reaction was quenched with water (5 ml) and concentrated in vacuo. The residue was partitioned between EtOAc (20 ml) and 10% HCl (10 ml). The aqueous layer was extracted with EtOAc and the combined organic extracts, washed with 10% NaHCO$_3$ solution, dried (MgSO$_4$) and concentrated in vacuo to give the title compound as a white solid (1.05 g, 78%). δH (CDCl$_3$) 8.52 (2 H, s, pyr-H), 4.94 (2 H, br s, CH$_2$OH) and 2.28 (1 H, br s, OH).

INTERMEDIATE 59

3,5-Dichloroisonicotinyl bromide

A solution of Intermediate 58 (0.50 g, 2.80 mmol) in DCM (10 ml) was treated with thionyl bromide (3.51 g, 1.32 ml, 16.9 mmol) and heated to reflux for 3 h. The reaction was quenched with 10% NaHCO$_3$ solution (10 ml) and extracted with DCM (25 ml). The organic layer was dried (MgSO$_4$) and concentrated in vacuo to give the title compound as a yellow oil that solidified on standing (0.65 g, 96%) and was used without further purification. δH (CDCl$_3$) 8.50 (2 H, s, pyr-H), 4.63 (2 H, s, CH$_2$Br). m/z (ESI, 60 V) 242 (MH+).

At

INTERMEDIATE 60

N-Acetyl-D-thioproline-(O-3,5-dichloroisonicotinoyl)-L-tyrosine methyl ester

To a slurry of NaH (88 mg, 2.2 mmol, 60% dispersion) in THF (4 ml) was added a solution of N-acetyl-D-thioproline-L-tyrosine methyl ester (0.70 g, 2.0 mmol) in DMF (6 ml). The reaction was stirred for 20 min at room temperature then a solution of Intermediate 59 (0.65 g, 2.7 mmol) in THF (6 ml) was added and the reaction stirred for 16 h, quenched with water (5 ml) and concentrated in vacuo. The residue was partitioned between water (20 ml) and DCM (20 ml), the organic layer dried (MgSO$_4$) and concentrated in vacuo to give an oil that was purified by chromatography (SiO$_2$; EtOAc) to give the title compound as a white solid (0.45 g, 44%). δH (CDCl$_3$) 8.55 (2 H, s, pyr-H), 7.09 (2 H, d, J 8.5 Hz, Ar—H), 6.93 (2 H, d, J 8.5 Hz, Ar—H), 5.22 (2 H, s, OCH$_2$), 5.04 (1 H, m, CHα-Thiopro), 4.80 (1 H, m, CHα-tyr), 4.59–4.40 (2 H, m, NCH$_2$S), 3.73 (3 H, s, CO$_2$Me), 3.47–3.03 (4 H, m, CHCH$_2$Ar+CHCH$_2$S) and 1.73 (3 H, s, COMe). m/z (ESI, 60 V) 512 (MH+).

INTERMEDIATE 61

N-Acetyl-D-thioproline-(N'-benzenesulphonyl)-L-4-aminophenyl alanine methyl ester A solution of Intermediate 5 (0.50 g, 1.71 mmol) in THF (10 ml) and triethylamine (0.21 g, 0.29 ml, 2.05 mmol) was treated with benzene sulphonyl chloride (0.30 g, 0.22 ml, 1.71 mmol) and stirred at room temperature for 16 h. The mixture was partitioned between EtOAc (20 ml) and water (20 ml), the organic layer separated and washed with 10% NaHCO$_3$ solution (20 ml), 10% HCl (10 ml), and brine (20 ml), dried (MgSO$_4$) and evaporated in vacuo to give a foam that was purified by chromatography (SiO$_2$; 1:99 AcOH/EtOAc) to give the title compound as a white foam (0.63 g, 80%). δH (CDCl$_3$), (2 rotamers observed) 7.75 (3 H, m, Ar—H+NH), 7.54–7.40 (3 H, m, Ar—H), 7.00 (4 H, m, Ar—H), 5.00 (m) and 4.79–4.65 (m) and 4.56 (d, J 8.8 Hz) and 4.45 (d, J 8.8 Hz) together (4 H, 2×CHα and NCH$_2$S), 3.73 and 3.66 (together 3 H, s,CO$_2$Me), 3.35–2.94 (4 H, m, CHαCH$_2$Ar and CHαCH$_2$S), 2.09 and 2.05 (together 3 H, s, COMe).

INTERMEDIATE 62

N-Acetyl-D-thioproline-4-(N'-isobutyloxycarbonyl)amino-L-phenylalanine methyl ester To a solution of Intermediate 5 (351 mg, 1.0 mmol) in DCM (10 ml) cooled to 0° was added NMM (121 μl, 1.1 mmol). After 15 min isobutylchloroformate (156 μl, 1.2 mmol) was added dropwise. The reaction mixture was stirred for a further 15 min at 0°, diluted with DCM (10 ml) and then washed with aqueous HCl (1M, 10 ml), saturated aqueous NaHCO$_3$ (10 ml) and brine (10 ml), dried (Na$_2$SO$_4$) and evaporated under reduced pressure. Purification of the residue by column chromatography (SiO$_2$; EtOAc/DCM, 1:1) gave the title compound as a white foam (400 mg, 89%). δH (CDCl$_3$) 7.48–6.82 (6 H, m, ArH and 2×NH), 5.00–4.30 (4 H, m, NCH$_2$S and 2×α-CH), 3.87 (2 H, d, J 6.7 Hz, OCH$_2$), 3.69 (s) and 3.64 (s) together (3 H, CO$_2$CH$_3$), 3.36–2.87 (4 H, m, CH$_2$Ar and SCH$_2$CH), 2.10 (s) and 1.81 (s) together (3 H, COCH$_3$), 1.90 (1 H, quin, J 6.7 Hz, CH$_2$CH(CH$_3$)$_2$) and 0.89 (6 H, d, J 6.7 Hz, CH(CH$_3$)$_2$); m/z (ESI, 60 V) 452 (MH+).

INTERMEDIATE 63

N-Acetyl-D-thioproline-4-(methylthioureido)-L-phenylalanine methyl ester

A solution of Intermediate 5 (351 mg, 1.0 mmol) ad methyl isothiocyanate (73 mg, 1.0 mmol) in Et$_2$O (10ml) and EtOH (10 ml) was refluxed for 18 h. The solvents were removed under reduced pressure and the cream foam obtained purified by column chromatography (SiO$_2$; MeOH/DCM 5:95) to give the title compound as a white foam (401 mg, 94%). 5 H (CDCl$_3$) 8.47 (s) and 8.21 (s) together (1 H, NH),7.17–6.48 (6 H, m, ArH and 2×NH), 4.88–4.45 (4 H, m, NCH$_2$S and 2×α-CH), 3.73 (s) and 3.69 (s) together (3 H, CO$_2$CH$_3$), 3.33–2.92 (7H, m, CH$_2$Ar, SCH$_2$CH and CSNHCH$_3$) and 2.02 (3 H, s, COCH$_3$); m/z (ESI, 60 V) 425 (MH+).

INTERMEDIATE 64

N-Acetyl-D-thioproline-4-(t-butylureido)-L-phenylalanine methyl ester

To a solution of Intermediate 5 (351 mg, 1.0 mmol) in acetonitrile (10 ml) was added t-butylisocyanate (113 μl, 1.0 mmol). The reaction mixture was heated to reflux for 24 h. The solvent was then removed and the residue obtained purified by column chromatography (SiO$_2$; DCM/MeOH, 96:4) to give the title compound as a colourless oil (320 mg, 71%). δH (DMSO-d$^6$) 8.55 (d, J 8.0 Hz) and 8.26 (d, J 8.2 Hz) together (1 H, NH), 8.14 (1 H, s, NH), 7.25–6.99 (4 H, m,ArH), 5.91 (1 H, s, NH), 4.82–4.19 (4 H, m, SCH$_2$N and 2×α-CH), 3.62 (s) and 3.61 (s) together (3 H, CO$_2$Me), 3.49–2.72 (4 H, m, CH$_2$Ar and SCH$_2$CH), 2.08 (s) and 2.05 (s) and 1.85 (s) together (3 H, COCH$_3$) and 1.27 (9 H, s, C(CH$_3$)$_3$); m/z (ESI, 60 V) 451 (MH+).

INTERMEDIATE 65

N-Acetyl-D-thioproline-4-(isopropylureido)-L-phenylalanine methyl ester

To a solution of Intermediate 5 (351 mg, 1.0 mmol) in DCM (10 ml) was added isopropylisocyanate (118 μl, 1.0 mmol). The solution was stirred overnight at room temperature. The resulting white precipitate was collected and washed with DCM and dried to give the title compound (150 mg, 35%). 6 H (DMSO-d$^6$) 8.55 (d, J 8.1 Hz) and 8.26 (d, J 7.9 Hz) together (1 H, NH), 8.19 (1 H, s, NH), 7.32–7.20 (2 H, m, ArH), 7.10–6.99 (2 H, m, ArH), 5.92 (1 H, d, J 7.4 Hz, NH), 4.82–4.20 (4 H, m, NCH$_2$S and 2×CHα-H), 3.80–3.68 (1 H, m, CH(CH$_3$)$_2$), 3.62 (s) and 3.61 (s) together (3 H, CO$_2$Me), 3.25–2.75 (4 H, m, CH$_2$Ar and SCH$_2$CH), 2.05 (s) and 1.84 (s);together (3 H, COCH$_3$) and 1.08 (6 H, d, J 6.5 Hz, CH(CH$_3$)$_2$); m/z (ESI, 60 V) 437(MH+).

INTERMEDIATE 66

Methyl 2-azido-3-(4-[2-hydroxyhexafluoroisopropyl]phenyl)prop-2-enoate

To a solution of 4-(2-hydroxyhexafluoroisopropyl) benzaldehyde (1.0 g, 3.68 mmol) and methyl α-azidoacetate (4.23 g, 36.8 mmol) in MeOH (50 ml) cooled to −78° was added a methanolic sodium methoxide solution (0.5M, 58.8 ml, 29.4 mmol). The reaction mixture was allowed to warm slowly to room temperature and left stirring overnight. Saturated brine (100 ml) was then added and the solution thoroughly extracted with Et$_2$O. The combined organics were dried (Na$_2$SO$_4$) and evaporated under reduced pressure. The solid obtained was triturated with hexane:chloroform and the solution obtained reduced in vacuo to leave the title compound as a pale yellow solid (840 mg, 62%) δH (CDCl$_3$) 7.88 (2 H, d, J 8.5 Hz, ArH), 7.73 (2 H, d, J 8.5 Hz, ArH), 6.90 (1 H, s, C=CH) and 3.93 (3 H, S, CO$_2$Me); m/z (ESI, 60 V) 342 (MH+−N$_2$).

INTERMEDIATE 67

4-(2-Hydroxyhexafluoroisopropyl)-DL-phenylalanine methyl ester

A solution of Intermediate 66 (840 mg, 2.27 mmol) in MeOH (50 ml) was degassed thoroughly. Palladium on activated carbon (140 mg) was added and the reaction placed under a hydrogen atmosphere (H$_2$ balloon). The solution was stirred rapidly overnight. DCM (5 ml) was added and the catalyst removed by filtration through Celite®. Solvent was evaporated under reduced pressure to give the title compound (600 mg, 77%). δH (CDCl$_3$) 7.66 (2 H, d, J 8.2 Hz, ArH), 7.22 (2 H, d, J 8.2 Hz, ArH), 4.05 (2 H, br s, NH$_2$) 3.76 (1 H, dd, J 6.3, 6.3 Hz, CHα), 3.67 (3 H, s,CO$_2$Me), 3.10 (1 H, dd, J 13.8, 5.5 Hz, CH$_A$H$_B$) and 2.98 (1 H, dd, J 13.8 and 7.1 Hz, CH$_A$H$_B$); m/z (ESI, 60 V) 346 (MH+).

INTERMEDIATE 68

Methyl 4-{[(2,6-dichlorophenyl)sulphonyl]methyl}benzoate 2,6-Dichlorobenzenesulphonylchloride (1 g, 4.07 mmol) was added to a solution of sodium sulphite (1.02 g, 8.14 mmol) in water (15 ml). The solution was made basic with the addition of 10% sodium hydroxide solution. The solution was then heated briefly and then cooled and any remaining solids removed by filtration. The solution was then acidified by the addition of 50% sulphuric acid and the resulting white precipitate collected by filtration and dried to give the sulphinic acid (0.86 g, 4.07 mmol). The acid (0.86 g) was then dissolved in acetonitrile (6 ml) and DBU (6.2 ml, 4.07 mmol) followed by the addition of methyl 4-(bromomethyl) benzoate (1.03 g, 4.48mmol). The reaction mixture was stirred overnight at room temperature. Water (50 ml) was then added and the mixture extracted with DCM (3×25 ml). The combined organics were dried (Na$_2$SO$_4$) and evaporated under reduced pressure. Purification by column chromatography (SiO$_2$; DCM) gave the title compound as a white solid (300 mg, 21%). δH (CDCl$_3$) 7.99–7.89 (2 H, m, ArH), 7.43–7.28 (5 H, m,ArH), 4.69 (2 H, s,CH$_2$) and 3.87 (3 H, s,CO$_2$Me); m/z (ESI, 60 V) 359 (MH+).

INTERMEDIATE 69

4-{[(2,6-Dichlorophenyl)sulphonyl]methyl}benzyl alcohol

Intermediate 68 (300 mg, 0.83 mmol) was dissolved in THF (5 ml). Lithium aluminium hydride (1M in THF, 0.83 ml, 0.83 mmol) was added dropwise. The resulting orange solution was stirred for 1 h at room temperature and then quenched with the dropwise addition of water (15 ml). The mixture was extracted with DCM (3×25 ml) and the combined organics dried (Na$_2$SO$_4$), filtered through a pad of Celite® and evaporated under reduced pressure to give the title compound as a colourless oil (284 mg, 100%) δH (CDCl$_3$) 7.40–7.20 (7 H, m, ArH), 4.72–4.60 (4 H, m, CH$_2$×2) and 2.18 (1 H, br s, OH); m/z (ESI, 60 V) 348 (MNH$_4$+).

INTERMEDIATE 70

4-{[(2.6-Dichlorophenyl)sulphonyl]methyl}benzyl bromide

Intermediate 69 (200 mg, 0.58 mmol) was dissolved in toluene (5 ml) and thionyl bromide (0.5 ml) was added. The resulting reaction mixture was stirred for 3 h. The volatiles were removed under reduced pressure and the residue azeotroped with toluene (×2). Purification by column chromatography (SiO$_2$; DCM/Hexane 1:1) gave the title compound as a colourless oil (180 mg, 79%) δH (CDCl$_3$) 7.41–7.20 (7 H, m, ArH), 4.65 (2 H, s,CH$_2$) and 4.43 (2 H, s,CH$_2$) m/z (ESI, 60 V) 412 (MNH$_4$+).

INTERMEDIATE 71

Ethyl 2 amino-3-(4-{[(2,6-dichlorophenyl) sulphonyl]methyl} propanoate

LDA (2M in heptane/THF/ethylbenzene, 2.10 ml, 4.19 mmol) was added to a stirred solution of N-(diphenylmethylene)glycine ether ester (1.07 g, 3.99 mmol) in THF (40 ml) cooled to −78°. The reaction mixture was stirred at this temperature for 40 min. A solution of Intermediate 70 (1.5 g, 3.81 mmol) in THF (20 ml) was then added dropwise. The reaction mixture was stirred for a further hour at −78°, then warmed slowly to ambient temperature, and quenched with saturated aqueous NH$_4$Cl (50 ml). Ethyl acetate (75 ml) was added and the organic phase separated. The aqueous layer was extracted with EtOAc (×2) and the combined organics dried (Na$_2$SO$_4$) and evaporated under reduced pressure. The residue was then dissolved in EtOH (50 ml) and 1M HCl (20 ml) was added. After 30min the solvents were removed and the resulting residue partitioned between EtOAc (100 ml) and saturated aqueous NaHCO$_3$. The phases were separated and the aqueous phase extracted with EtOAc (2×). The combined organics were dried (Na$_2$SO$_4$) and evaporated under reduced pressure. The resulting oil was purified by column chromatography (SiO$_2$; EtOAc) to give the title compound as a colourless oil (1.00 g, 60%) δH (CDCl$_3$) 7.61 (2 H, d, J 8.2 Hz, ArH), 7.27 (2 H, d, J 8.2 Hz, ArH), 7.22–7.19 (2 H, m, ArCl$_2$H), 7.12 (1 H, dd, J 9.2, 6.5 Hz,ArCl$_2$H), 4.73 (2 H, s, SO$_2$CH$_9$), 4.10 (2 H, q, J 7.1 Hz, CH$_2$CH$_3$), 3.65 (1 H, dd, J 7.5, 5.5 Hz, CH), 3.06 (1 H, dd, J 13.5, 5.5 Hz, CH$_A$H$_B$), 2.87 (1 H, dd, J 13.5, 7.5Hz, CH$_A$H$_B$), 1.45 (2 H, br s, NH$_2$) and 1.16 (3 H, t, J 7.1 Hz, CH$_2$CH$_3$); m/z (ESI, 60 V) 416 (MH+).

INTERMEDIATE 72

Ethyl 2-amino-3-{4-[(2,6-dichlorobenzyl)sulphonyl] phenyl}propanoate

The title compound was prepared in a similar manner to Intermediate 71 from 4-[(2,6-dichlorobenzy)sulphonyl] benzyl bromide N-(diphenyl-methylene)glycine ethyl ester. δH (CDCl$_3$) 7.38–7.29 (3 H, m, ArH), 7.15–7.06 (4 H, m, ArH), 4.60 (2 H, s,CH$_2$SO$_2$), 4.11 (2 H, q, J 7.1 Hz, CH$_2$CH$_3$), 3.63 (1 H, dd, J 7.7, 5.3 Hz, CH), 3.01 (1 H, dd, J 13.5, 5.3 Hz, CH$_A$H$_B$), 2.80 (1 H, dd, J 13.5, 7.7 Hz, CH$_A$H$_B$), 1.53 (2 H, br sm NH$_2$) and 1.21 (3 H, t, J 7.12 Hz, CH$_2$CH$_3$); m/z (ESI, 60 V) 416 (MH+).

EXAMPLE 1

N-(Pyrid-3-ylacetyl)-D-thioproline-(N'-2,6-dichlorobenzoyl)-L-4-aminophenylalanine A solution of Intermediate 4 (1.06 g, 1.08 mmol) in dioxane/MeOH (1:1, 60 ml) and water (30 ml) was treated with lithium hydroxide monohydrate (53.0 mg, 1.3 mmol) and stirred at room temperature for 1.5 h. The reaction was acidified to pH 4.5 with glacial acetic acid to give a precipitate which was isolated by filtration, washed with dilute acetic acid and hexane then dried in vacuo to give the title compound as a white solid (0.67 g, 65%). δH (DMSO-d$^6$, 390K) 10.19 (1 H, s, CO$_2$H), 8.43 (2 H, m, Ar—H), 7.88 (1 H, br s, NH), 7.62–7.41 (6 H, m, Ar—H, pyr-H), 7.28 (1 H, m, Ar—H), 7.20 (2 H, d, J 8.4 Hz, Ar—H), 4.94 (1 H, dd, J 4.1, 7.4 Hz, CH$_\alpha$-thiopro), 4.86 (1 H, d, J 9.2 Hz, NCH$_A$H$_B$S), 4.55 (1 H, m, CH$_\alpha$-Ph), 4.45 (1 H, d, J 9.2 Hz, NCH$_A$H$_B$S), 3.74 (2 H, m, CH$_2$pyr) and 3.31–2.96 (4 H, m, ArCH$_2$, CHCH$_2$S). m/z (ESI, 30 V) 587 (MH+).

EXAMPLE 2 a) N-Acetyl-D-thioproline-(N'-3,5-dichloroisonicotinoyl)-L-4-aminophenylalanine

A solution of Intermediate 7 (120 mg, 0.23 mmol) in THF (4 ml) and water (3 ml) was treated with lithium hydroxide monohydrate (14.4 mg, 0.34 mmol) and stirred for 2 h at room temperature. The reaction was acidified to pH1 with 10% hydrochloric acid and the volatiles were removed in vacuo. The solid residue was triturated with water, isolated by filtration and washed with water and dried in vacuo to give the title compound as an off-white solid (100 mg, 85%). δH (DMSO-d$^6$, 390K) 10.41 (1 H, s, NH), 8.68 (2H, s, pyr-H), 7.77 (1 H, br s, NH), 7.54 (2 H, br d, J 7.9 Hz, Ar—H), 7.23 (2 H, d, J 8.4 Hz, Ar—H), 4.83 (1 H, dd, J 4.0, 7.4 Hz, CH$_\alpha$-Thiopro), 4.76 (1 H, d, J 9.2 Hz, NCH$_A$H$_B$S), 4.54 (1 H, dt, J 5.4, 8.3 Hz, CH$_\alpha$-Ph), 4.38 (1 H, d, J 9.2 Hz, NCH$_A$H$_B$S), 3.25 (1 H, dd, J 7.4, 11.5 Hz, CHCH$_A$H$_B$S), 3.15 (1 H, dd, J 5.4, 14.1 Hz, ArCH$_A$H$_B$), 3.04–2.92 (2 H, m, CHCH$_A$H$_B$S and ArCH$_A$H$_B$) and 1.99 (3 H, s, COCH$_3$). m/z (ESI, 70 V) 511, (MH$^+$).

The following compounds were prepared in a similar manner to the compound of Example 2a):

b) N-Acetyl-D-thioproline-O-[2-(4-methoxythiophenoxy)pyrimidin-4-yl]-L-tyrosine
from Intermediate 47: δH (DMSO-d$^6$, 400K) 8.39 (1 H, d, J 5.6 Hz, PyH), 7.75 (1 H, br d, CONH), 7.41 (2 H, d, J 8.9 Hz, ArH), 7.21 (2 H, d, J 8.6 Hz, ArH), 7.00 (2 H, d, J 8.6 Hz, ArH), 6.92 (2 H, d, J 8.9 Hz, ArH), 6.64 (1 H, d, J5.6 Hz, PyrH), 4.83 (1 H, dd, J 7.3, 3.9 Hz, CHαthiopro), 4.77 (1 H, d, J 9.2 Hz, NCH$_A$H$_B$S), 4.57 (1 H, dt, J 8.3, 5.4 Hz, CHαtyr), 4.39 (1 H, d, J 9.1 Hz, NCH$_A$H$_B$S), 3.83 (3 H, s, OMe), 3.26 (1 H, dd, J 11.4, 7.4 Hz, CHCH$_A$H$_B$S), 3.18 (1 H, dd, J 14.1, 5.4 Hz, CHCH$_A$H$_B$Ar), 3.04–2.97 (2 H, m, CHCH$_A$H$_B$S+CHCH$_A$H$_B$Ar) and 1.99 (3 H, s,COCH$_3$) (acid signal not observed at 400K); m/z (ESI, 30 V) 555 (MH+).

c) N-Acetyl-D-thioproline-O-(2-chloropyrimidin-4-yl)-L-tyrosine
from Intermediate 46 as a white solid δH (DMSO-d$^6$, 400K) 8.56 (1 H, d, J 5.7 Hz, PyH), 7.72 (1 H, brs, CONH), 7.33 (2 H, d, J 8.7 Hz, ArH), 7.13 (2 H, d, J 8.7 Hz, ArH), 6.98 (1 H, d, J 5.7 Hz, PyH). 4.83 (1 H, dd, J 7.4, 4.0 Hz,CHαthiopro), 4.77 (1 H, d, J 9.2 Hz, NCH$_A$H$_B$S), 4.56 (1 H, br m, CHαtyr), 4.38 (1 H. d, J 9.3 Hz, NCH$_A$H$_B$S), 3.29–3.18 (2 H, m, 2×CHCH$_A$H$_B$), 3.07–3.00 (2 H, m,2×CHCH$_A$H$_B$) and 1.99 (3 H, s, COCH$_3$) (acid signal not observed at 400K); m/z (ESI, 15 V) 451 (MH+).

d) N-(Pyrid-3-ylacetyl)-D-thioproline-O-(2,4,6-trichlorobenzyl)-L-tyrosine
from Intermediate 43 as an off-white solid. δH (DMSO-d$^6$, 400K) 8.51 (2 H, br s PyH), 7.8 (1 H, br d, CONH), 7.65 (1 H,d, PyH), 7.61 (2 H, s,Cl$_3$ArH), 7.3 (1 H, dd, PyH), 7.16 (2 H, d, J 8.4 Hz, ArH), 6.93 (2 H, d, J 8.5 Hz,ArH), 5.22 (2 H, s, OCH$_2$Ar), 4.93 (1 H, dd, J 7.4,4.0 Hz, CHαthiopro), 4.86 (1 H, d, J 9.2 Hz, NCH$_A$H$_B$S),4.55 (1 H, dt,CHαtyr), 4.44 (1 H, d, J 9.3 Hz, NCH$_A$H$_B$S), 3.73 (2 H, m, COCH$_2$Py) and 3.09–2.94 (4 H, m, 2×CHCH$_2$) (acid proton not observed at 400K); m/z (ESI) 608 (MH+).

e) N-Acetyl-D-thioproline-4-(2,6-dichlorophenylacetylene)-L-phenylalanine
from Intermediate 39 as a white solid. δH (DMSO-d$^6$, 390K) 7.83 (1 H, br d, CONH), 7.55–7.48 (3 H, m, ArH+Cl$_2$ArH), 7.40 (1 H,dd, J 8.9, 7.3 Hz, Cl$_2$ArH), 7.32 (2 H, d, J 8.3 Hz, ArH), 4.83 (1 H, dd, J 7.3, 3.9 Hz, CHαthiopro), 4.77 (1 H, d, J 9.2 Hz, NCH$_A$H$_B$S), 4.57 (1 H,dt, J 8.4, 5.3 Hz, CHαPh), 4.38 ((1 H, d, J 9.1 Hz, NCH$_A$H$_B$S), 3.26 (1 H, dd, J 11.5, 7.4 Hz, CHCH$_A$H$_B$S), 3.20 (1 H, dd, J 14.1, 5.3 Hz, CHCH$_A$H$_B$Ar), 3.08–2.99 (2 H, m, CHCH$_A$H$_B$S+ CHCH$_A$H$_B$Ar) and 1.99 (3 H, s, COCH$_3$) (acid proton not observed at 390K); m/z (ESI, 15 V 491 (MH+).

f) N-Acetyl-D-thioproline-4-(N'-thioacetyl)amino-L-phenylaianine
from intermediate 31: δH (DMSO-d$^6$) (2 rotamers observed) 11.50 (1 H, s, CO$_2$H), 8.46 (d, J 8.3 Hz) and 8.19 (d, J 8.3 Hz) together (NH), 7.68 (2 H, d, J 8.5 Hz,ArH), 7.21 (2 H, dd, J 8.5, 8.5 Hz, ArH), 4.85–4.69 (2 H, m, NCH$_2$S), 4.53–4.19 (2 H, m, 2×αCH), 3.31–2.71 (4 H, m, CH$_2$Ar and SCH$_2$CH), 2.58 (3 H, s,CSCH$_3$) and 2.05 (s) and 1.82 (s) together (3 H, COCH$_3$); m/z (ESI, 60 V) 396 (MH+).

g) N-Acetyl-D-thioproline-4-(N'-thiobenzoyl)amino-L-phenylalanine
from the corresponding methyl ester prepared in a similar manner to Intermediate 31: δH (DMSO-d$^6$) 8.50 (d, J 8.1 Hz) and 8.22 (d, J 8.4 Hz) together (1 H,NH), 7.85–7.72 (4 H,m, ArH), 7.56–7.48 (3 H, m, ArH), 7.32–7.18 (2 H, m, ArH), 4.80–4.65 (2 H, m, NCH$_2$S), 4.52–4.20 (2 H, m, 2×CHα), 3.24–2.73 (4 H, m, CH$_2$Ar and SCH$_2$CH) and 2.06 (s) and 1.85 (s) together (3 H, COCH$_3$); m/z (ESI, 60 V) 458 (MH+).

h) N-Acetyl-D-thioproline-4-(t-butylureido)-L-phenylalanine
from Intermediate 64: δH (DMSO-d$^6$) 8.42–8.05 (2 H, m,2×NiH), 7.28-6.99 (4 H, m, ArH), 5.92 (1 H, s,NiH), 4.83–4.18 (4 H, m, NCH$_2$S and 2×α-CH), 3.22–2.21 (4 H, m, CH$_2$Ar and SCH$_2$CH) 2.0 (s) and 1.84 (s); together (3 H, COCH$_3$) and 1.27 (9 H, s, C(CH$_3$)$_3$); m/z (ESI, 60 V) 437 (MH+).

i) N Acetyl-D-thioproline-4-(isopropylureido)-L-phenylaIanine
from Intermediate 65: δl H (DMSO d$^6$) 8.39 (d, J 8.1 Hz) and 8.10 (d, J 8.1 Hz) together (1 H, NH), 8.18 (1 H, s,NH),7.31–7.20 (2 H, m, ArH), 7.10–6.98 (2 H, m, ArH), 5.92 (1 H, d, J 7.5 Hz, NH), 4.83–4.20 (4 H, m, NCH$_2$S and 2×CHα), 3.82–3.68 (1 H, m, CH(CH$_3$)$_2$), 3.22, 2.72 (4 H, m, C$_2$Ar and SCH$_2$CH), 2.05 (s) and 1.84 (s) together (3 H, COCH$_3$) and 1.08 (6 H, d, J 6.5 Hz, CH(CH$_3$)$_2$); m/z (ESI, 60 V) 423 (MH+).

j) N-Acetyl-D-thioproline-4-(methylthioureido)-L-phenylaianine
from Intermediate 63: δH (DMSO-d$^6$) 9.48 (1 H, br s, NH), 8.48 (d, J 8.3 Hz) and 8.11 (d, J 8.3 Hz) together (1 H, NH), 7.60 (1 H, br s, NH), 7.35–7.10 (4 H, m, ArH), 4.82–4.18 (4 H, m, NCH$_2$S and 2×α-CH), 3.40–2.75 (7 H, m, CH$_2$Ar, SCH$_2$CH and CSNHCH$_3$) and 2.05 (s) and 1.83 (s) together (3 H, COCH$_3$); m/z (ESI, 60 V) 411 (MH+).

k) N-Acetyl-D-thioproline-(O-3,5-dichloroisonicotinoyl)-L-tyrosine from Intermediate 60: δH (DMSO-d$^6$, 400K) 8.63 (2 H, s, pyr-H), 7.55 (1 H, br s, NH), 7.16 (2 H, AB d, J 8.7 Hz, Ar—H), 6.93 (2 H, AB d, J 8.7 Hz, Ar—H), 5.26 (2 H, s, CH$_2$O), 4.80 (1 H, m, CHα-thiopro), 4.77 (1 H, d, J 9.2 Hz, NCH$_A$H$_B$S), 4.41 (1 H, m, CHα-Tyr), 4.36 (1 H, d, J 9.2 Hz, NCH$_A$H$_B$S), 3.23 (1 H, dd, J 11.4, 7.4 Hz, CHCH$_A$H$_B$S), 3.14–2.91 (3 H, m, CHCH$_A$H$_B$S+CHCH$_2$Ar) and 1.97 (3 H, s, COMe). m/z (ESI, 60 V) 498 (MH+).

l) N-Acetyl-D-thioproline-4-(N'-isobutyloxycarbonyl)amino-L-phenylalanine from Intermediate 62: δH (DMSO-d$^6$) 9.50 (1 H, s, NH), 8.41 (d, J 8.0 Hz) and 8.11 (d, J 8.1 Hz; together (1 H, NH), 7.39–7.29 (2 H, m, ArH), 7.15–7.03 (2 H, m, ArH), 4.83–4.19 (4 H, m, NCH$_2$S and 2×α-CH), 3.85 (2 H, d, J 6.7 Hz, OCH$_2$), 3.22–2.70 (4 H, m, CH$_2$Ar and SCH$_2$CH), 2.05 (s) and 1.83 (s); together (3 H, COCH$_3$), 1.91 (1 H, quin. J 6.7 Hz, CH$_2$CH(CH$_3$)$_2$) and 0.92 (6 H, d, J 6.7 Hz, CH$_2$CH(CH$_3$)$_2$); m/z (ESI, 60 V) 438 (MH+).

EXAMPLE 3 a) N-(Pyrid-3-ylacetyl)-D-thioproline-(O-2,4,6-trichlorobenzoyl)-L-tyrosine

A solution of the methyl esters, Intermediate 11 (0.65 g, 1.0 mmol) in dioxane/MeOH (1:1, 40 ml) and water (20 ml) was treated with lithium hydroxide monohydrate (44 mg, 1.1 mmol). The reaction was stirred at room temperature for 1.5 h then glacial acetic acid was added to adjust the pH to 4.5. The solvent was removed in vacuo and the residue purified by chromatography [SiO$_2$; DCM (200), MeOH (20), ethanol (3) and water (2)], to give two products: the title compound (132 mg, 21%) and N-(pyrid-3-ylacetyl)-L-thioproline-(O-2,4,6-trichlorobenzoyl)-L-tyrosine (55 mg), 9%. (D-isomer) δH (DMSO-d$_6$, 390K) 8.42 (2 H, m, pyr-H), 7.89 (1 H, br s, NH), 7.77 (2 H, s, chloro-Ar—H), 7.61 (1 H, d, J 7.7 Hz, pyr-H), 7.35 (2 H, d, J 8.5 Hz, Ar—H), 7.28 (1 H, m, pyr-H), 7.18 (2 H, d, J 8.5 Hz, Ar—H), 4.93 (1 H, dd, J 4.0, 7.4 Hz, CHα-thio), 4.86 (1 H. d, J 9.2 Hz, NCH$_A$CH$_B$S), 4.57 (1 H, m, CHα-tyr), 4.46 (1 H, d, J 9.2 Hz, NC$_A$CH$_B$S), 3.72 (2 H, m, CH$_2$-pyr) and 3.31–2.99 (4 H, m). m/z (ESI, 15 V) 622, (MH+).

L-isomer (DMSO-d$_6$, 390K) 8.41 (1 H, m, pyr-H), 7.87 (1 H, br s, NH), 7.77 (2 H, s, chloro-Ar—H), 7.59 (1 H, d, J 7.8 Hz, pyr-H), 7.37 (2 H, d, J 8.6 Hz, Ar—H), 7.26 (1 H, dd, J 4.9, 7.8 Hz, pyr-H), 7.17 (2 H, d, J 8.6 Hz, Ar—H), 4.93 (1 H, dd, J 3.8, 7.4 Hz, CH$_α$ thiopro), 4.84 (1 H, d, J 9.2 Hz, NCH$_A$CH$_B$S), 4.61 (1 H, m, CH$_α$tyr), 4.45 (1 H, d, J 9.2 Hz, NCH$_A$CH$_B$S), 3.69 (2 H, m, CH$_2$-pyr) and 3.01–2.98 (4 H, m, Ar—CH$_2$ and CHCH$_2$S). m/z (ESI, 15 V) 622 (MH+).

The following compounds were prepared in a similar manner from the corresponding methyl ester. Each ester starting material was prepared from intermediate 10 and either 2,6-dimethoxybenzoyl chloride or 2,4-dimethoxybenzoyl chloride in a similar manner to Intermediate 11:

b) N-(Pyrid-3-acetyl)-L-thioproline-(O-2,6-dimethoxybenzoyl)-L-tyrosine

δH (DMSO-d$^6$, 390K) 8.43 (2 H, m, pyr-H), 7.77 (1 H, br s, NH), 7.60 (1 H, m, pyr-H), 7.40 (1 H, t, J 8.4 Hz Ar(OMe)$_2$H), 7.29 (3 H, m, Ar (OMe)$_2$H and pyr-H), 7.06 (2 H, ABd, J 8.5 Hz, Ar—H), 6.77 (2H, ABd, J 8.5 Hz, Ar—H), 4.95 (1 H, dd, J 7.4, 3.8 Hz, CHα-thio), 4.85 (1 H, d, J 9.3 Hz, NCH$_{AB}$S), 4.58 (1 H, m, CHα-tyr), 4.45 (1 H, d, J 9.3 Hz, NCH$_A$H$_B$S), 3.87 (6 H, s OMe), 3.72 (2 H, m, CH$_2$CO), 3.33 (1 H, dd, J 11.6, 7.4 Hz, CHCH$_A$H$_B$S), 3.18 (1 H, dd, J 14.2, 5.4 Hz, CH$_A$H$_B$Ar), 3.15 (1 H, dd, J 11.6, 3.8 Hz, CHCH$_A$H$_B$S) and 3.04 (1 H, dd, J 14.2, 8.0 Hz, CH$_A$H$_B$Ar). m/z (ES+, 70 V), 580 (MH+).

c) N-(Pyrid-3-acetyl)-D-thioproline-(O-2,4-dimethoxybenzoyl)-L-tyrosine

δH (DMSO-d$^6$, 390K) 8.43 (2 H, m, pyr-H), 7.83 (1 H, br s, NH), 7.62 (1 H, m, pyr-H), 7.41 (1 H, t, J 8.4 Hz, Ar(OMe)$_2$-H), 7.30 (3 H, m, Ar(OMe)$_2$-H, pyr-H), 7.09 (2 H, ABd, J 8.5Hz, Ar—H), 6.77 (2 H, ABd, J 8.5 Hz, Ar—H), 4.95 (1 H, dd, J 7.4, 4.0 Hz, CHα-Thiopro), 4.87 (1 H, d, J 9.2 Hz, NCH$_A$H$_B$S), 4.57 (1 H, m, CHα-tyr), 4.46 (1 H, d, J 9.2 Hz, NCH$_A$H$_B$S), 3.87 (6 H, s, OMe), 3.79–3.67 (2 H, m, CH$_2$O), 3.29 (1 H, dd, J 11.6, 7.4 Hz, CHCH$_A$H$_B$S), 3.06–3.00 (2 H, m, CHCH$_A$H$_B$S) and CHCH$_A$H$_B$Ar, m/z (ES+, 70 V), 580 (MH+).

EXAMPLE 4

N-Acetyl-D-thioproline-(O-pyrimidin-2-yl)-L-tyrosine

Lithium hydroxide (51 mg, 1.2 mmol) was added to a solution of Intermediate 14 (470 mg, 1.09 mmol) in a mixture of THF (10 ml) and water (10 ml). The mixture was stirred at room temperature for 30min, then the THF was evaporated in vacuo. The aqueous residue was acidified (1M, hydrochloric acid) and the precipitate obtained filtered off, washed with water and dried to give the title compound as a white powdery solid (269 mg, 59%). δH (DMSO-d$^6$, 400K) 8.60 (2 H, d, J 4.8 Hz, 2×HetArH), 7.74 ((1 H, br d, CONH), 7.26 (2 H, d, J 8.7 Hz, CH$_2$ArH), 7.20 (1 H, t, J 4.7 Hz, HetArH), 7.08 (2 H, d, J 8.7 Hz, CH$_2$ArH), 4.83 (1 H, dd, J 4.1, 7.3 Hz, CHαthiopro), 4.78 (1 H, d, J 9.2 Hz, NCH$_A$H$_B$S), 4.57 (1 H, dt, J 5.4, 8.3 Hz, CHαtyr), 4.38 (1 H, d, J 9.2 Hz, NCH$_A$H$_B$S), 3.25 (1 H, dd, J 7.4, 11.6 Hz, CHCH$_A$H$_B$S), 3.18 (1 H, dd, J 5.4, 14.1 Hz, CH$_A$H$_B$Ar), 3.04–2.97 (2 H, m, CHCH$_A$H$_B$S+CH$_A$H$_B$Ar) and 2.00 (3 H, s, CH$_3$CO); m/z (ESI, 27 V) 417 (MH+).

EXAMPLE 5

N-(Pyrid-3-ylacetyl)-D-thioproline-(O-2,6-dichlorobenzoyl)-L-tyrosine

Lithium hydroxide monohydrate (6 mg, 0.14 mmol) was added to an ice-bath cooled solution of Intermediate 15 (100 mg, 0.17 mmol) in dioxane (4 ml), methanol (2 ml), and water (3 ml). The cooling bath was removed and the reaction mixture stirred at room temperature for 1 h. The pH was made slightly acidic by addition of two drops of acetic acid and the solvent removed in vacuo. The obtained solid was chromatographed [SiO$_2$; DCM (002), MeOH (2), ethanol (3), H$_2$O (2)] which yielded a colourless oil. This was dissolved in a small volume of methanol, diluted with water, and freeze-dried to afford the title compound as a white amorphous solid (60 mg, 68%): δH (DMSO-d$^6$, 400K), 8.45–8.40 (2 H, m, pyrH), 7.83 (1 H, br s, NH), 7.63–7.52 (4 H, m, Ar(Cl)H and pyrH), 7.34 (2 H, d, J 8.6 Hz, ArH), 7.26 (2 H, dd, J 4.7, 7.7 Hz, pyrH), 7.17 (1 H, d, J 8.6 Hz, ArH), 4.94 (1 H, dd, J 7.4, 4 Hz, CHαthiopro), 4.86 (1 H, d, J 9.2 Hz, NCH$_A$H$_B$S), 4.58–4.49 (1 H, m, CHαtyr), 4.45 (1 H, d, J 9.2 Hz, NCH$_A$H$_B$S), 3.76 (1 H, d, J 16 Hz, CH$_A$H$_B$pyr), 3.66 (1 H, d, J 16 Hz, NCH$_A$H$_B$pyr), 3.28 (1 H, dd, J 7.4, 11.6 Hz, CHCH$_A$H$_B$S), 3.20 (1 H, dd, J 5.5, 14 Hz, CH$_A$H$_B$Ar), 3.08–3.01 (2 H, m, CHCH$_A$H$_B$S and CH$_A$H$_B$ar); m/z (ESI, 27 V) 588 (MH+).

EXAMPLE 6

N-Acetyl-D-thioproline-(N'-2,6-dichlorobenzoyl)-L-4-aminophenyl-alanine

Intermediate 16 (165 mg, 0.31 mmol) was treated with a solution of lithium hydroxide monohydrate (16 mg, 0.38 mmol) in dioxane (2 ml), MeOH(2 ml), and water (3 ml) for 3 h at room temperature. The pH was made slightly acidic with a few drops of acetic acid and the solvent removed in vacuo. The residue was treated with water and the obtained solid was collected by filtration with further water washing. The title compound was isolated as a white powder (120 mg, 75%) after drying in vacuo (50°, overnight): δH (DMSO-d$^6$, 400K), 10.13 (1 H, br s, ArNHCO), 7.69 (1 H, br d J ~8 Hz, NHCO), 7.52 (1 H, br d, J ~8 Hz), 7.52–7.41 (3 H, m, Ar(Cl)H), 7.19 (1 H, d, J 8.4 Hz, ArH), 4.84 (1 H, dd, J 3.9, 7.4 Hz, CHα-thiopro), 4.77 (1 H, d, J 9.2 Hz, NCH$_A$H$_B$S), 4.54 (1 H, ddd, J 5.5, 8.1, 8.2Hz, CHα-tyr), 4.38 (1 H, d, J 9.2 Hz, NCH$_A$H$_B$S), 3.25 (1 H, dd, J 7.4, 11.5 HzCHCH$_A$H$_B$S), 3.12 (1 H, dd, J 5.5, 14.1 Hz, CH$_A$H$_B$Ar), 3.01 (1 H, dd, J 3.9, 11.5 Hz, CHCH$_A$H$_B$S), 2.97 (1 H, dd, J 8.2, 14.1 Hz, CH$_A$H$_B$Ar) and 1.99 (3 H, s, COCH$_3$); m/z (ESI, 27 V) 510 (MH+).

EXAMPLE 7

N-(Pyrid-3-ylacetyl)-D-thioproline-(O-benzyl)-L-tyrosine

Intermediate 19 (190 mg, 0.37 mmol) was treated with a solution of lithium hydroxide monohydrate (19 mg, 0.54 mmol) in dioxane (2 ml), MeOH (2 ml) and water (2 ml) at room temperature for 2.5 h. The pH was made slightly acidic by addition of a few drops of acetic acid and the solvent removed in vacuo. The obtained solid was treated with water and collected by filtration with further water washing. After drying in vacuo (50°, overnight) the title compound was obtained as a white amorphous solid (105 mg, 57%). δH (DMSO-d$^6$, 400K), 8.46–8.40 (2 H, m, pyr H), 7.75 (1 H, br d, J 6.0 Hz, NH), 7.61 (1 H. d, J 7.9 Hz, pyrH), 7.44–7.27 (6 H, m, ArH and pyrH), 7.13 (2 H, d, J 8.6 Hz, ArH), 6.89 (2 H, d, J 8.6 Hz, ArH), 5.06 (2 H, s, CH$_2$O), 4.92 (1 H, dd, J 7.4, 4.0 Hz, CH$_α$thiopro), 4.86 (1 H, d, J 9.2 Hz, NCH$_A$H$_B$S), 4.53 (1 H, ddd, 1 8.3, 8.1, 5.5 Hz, CH$_α$tyr), 4.43 (1 H, d, J 9.2 Hz, NCH$_A$H$_B$S), 3.75 (1 H, d, J 16.1 Hz, CH$_A$H$_B$pyr), 3.66 (1 H, d, J 16.1 Hz, CH$_A$H$_B$pyr), 3.27 (1 H, dd, J 11.6, 7.4 Hz, CHCH$_A$H$_B$S), 3.12–2.88 (3 H, m, CHCH$_A$H$_B$S and (CH$_2$Ar); m/z (ESI), 506 (MH+).

EXAMPLE 8

N-Acetyl-D-thioproline-(N'-3,5-dichlorobenzoyl)-L-4-aminophenylalanine

Intermediate 5 was reacted with 3,5-dichlorobenzoyl chloride in a similar manner to that described for Intermediate 16. Subsequent hydrolysis as described for the compound of Example 2, afforded the title compound as a white powder (925 mg). δH (DMSO-d$^6$) (1:1 mixture of rotamers) 10.36 (1 H, s), 8.44 and 8.13 (1 H, d, J 7.0 Hz), 7.97 (2 H, d, J 1.9 Hz), 7.85 (1 H, t, J 1.9 Hz), 7.65 (2 H, app.d, J 7.0 Hz), 7.20 (2 H, app.t, J 9.0 Hz), 4.82–4.75 (1 H, m), 4.73 (H, app.t, J 8.4 Hz), 4.50–4.36 (1 H, m), 4.46 (0.5 H, d, J 8.9 Hz), 4.25 (0.5 H, d, J 8.9 Hz), 3.30–2.85 (4 H, m's), 2.06 and 1.85 (3 H, s); m/z (ESI, 60 V) 510 (MH+).

EXAMPLE 9

N-Acetyl-D-thioproline-[N'-2-fluoro-6-(trifluoromethyl)benzoyl]-L-4-aminophenylalanine Intermediate 5 was reacted with 2-fluoro-6-(trifluoromethyl)benzoyl chloride in a similar manner to that described for Intermediate 16. Subsequent hydroylsis as described for the compound of Example 2, afforded the title compound as a white powder (650 mg). δH (DMSO-d$^6$, 400K), 10.18 (1 H, s), 7.75–7.53 (4 H,m), 7.51 (2 H, d, J 8.4 Hz), 7.19 (2H, d, J 8.4 Hz), 4.83 (1 H, dd, J 7.3, 3.9 Hz), 4.77 (1 H, d, J 9.2 Hz), 4.57–4.50 (1 H, m), 4.38 (1 H, d, J 9.2 Hz), 3.25 (1 H, dd, J 11.6, 7.4 Hz), 3.12 (1 H, dd, J 14.1, 5.3 Hz), 3.04 (1 H, dd, J 11.6, 3.9 Hz), 2.98 (1 H, dd, J 14.1, 8.1 Hz) and 1.99 (3 H, s); m/z (ESI, 60 V) 528 (MH+).

EXAMPLE 10

N-Acetyl-D-thioproline-(N'-2,4,6-trichlorobenzoyl)-L-4-aminophenylalanine

Intermediate 5 was reacted with 2,4,6-trichlorobenzoyl chloride in a similar manner to that described for Intermediate 16. Subsequent hydrolysis, as described for the compound of Example 2, afforded the title compound as a white powder (950 mg). δH (DMSO-d$^6$, 1:1 mixtures of rotamers), 10.68 (1 H,s ), 8.46 and 8.15 (1 H, d, J 8.0 Hz), 7.82 (2 H, s), 7.55 (2 H, approximate d, J 7.0 Hz), 7.19 (2 H, approximate t, J 9.0 Hz), 4.80–4.68 (2 H, m), 4.46 (1 H, d, J 9.0 Hz), 4.46–4.35 (1 H,m), 4.23 (1 H, d, J 9.0 Hz), 3.35–2.76 (4 H, m), 2.05 and 1.84 (3 H, s); m/z (ESI, 60 V) 544 (MH+).

EXAMPLE 11

N-Acetyl-D-thioproline-(N'-2,6-dichlorobenzyl)-L-4-aminophenyl alanine

Intermediate 21 was hydrolysed and purified in a similar manner to that described for the compound of Example 5. Freeze-drying afforded the title compound as a white amorphous solid (206 mg). δH (DMSO-d6, 390K), 7.62 (1 H, br d, J 7.0 Hz), 7.44 (2 H, app.d, J 7.0 Hz), 7.32 (1 H, app.t, J 8.0 Hz), 6.95 (2 H, d, J 8.6 Hz), 6.66 (2 H, d, J 8.6 Hz), 4.81 (1 H, dd, J 7.4, 4.0 Hz), 4.76 (1 H, d, J 9.2 Hz), 4.47 (2 H, s), 4.46 (2 H, m), 4.36 (1 H, d, J 9.2 Hz),3.24 (1 H, dd, J 11.5, 7.4 Hz), 3.03–2.95 (2 H, m), 2.83 (1 H, dd, J 14.1, 8.1 Hz) and 1.98 (3 H, s); m/z (ESI, 30 V) 496 (MH+).

EXAMPLE 12

N-Acetyl-D-thioproline-(N'-acetyl-N'-2,6-dichlorobenzyl)-L-4-aminophenylalanine Intermediate 21 was N-acetylated with acetic anhydride in DCM and subsequently hydrolysed and purified in a similar manner to that described for the compound of Example 5. Freeze-drying afforded the title compound as a white amorphous powder (120 mg). δH (DMSO-d$^6$, 390K), 7.71 (1 H, br d, J 8.0 Hz), 7.28 (2 H, app.d J 7.0 Hz), 7.22 (2 H, app.t, J 7.0 Hz), 7.15 (2 H, d, J 8.3 Hz), 6.94 (2 H, d, J 8.3 Hz), 5.18 (2 H, s), 4.79–4.75 (1 H, m), 4.77 (1 H, d, J 9.2 Hz), 4.45 (1 H, sym.m), 4.33 (1 H, d, J 9.2 Hz), 3.21 (1 H, dd, J 11.4, 7.3 Hz), 3.09 (1 H, dd, J 14.1, 5.1 Hz), 2.95–2.86 (2 H, m) 1.97 (3 H, s) and 1.75 (3 H, s); m/z (ESI, 30 V) 538 (MH+).

EXAMPLE 13

N-Acetyl-D-thioproline-(N'-2,4,6-trichlorobenzyl)-L-4-aminophenylalanine.

Intermediate 5 was reacted with 2,4,6-trichlorobenzyl bromide in a similar manner to that described for Intermediate 21. Subsequent hydrolysis and purification as described for the compound of Example 5, followed by freeze drying afforded the title compound as a white amorphous solid (265 mg). δH (DMSO-d⁶, 1:1 ratio of rotamers) 8.33 (0.5 H, d, J 8.0 Hz), 8.04 (0.5 H, d, J 8.0 Hz), 7.69 (2 H, s), 6.93 (2 H, app.t, J 8.0 Hz), 6.57 (2 H, app.d, J 8.0 Hz), 5.62 (1 H, br s), 4.82–4.68 (2 H, m), 4.45 (0.5 H, d, J 8.7 Hz), 4.43–4.30 (1 H, m), 4.31 (2 H, s), 4.22 (0.5 H, d, J 9.6 Hz), 3.29 (0.5 H, dd, J 11.7, 7.3 Hz), 3.12 (0.5 H, dd, J 11.4, 7.3 Hz), 3.00–2.69 (3 H, m), 2.05 (1.5 H, s) and 1.84 (1.5 H, s); m/z (ESI, 60 V) 530 (MH+).

EXAMPLE 14

N-Acetyl-D-thioproline-(N'-2,6-dichlorobenzenesulphonyl)-L-4-aminophenylalanine Intermediate 5 was reacted with 2,6-dichlorobenzenesulphonyl chloride in a similar manner to that described for Intermediate 2. The crude product was chromatographed (silica; EtOAc) to purity then hydrolysed with aqueous LIOH (as described for the compound of Example 5). Chromatography [silica; DCM (200), (MeOH (20), AcOH (3), H$_2$O (2)] and freeze-drying afforded the title compound as a white amorphous solid (270 mg). δH (DMSO-d⁶, 400K) 7.62 (1 H, br d, J 8.0 Hz), 7.54 (2 H, app.d, J 7.7 Hz), 7.47 (1 H, app.t, J 7.7 Hz), 7.08 (2 H, d, J 8.9 Hz), 7.03 (2 H, d, J 8.9 Hz), 4.80–4.73 (1 H, m), 4.74 (1 H, d, J 9.2 Hz), 4.47 (1 H, m), 4.33 (1 H, d, J 9.2 Hz), 3.18 (1 H, dd, J 11.5, 7.4 Hz), 3.05 (1 H, dd, J 14.2, 5.3 Hz), 2.96–2.84 (2 H, m) and 1.95 (3 H, s); m/z (ESI, 60 V) 546 (MH+).

EXAMPLE 15

N-Acetyl-D-thioproline-4-(2-methoxyphenylureido)-L-phenylalanine

A solution of Intermediate 5 (500 mg, 1.42 mmol) and 2-methoxyphenyl isocyanate (233 mg, 208 l, 1.56 mmol) in dry DCM (10 ml) was stirred under N$_2$ at room temperature for 2 h. The volatiles were removed in vacuo and the residue suspended in Et$_2$O. The obtained solid was filtered off with 10% aqueous HCl and Et$_2$O washing and sucked dry. This intermediate (560 mg, 1.12 mmol) was treated with LiOH.H$_2$O (56 mg, 1.33 mmol) in dioxan (5 ml), methanol (3 ml) and water (5 ml) at room temperature for 2 h. A few drops of AcOH were added and the volatiles removed in vacuo. The residue was treated with Et$_2$O and water and filtered off with water washing to afford the title compound as an off-white powder (325 mg). 8H (DMSO-d⁶, a 1:1 ratio of rotameric species) 9.28 (1 H, s), 8.31 and 8.02 (1 H, d, J 7.8 Hz), 8.21 (1 H, s), 8.11 (1 H, d, J 7.6 Hz), 7.40–7.28 (2 H, m), 7.18–7.03 (2 H, m), 7.02–6.86 (3 H, m), 4.86–4.70 (2 H, m), 4.46 (0.5 H, d, J 8.8 Hz), 4.43–4.31 (1 H, m), 4.22 (0.5 H, d, J 9.4 Hz), 3.86 (3 H, s), 3.37–2.78 (4 H, m), 2.05 and 1.84 (3 H, s); m/z (ESI, 60 V) 487 (MH+).

EXAMPLE 16 a) N-(Pyrid-4-oyl)-D-thioproline-(O-benzyl)-L-tyrosine

Intermediate 18 was coupled to isonicotinic acid in a similar manner to that described for Intermediate 19, and subsequently hydrolysed with aqueous LiOH in a similar manner to that described for the compound of Example 2a) to afford the title compound as a white solid (175 mg). δH (DMSO-d⁶, 400K), 8.65 (2 H, d, J 6.1 Hz), 7.78 (1 H, d, J 8.0 Hz), 7.45–7.25 (5 H, m), 5.35 (2 H, d, J 6.1 Hz), 7.13 (2 H, d, J 8.6 Hz), 6.90 (2 H, d, J 8.6 Hz), 5.06 (2 H, s), 4.86–4.73 (1 H, m), 4.73 (1 H, d, J 9.5 Hz), 4.56–4.48 (1 H, m), 4.46 (1 H, d, J 9.4 Hz), 3.29 (1 H, dd, J 11.8, 7.4 Hz) and 3.12–2.86 (3 H, ms); m/z (ESI, 60 V) 492 (MH+).

The following compounds of Examples 16 b)–g) were prepared in a similar manner from Intermediate 18 and the appropriate acid:

b) N-(Pyrid-2-acetyl)-D-thioproline-(O-benzyl)-L-tyrosine

δH (DMSO-d⁶) 8.45 (2 H, d, J 4.8 Hz), 7.72–7.67 (2 H,m), 7.42–7.19 (7 H, m), 7.12 (2 H, d, J 8.5 Hz), 6.88 (2 H, d, J 8.5 Hz), 5.05 (2 H, s, CH$_2$O), 5.02–4.96 (1 H, m, CHα-thiopro), 4.87 (1 H, d, J 9.0 Hz, NCH$_A$H$_B$S), 4.57–4.51 (1 H, m, CHα-tyr), 4.39 (1 H, d, J 9.0 Hz, NCH$_A$H$_B$S), 3.85 (2 H, M, CH$_2$pyr, 3.26–3.20 (1 H, m, CHCH$_A$H$_B$S), 3.09–3.03 (2 H, m, CHCH$_A$H$_B$S+CH$_A$H$_B$Ar) amd 2.94–2.86 (1 H, m, CH$_A$H$_B$Ar). m/z (ESI, 27 V) 506 (MH+).

c) N-(Pyrid-4-acetyl)-D-thioproline-(O-benzyl)-L-tyrosine

δH (DMSO-d⁶) 8.46 (2 H, dd), 7.77 (1 H, br s), 7.43–7.29 (5 H,m), 7.20 (2 H, d), 7.13 (2 H, d), 6.90 (2 H, d), 5.05 (2 H, s, CH$_2$O), 4.92–4.88 (1 H,m), 4.42 (1 H,d), 3.78–3.68 (2 H, m), 3.28–3.22 (1 H, m) and 3.09–2.87 (4 H, m). m/z (ESI, 60 V), 506 (MH+).

d) N-(Indolyl-3-acetyl)-D-thioproline-(O-benzyl)-L-tyrosine

δH (DMSO-d⁶, 400K) 10.51 (1 H, br s, NH), 7.72 (1 H, br d), 7.54 (1 H, d, J 7.9 Hz), 7.36 (6 H, m), 7.18 (1 H, d, J 2.3 Hz), 7.11 (2 H, d, J 8.6 Hz), 7.07 (1 H, m), 6.97 (1 H,m), 6.89 (2 H, d, J 8.6 Hz), 5.05 (2 H, s, CH$_2$O), 4.95 (1 H, dd, J 7.4, 4.0 Hz, CHα-thiopro), 4.87 (1 H, d, J 9.2 Hz, NCH$_A$H$_B$S), 4.51 (1 H, m, CHα-tyr), 4.43 (1 H, d, J 9.2 Hz,NCH$_A$H$_B$S), 3.24 (2 H, d, J 8.2 Hz, CHCH$_2$Ar), 3.19 (2 H, dd, J 11.5, 7.4 Hz, CHCH$_2$S) and 2.99 (2 H, m, CH$_2$CO). m/z (ESI, 60 V) 544 (MH+).

e) N-(Benzothiophenyl-3-acetyl)-D-thioproline-(O-benzyl)-L-tyrosine

δH (DMSO-d⁶, 390K) 7.92 (1 H, m), 7.80 (2 H, m),7.48 (1 H, s), 7.37 (6H, m), 7.13 (2 H, d, J 8.6 Hz, Ar—H), 6.89 (2 H, d, J 8.6 Hz, Ar—H), 5.04 (2 H, s, CH$_2$O), 4.97 (1 H, dd, J 7.4, 4.0 Hz, CHα-thiopro), 4.88 (1 H, d, J 9.2 Hz, NCH$_A$H$_B$S), 4.52 (1 H, m, CHα-tyr), 4.48 (1 H, d, J 9.2 Hz, NCH$_A$H$_B$S), 3.94 (2 H, m, CHCH$_2$Ar), 3.27 (1 H, dd, J 11.5, 7.4 Hz, CH$_A$H$_B$S) and 3.03 (3 H, m, CH$_A$H$_B$S and CH$_2$CO). m/z (ESI, 60 V) 561 (MH+).

f) N-(Pyrid-3-propionyl)-D-thioproline-(O-benzyl)-L-tyrosine

δH (DMSO-d⁶) 8.46 (1 H, d, 8.37 (1 H, d, J 3.4 Hz), 7.60 (1 H, d, J 7.8 Hz), 7.71 (1 H, d, NH), 7.42–7.21 (6 H,m), 7.12 (2 H, d, J 8.6 Hz), 6.89 (2 H, d, J 8.6 Hz), 5.06 (2 H, s, CH$_2$O), 4.88–4.74 (1 H, m, CHα-thiopro), 4,79 (1 H, d, J 9.2 Hz, NCH$_A$H$_B$S), 4.52 (1 H, m, CHα-Tyr), 4.38 (1 H, d, J 9.2 Hz, NCH$_A$H$_B$S), 3.24–3.17 (1 H, m), 3.10–2.85 (5 H, m) and 2.68 (2 H, m). m/z (ESI, 60 V) 520 (MH+).

g) N-(Thiophen-3-acetyl)-D-thioproline-(O-benzyl)-L-tyrosine

δH (DMSO-d⁶) 7.74 (1 H, d), 7.44–7.22 (6 H, m), 7.21 (1 H, d, J 1.1 Hz), 7.15–7.10 (2 H, m), 7.01–6.99 (1 H, m), 6.92–6.88 (2 H, m), 5.06 92 H, s, CH$_2$O), 4.91 (1 H, m, CHα-Thiopro), 4.88 (1 H, d, J 9.2 Hz, NCH$_A$H$_B$S), 4.55–4.47 (1 H, m, CHα-tyr), 4.39 (1 H, d, J 9.2 Hz, NCH$_A$H$_B$S), 3.75–3.60 (2 H, m), 3.25–3.19 (1 H, m) and 3.11–2.87 (3 H, m). m/z (ESI, 60 V) 511 (MH+).

EXAMPLE 17

N-(4-Imidazoleacetyl)-D-thioproline-(O-2,6-dichlorobenzyl)-L-tyrosine

D-Thioproline-(O-2,6-dichlorobenzyl)-L-tyrosine methyl ester (prepared in a similar manner to Intermediate 18) was coupled to 1-trityl-4-imidazoleacetic acid in a similar manner to that described for Intermediate 19. Subsequent trityl removal (triethylsilane, TFA, DCM) and hydrolysis (aqueous LiOH; as described for the compound of Example 7) afforded the title compound as a white powder (235 mg). δH (DMSO-d$^6$, 390K) 8.1 (1 H, very br s), 7.96 (1 H, br d, J 8.0 Hz), 7.52–7.48 (3 H, m), 7.46–7.40 (2 H, m), 7.15 (2 H, d, J 8.4 Hz), 6.94 (2 H, d, J 8.4 Hz), 6.89 (2 H,s), 5.25 (2 H, s), 5.01 (1 H, dd, J 7.3, 3.7 Hz), 4.86 (1 H, d, J 9.0 Hz), 4.58–4.47 (1 H, m), 4.38 (1 H, d, J 9.0 Hz), 3.69 (1 H, d, J 15.7 Hz), 3.56 (1 H, d, J 15.7 Hz), 3.20 (1 H, dd, J 11.4, 7.3 Hz), 3.11–2.99 (2 H, m) and 2.91 (1 H, dd, J 14.0, 8.4 Hz); m/z (ESI, 60 V) 561 (MH+).

EXAMPLE 18

N-(Pyrid-3-oyl)-D-thioproline-(O-benzyl)-L-tyrosine

Intermediate 18 was coupled to nicotinic acid in a similar manner to that described for Intermediate 19, and subsequently hydrolysed with aqueous LiOH, as described for the compound of Example 7, to afford the title compound. δH (DMSO-d$^6$) 8.78–8.55 (2 H, br m), 8.38 (1 H, br d J 7.8 Hz), 8.21–7.25 (7 H, m), 7.11 (2 H, d, J 8.5 Hz), 6.85 (2 H, br d, J 8.0 Hz), 5.02 (2H, s), 5.03–4.3 (4 H, m), 3.40–3.22 (1 H, br m), 3.03 (1 H, dd, J 13.8, 4.6 Hz) and 2.90–2.75 (2 H, m); m/z (ESI), 492 (MH+).

EXAMPLE 19

N-Acetyl-D-thioproline-L-4-benzoylphenylalanine

Intermediate 20 (503mg, 1.14mmol) was treated with a solution of LiOH. H$_2$O (1.38 mmol) in 50% aqueous dioxane (20 ml) at room temperature for 2 h. The pH was adjusted to 3 with concentrated HCl and the volatiles removed in vacuo. The residue was chromatographed [silica; DCM (200), MeOH (20), AcOH (3), H$_2$O (2)] to afford the product as a colourless oil. Freeze-drying from aqueous methanol afforded the title compound as a white amorphous solid: δH (DMSO-d$^6$ approximately 1.6:1 ratio of rotameric species) 7.79–7.69(4 H, m), 7.68–7.61 (1 H, m), 7.58–7.48 (2 H, m), 7.45–7.36 (2 H, m), 4.85–4.68 (3 H, m), 4.57–4.42 (1 H, d, J 9.0 Hz), 3.48–3.08 (3 H, ms), 2.98 and 2.89 (1 H. dd, J 11.9, 4.0 Hz, 2.14 and 1.92 (3 H, s); m/z (ESI, 27 V) 427 (MH+).

EXAMPLE 20

N-(N-Acetyl-D—5,5-dimethyl-1,3-thiazolidin-4-oyl)-(O-benzyl)-L-tyrosine

Intermediate 22 (340 mg, 0.72 mmol) was treated with a solution of LiOH. H$_2$O (36 mg, 0.86 mmol) in MeOH (2 ml), dioxane (2 ml) and H$_2$O (3 ml) at room temperature for 1.5 h. A few drops of acetic acid were added and the volatiles were removed in vacuo. The crude product was chromatographed [silica; DCM (200), MeOH (20), AcOH (3), H$_2$O (2)] to afford the product as a colourless oil. Freeze-drying from aqueous methanol afforded the title compound as a white amorphous solid (240 mg, 73%). δH (DMSO-d$^6$, approximate 1.3:1 ratio of rotamers) 8.29 (1 H major, d, J 8.4 Hz), 8.06 (1 H minor, d, J 8.0 Hz), 7.44–7.28 (5 H, m), 7.20–7.10 (2 H, m), 6.93–6.85 (2 H, m), 5.07 (2 H major, s), 5.06 (2 H minor, s), 4.73 (1 H minor, d, J 8.7 Hz), 4.70 (1 H minor, d, J 8.7 Hz), 4.63 (1 H major d, J 9.8 Hz), 4.55 (1 H major, d, J 9.8 Hz), 4.50–4.24 (2 H, m's), 3.09 (1 H major, dd, J 13.9, 4.1 Hz), 2.96 (1 H minor, dd, J 13.9, 5.1 Hz), 2.85–2.75 (1 H, m), 2.03 (3 H minor, s), 1.81 (3 H major, s) and 1.35, 1.00 and 0.91 (6 H, singlets); m/z (ESI, 60 V) 457 (MH+).

EXAMPLE 21

N-Acetyl-D,L-homothioproline-(O-2,6-dichlorobenzyl)-L-tyrosine

N-Acetyl-D,L-homothioproline (prepared via (1) bromopyruvate, 2-aminoethanethiol hydrochloride, EtOH; (2) NaBH$_4$, EtOH; (3) acetic anhydride, DCM; (4) LiOH, aqueous EtOH) was coupled to O-(2,6-dichlorobenzyl)-L-tyrosine methyl ester hydrochloride in a similar manner to that described for Intermediate 19, affording the methyl ester of the title compound. Subsequent hydrolysis with aqueous LiOH and purification, similar to that described for the compound of Example 5, afforded the title compound as a white amorphous solid (850 mg). δH (DMSO-d$^6$, 390K, mixture of diastereoisomers ) 7.49 (2 H, approximate d, J 8.7 Hz), 7.45 (1 H, br s), 7.43 (1 H, approximate t, J 8.7 Hz), 7.19 and 7.17 (2 H, d, J 8.7 Hz), 6.95 and 6.94 (2 H, d, J 8.7 Hz), 5.25 (2 H, s), 5.02 (1 H, br m), 4.60–4.52 (1 H, m), 4.23–4.02 (1 H, br m), 3.45–2.92 (4 H, m), 2.81 and 2.77 (1 H, d, J 4.7 Hz) and 2.70–2.41 (2 H, m); m/z (ESI, 60 V) 511 (MH+).

EXAMPLE 22

N-(4-Morpholinoacetyl)-D-thioproline-(O-2,6-dichlorobenzyl)-L-tyrosine hydrochloride Intermediate 23 (618 mg, 1.04 mmol) was treated with LiOH.H$_2$O (96 mg, 2.29 mmol) in dioxane (10 ml), MeOH (5 ml) and water (5 ml) for 1.5 h at room temperature. A few drops of acetic acid were added and the volatiles removed in vacuo. The residue was chromatographed [silica; DCM (300 to 200), MeOH (20), AcOH (3), H$_2$O (2)] to afford the pure product as an oil. This was dissolved in aqueous dioxane, acidified with a few drops of concentrated HCl and evaporated in vacuo. The HCl salt was re-dissolved in water and freeze-dried to afford the title compound as a white amorphous solid (302 mg, 47%). δH (DMSO-d$^6$, 390K) 8.21 (1 H, br s), 7.50 (2 H, approximate t, J 8.0 Hz), 7.41 (1 H, approximate t. J 8.0 Hz), 7.19 (2 H, d, J8.6 Hz), 6.96 (2 H, d, J 8.6 Hz), 5.25 (2 H, s), 4.98 (1 H, dd, J 7.3, 4.3 Hz), 4.79 (1 H, d, J 9.2 Hz), 4.58–4.49 (1 H, m), 4.47 (1 H, d, J 9.2 Hz), 4.23–4.18 (1 H, m), 4.05–3.90 (1 H, m), 3.88 (4 H, t, J 4.7 Hz), 3.30 (1 H, dd, J 11.6, 7.4 Hz), 3.31–3.14 (4 H, br m), 3.11 (1 H, dd, J 14.2, 5.3 Hz), 3.00–2.92 (2 H, m); m/z (ES+, 60 V) 582 (MH+).

EXAMPLE 23

N-Acetyl-D-thioproline-(N'-2,6-dichlorobenzoyl-N'-methyl)-L-4-aminophenylalanine Intermediate 25 was reacted with 2,6-dichlorobenzoyl chloride in a similar manner to that described for Intermediate 2. Purification by flash chromatography (silica; 3:97 MeOH/DCM) and subsequent hydrolysis with aqueous LiOH (as described for the compound of Example 5) afforded the title compound as a white foam (750mg). δH (DMSO-d$^6$, (two pairs of rotameric species.) 8.50, 8.40, 8.22 and 8.16 (1 H, d, J 8.0 Hz), 7.62–7.08 (7 H, m), 4.82–4.30 (3 H, m), 4.45, 4.39, 4.21 and 4.17 (1 H, d, J 8.4 Hz), 3.34 and 3.10 (3 H, s), 3.30–2.50 (4 H, m), 2.05, 2.03, 1.83 and 1.79 (3 H, s); m/z (ES1, 30 V) 524 (MH+).

EXAMPLE 24

N-Acetyl-D-thioproline-(N'-2,6-dichlorobenzyl-N'-methyl)-L-4-aminophenylalanine

Intermediate 25 was reacted with 2,6-dichlorobenzyl bromide and purified in a similar manner to that described for Intermediate 21. Subsequent hydrolysis with aqueous LiOH (as described for the compound of Example 2a) afforded the title compound as an off-white solid (450 mg). 5 H (DMSO-d$^6$, 1:1 ratio of rotamers) 8.38 and 8.10 (1 H,d, J 8.3 Hz), 7.51 (2 H, d, J 7.9 Hz), 7.38 (1 H, t, J 7.9 Hz), 7.05 (2 H, app.t J 8.2 Hz), 6.84 (2 H, app. d, J 8.2 Hz), 4.82–4.68 (2 H, ms), 4.55 (2 H, s), 4.44 (0.5 H, d, J 9.2 Hz), 4.45–4.32 (1 H, m), 4.22 (0.5 H, d, J 9.8 Hz), 3.40–2.67 (4 H, m), 2.60 (3 H, s), 2.04 and 1.83 (3 H, s); m/z (ESI, 60 V) 510 (MH+).

EXAMPLE 25

N-Acetyl-D-thioproline-4-(carbobenzyloxy) phenylalanine

The title compound was prepared as a white solid by acylation of Intermediate 27 with N-acetyl-D-thioproline in a similar manner to the preparation of Intermediate 1 followed by hydrolysis of the resulting ester in a similar manner to the compound of Example 2a) using potassium carbonate in place of lithium hydroxide. δH (DMSO-$d^6$, 390K) 7.9 (2 H, dt, J 6.5, 1.8 Hz), 7.46–7.31 (7 H, m), 5.36 (2 H, s), 4.80 (1 H, m), 4.75 (d, J 9.1 Hz) and 4.73 (d, J 9.2 Hz) together (1 H), 4.59 (1 H, m), 4.41 (d, J, Hz) and 4.34 (d, J 9.2 Hz), together (1 H), 3.30–3.19 (2 H, m), 3.11–2.95 (2 H, m), 1.98 (s) and 1.97 (s) together (3 H); m/z (ESI. 60 V) 457 (MH+).

EXAMPLE 26

N-Acetyl-D-thioproline-(N'-benzenesulphonyl)-L-4-aminophenylalanine

A solution of Intermediate 61 (0.63 g, 1.37 mmol), in THF (20 ml) and water (10 ml) was treated with LiOH. $H_2O$ (69 mg, 1.65 mmol) and stirred at room temperature for 16 h. The reaction was acidified to pH1 with 10% HCl and extracted twice with DCM. The combined organic extracts were dried ($MgSO_4$) and evaporated in vacuo to give a foam that was purified by chromatography ($SiO_2$; DCM/MeOH/AcOH 90:10:1). The product was lyophilised from $CH_3CN$/water (3:2, 20 ml) to give the title compound as a fluffy white solid (0.25 g, 41%). δH (DMSO-$d^6$, 390K) 7.77–7.73 (2 H, m, Ar—H), 7.61 (1 H, br s, NH), 7.58–7.47 (3 H, m, Ar—H), 7.07 (2 H, d, J 8.7 Hz, Ar—H), 7.01 (2 H, d, J 8.7 Hz, Ar—H), 4.74 (1 H, m, CHα-Thiopro), 4.76 (1 H, d, J 9.2 Hz, NCH$_A$H$_B$S), 4.42 (1 H, dt, J 8.3, 5.3 Hz, CHα-Ph), 4.32 (1 H, d, J 9.2 Hz, NCH$_A$H$_B$S), 3.20 (1 H, dd, J 11.5, 7.4 Hz, CHCH$_A$H$_B$S), 3.04 (1 H, dd, J 14.1, 5.3 Hz, ArCH$_A$H$_B$), 2.94 (1 H, dd, J 11.5, 3.9 Hz, CHCH$_A$H$_B$S), 2.88 (1 H, dd, J 14.1, 8.5 Hz, ArCH$_A$H$_B$) and 1.95 (3 H, s, COMe). m/z (ESI, 30 V) 478 (MH+).

The following compounds of Examples 27–52 were prepared by acylation of an appropriate amine starting material (deprotected as necessary) using the acid indicated in a similar manner to the preparation of Intermediate 1 followed by hydrolysis of the resulting ester in a similar manner to the preparation of the compound of Example 2a):

EXAMPLE 27

N-(N-Acetyl-2-phenyl-D-1,3-thiazolidin-4-oyl)-(O-benzyl-L-tyrosine from Intermediate 53 and O-benzyl-L-tyrosine methyl hydrochloride ester δH (DMSO-$d^6$) 7.82 (1 H, br d, J 7.6 Hz, NH), 7.61 (2 H, m, Ar—H), 7.31 (8 H, m, Ar—H), 7.14 (2 H, d, J 8.7 Hz, Ar—H), 6.89 (2 H, d, J 8.7 Hz, Ar—H), 6.28 (1 H, s, NCH(Ph)S), 5.04 (2 H, s, CH$_2$O), 4.87 (1 H, t, J 6.9 Hz, CHα-thiopro), 4.59 (1 H, m, CHα-tyr), 3.24 (1 H, dd, J 11.8, 6.8 Hz, CHCH$_A$H$_B$S), 3.05 (2 H, m, CHCH$_A$H$_B$S and CHCH$_A$H$_B$Ar), 2.93 (1 H, dd, J 14.1, 8.3 Hz, CHCH$_A$H$_B$Ar) and 1.89 (3 H, s, COMe). m/z (ESI, 160 V) 505 (MH+).

EXAMPLE 28

N-(N-Acetyl-5-phenyl-1,3-thiazolidin-4-oyl-(O-2,6-dichlorobenzyl)-L-tyrosine

Prepared as 2-diastereomeric species, from Intermediate 55 and (O-2,6-dichlorobenzyl)-L-tyrosine methyl ester hydrochloride.

Diastereomer 1

δH (DMSO-$d^6$, 390K) 7.73 (1 H, br s, NH), 7.51–7.40 (3 H, m, Ar—H), 7.38–7.23 (5 H, m, Ar—H), 7.18 (2 H, d, J 8.7 Hz, Ar—H), 6.96 (2 H, d, J 8.7 Hz, Ar—H), 5.26 (2 H, s, CH$_2$O), 4.97 (1 H, d, J 9.2 Hz, NCH$_A$H$_B$S), 4.86 (1 H, m, CHα-thiopro), 4.76 (1 H, d, J 3.5 Hz, CH-Ph), 4.54 (1 H, m, CHα-tyr), 4.53 (1 H, d, J 9.2 Hz, NCH$_A$H$_B$S), 3.11 (1 H, dd, J 14.1, 5.3 Hz, CH$_A$H$_B$Ar), 2.96 (1 H, dd, J 14.1, 8.6 Hz, CH$_A$H$_B$Ar), 2.00 (3 H, br s, COMe). m/z (ESI, 60 V) 573 (MH+)

Diastereomer 2

δH (DMSO-$d^6$, 390K) 7.83 (1 H, br s, NH), 7.51–7.40 (3 H, m, Ar—H), 7.34–7.27 (5 H, m, Ar—H), 7.14 (2 H, d, J 8.7 Hz, Ar—H), 6.94 (2 H, d, J 8.7, Ar—H), 5.25 (2 H, s, CH$_2$O), 4.98 (1 H, d, J 9.0 Hz, NCH$_A$H$_B$S), 4.88 (1 H, m, CHα-thiopro), 4.68 (1 H, d, J 3.6 Hz, CH-Ph), 4.55 (2 H, m, CHα-tyr and NCH$_A$H$_B$S), 3.08 (1 H, dd, J 14.2, 5.3 Hz, CH$_A$H$_B$Ar), 2.93 (1 H, dd, J 14.2, 8.5 Hz, CH$_A$H$_B$Ar) and 2.01 (3 H, br s, COMe). m/z (ESI, 60 V) 573 (MH+).

EXAMPLE 29

N-Acetyl-(1-thia-3-azaspiro[4,4]non-4-oyl)-(O-2,6-dichlorobenzyl)-L-tyrosine

Prepared as 2 diastereomers [separated by fractional recrystalisation (ispropanol/water)] from Intermediate 57 and (O-2,6-dichlorobenzyl)-L-tyrosine methyl ester hydrochloride.

Diastereomer 1

δH (DMSO-$d^6$, 390K) 7.56 (1 H, br s, NH), 7.52–7.39 (3 H,m, Ar—H), 7.20 (2 H, d, J 8.7 Hz, Ar—H), 6.95 (2 H, d, J 8.7 Hz, Ar—H), 5.25 (2 H, s, CH$_2$O), 4.64 (2 H, s, NCH$_2$S), 4.61 (1 H, m, CHα-thiopro), 4.43 (1 H, m, CHα-tyr), 3.11 (1 H, dd, J 14.2, 5.2 Hz, CHCH$_A$H$_B$Ar), 2.94 (1 H, dd, J 14.2, 8.6 Hz, CHCH$_A$H$_B$Ar) and 1.92–1.45 (11 H, m, CH$_2$,COMe). m/z (ESI, 60 V) 551 (MH+).

Diastereomer 2

δH (DMSO-$d^6$, 400K) 7.51 (1 H, br s, NH), 7.48–7.39 (3 H, m, Ar—H), 7.17 (2 H, d, J 8.7, Ar—H), 6.95 (2 H, d, J 8.7 Hz, Ar—H), 5.26 (2 H, s, CH$_2$O), 4.69–4.45 (4 H, m, CHα-thiopro, CHα-tyr, NCH$_2$S), 3.10 (1 H, dd, J 14.2, 5.2 Hz, CH$_A$H$_B$Ar), 2.92 (1 H, dd, J 14.2, 8.7 Hz, CH$_A$H$_B$Ar), 1.96 (3 H, s, COMe), 1.95–1.54 (8 H, m, CH$_2$). m/z (ESI, 60 V) 551 (MH+).

EXAMPLE 30

N-(N-Acetyl-L-5,5-dimethyl-1,3-thiazolidin-4-oyl)-O-benzyl-L-tyrosine from Intermediate 42a) and O-benzyl-L-tyrosine methyl ester hydrochloride as a white solid. δH (DMSO-$d^6$, 400K) 7.58 (1 H, br d, CONH), 7.44–7.30 (5 H, m, Ph), 7.17 (2 H, d, J 8.7 Hz, ArH), 6.91 (2 H, d, J 8.7 Hz, ArH), 5.08 (2 H, s, OCH$_2$Ph), 4.73 (1 H, d, J9.2 Hz, NCH$_A$H$_B$S), 4.65 (1 H, d, J 9.1 Hz, NCH$_A$H$_B$S), 4.93 (1 H, dt, J 8.2, 5.5 CHα-tyr), 4.36 (1 H, s, CHα), 3.08 (1 H, dd, J 14.2, 5.4 Hz, CHCH$_A$H$_B$), 2.93 (1 H, dd, J 14.2, 8.2 Hz, CHCH$_A$H$_B$), 1.90 (3 H, br s, COCH$_3$), 1.50 (3 H, s, CMe$_A$Me$_B$) and 1.28 (3 H, s, CMe$_A$Me$_B$); m/z (ESI, 160 V) 457 (MH+).

EXAMPLE 31

N-(N-Acetyl-D-5,5-dimethyl-1,3-thiazolidin-4-oyl)-O-(2,6-dichlorobenzyl)-L-tyrosine from Intermediate 42b) and (O-2,6-dichlorobenzyl)-L-tyrosine methyl ester. δH (DMSO-$d^6$, 390K) 7.68 (1 H, br s, CONH), 7.51–7.48 (2 H, m, Cl$_2$ArH), 7.41 (1 H, dd, J 9.3, 6.5 Hz, Cl$_2$ArH), 7.18 (2 H, d, J 8.6 Hz, ArH), 6.95 (2 H, d, J 8.6 Hz, ArH), 5,26 (2 H, s, OCH$_2$Ar), 4.74 (1 H, d, J 9.2 Hz, NCH$_{AB}$S), 4.64 (1 H, d, J 9.3 Hz, NCH$_A$H$_B$S), 4.6 (1 H, br m, CHαtyr), 4.35 (1 H, s, CHα), 3.11 (1 H, dd, J 14.2, 5.3 Hz, CHCH$_A$H$_B$), 2.92 (1 H, dd, J 14.2, 8.7 Hz, CHCH$_A$H$_B$), 1.95 (3 H, s, COCH$_3$),1.45 (3 H, s, CMe$_A$Me$_B$) and 1.19 (3 H, s, CMe$_A$Me$_B$); m/z (ESI, 60 V) 525 (MH+).

EXAMPLE 32

N-Acetyl-D-thioproline-4[2-(1-phenylethyl)]-L-phenylalanine from Intermediate 41 and N-acetyl-D-thioproline. δH (DMSO-d$^6$, 400K) 7.66 (1 H, br d, CONH), 7.28–7.11 (9 H, m, ArH), 4.82 (1 H, dd, J 7.5, 3.8 Hz, CHαthiopro), 4.76 (1 H, d, J 9.2 Hz, NCH$_A$H$_B$S), 4.53 (1 H, dt, J 8.3, 5.4 Hz, CHαPh), 4.36 (1 H, d, J 9.2 Hz, NCH$_A$H$_B$S), 3.23 (1 H, d, CHCH$_A$H$_B$S), 3.11 (1 H, d, J 14.1, 5.4 Hz, CHCH$_A$H$_B$Ar), 3.00–2.93 (2 H, m, CHCH$_A$H$_B$S +CHCH$_A$H$_B$Ar), 2.90 (4 H, s, CH$_2$CH$_2$) and 1.98 (3 H, s COCH$_3$); m/z (ESI, 15 V) 427 (MH+).

EXAMPLE 33

N-Acetyl-D-thioproline-4-phenyl-L-phenylalanine from Intermediate 33 and N-acetyl-D-thioproline. δH (DMSO-d$^6$, 400K) 7.75 (1 H, br d, CONH), 7.62–7.29 (9 H, m, ArH), 4.83 (1 H, dd, J 7.2, 3.9 Hz. CHαthiopro), 7.76 (1 H, d, J 9.2 Hz, NCH$_A$H$_B$S), 4.59 (1 H, dt, J 8.4, 5.4 Hz, CHαPh), 4.37 (1 H, d, J 9.2 Hz, NCH$_A$H$_B$S), 3.28–3.16 (2 H, m, CHCH$_A$H$_B$S +CH$_A$H$_B$Ar), 3.06–2.98 (2 H, m, CHCH$_A$H$_B$S+CH$_A$H$_B$Ar) and 1.98 (3 H, s, COCH$_3$); m/z (ESI, 15 V) 399 (MH+).

EXAMPLE 34

N-Acetyl-D-thioproline-4-(3-prop-1-enyl)-L-phenylalanine from Intermediate 34 and N-acetyl-D-thioproline. δH (DMSO-d$^6$, 400K) 7.69 (1 H, br d, CONH), 7.14 (2 H, d, J 8.2 Hz, ArH), 7.09 (2 H, d, J 8.3 Hz, ArH), 6.04–5.90 (1 H,tdd, J 17.0, 10.2, 6.7 Hz, CH$_2$CH=CH$_2$), 5.10–5.03 (2 H, m, CH$_2$CH=CH$_2$), 4.81 (1 H, dd, J 7.5, 3.9 Hz, CHαthiopro), 4.76 (1 H, d, J 9.2 Hz, NCH$_A$H$_B$S), 4.53 (1 H, dt, J 8.3, 5.4 Hz, CHαPh), 4.36 (1 H, d, J 9.5 Hz, NCH$_A$H$_B$S), 3.34 (2 H, d, J 6.6 Hz, CH$_2$CH=CH$_2$), 3.23 (1 H, dd, J 11.5, 7.4 Hz, CHCH$_A$H$_B$S), 3.11 (1 H, dd, J 14.1, 5.5 Hz, CHCH$_A$H$_B$Ar), 3.00–2.91 (2 H, m, CHCH$_A$H$_B$S+ CHCH$_A$H$_B$Ar) and 1.97 (3 H, s, COCH$_3$); m/z (ESI, 15 V) 363 (MH+).

EXAMPLE 35

N-Acetyl-D-thioproline-4-(2-benzo[b]furanyl)-L-phenylalanine from Intermediate 35 and N-acetyl-D-thioproline. δH (DMSO-d$^6$, 400K) 7.80 (2 H, d, J 8.4 Hz, ArH), 7.75 (1 H, v br d, CONH), 7.65–7.55 (2 H, m ArH), 7.35 (2 H, d, J 8.5 Hz, ArH), 7.33–7.22 (3 H, m, ArH+C=CH), 4.84 (1 H, dd, J 7.4, 3.9 Hz, CHαthiopro), 4.76 (1 H, d, 1 9.2 Hz, NCH$_A$H$_B$S), 4.60 (1 H, dt, J 8.3, 5.4 Hz, CHαPh), 4.38 (1 H, d, J 9.1 Hz, NCH$_A$H$_B$S), 3.29–3.18 (2 H, m, 2×CHCH$_A$H$_B$), 3.09–3.01 (2 H, m, 2×CHCH$_A$H$_B$) and 1.99 (3 H, s, COCH$_3$); m/z (ESI, 15 V) 439 (MH+).

EXAMPLE 36

N-Acetyl-D-thioproline-4[2-(1-phenylethenyl)] phenylalanine from Intermediate 36 and N-acetyl-D-thioproline. δH (DMSO-d$^6$, 400K) (mixture of 2 diastereoisomers) 7.71 (1 H, br, CONH), 7.57–7.21 (9 H, m, ArH), 7.15 (2 H, s,CH=CH), 4.82 (1 H, dd, CHαthiopro), 4.77 and 4.75 (1 H, each d, J 9.2 Hz, NCH$_A$H$_B$S), 4.58 (1 H, m, CHαPh), 4.38 and 4.36 (1 H, each d, J 9.2 Hz, NCH$_A$H$_B$S), 3.29–2.96 (4 H, m, CHCH$_2$Ar+CHCH$_2$S), 1.99 and 1.96 (3H, each s, COCH$_3$); mLz (ESI, 15V) 425 (MH+).

EXAMPLE 37

N-Acetyl-D-thioproline-4-(3-pyridyl)phenylalanine from Intermediate 37 and N-acetyl-D-thioproline. 5 H (DMSO-d$^6$, 400K) 8.82 (1H, d, J 1.8Hz, PyH), 8.53 (1H, dd, J 4.7, 1.5Hz, PyH), 7.96 (1H, ddd, J 8.0, 2.3, 1.8Hz, PyH), 7.53 (2H, d, J 8.2Hz, ArH), 7.5 (1H, br, CONH), 7.41 (1 H, dd, J 7.9, 4.0Hz, PyH), 7.35 (2H, d, J 8.3Hz, ArH), 4.82 (1H, dd, CH(xthiopro), 4.77 (1H, d, J 9.2Hz, NCHAHBS), 4.37 (1H, d, J 9.3Hz, NCHAHBS), 3.27–3.21 (2H, m, 2 x CHCHAHB),3.10–3.04 (2H, m, 2 x CHCHAHB) and 1.97 (3H, s, COCH$_3$); m/z (ESI, 27V) 400 (MH+).

EXAMPLE 38

N-Acetyl-D-thioproline-L-phenylalanine from N-acetyl-Dthioproline and L-phenylalanine methyl ester hydrochloride. 6H (DMSO-d$^6$, 400K) 7.69 (1H, br d, CONH), 7.29–7.17 (5 H, m, ArH), 4.82 (1 H, dd, J 7.4, 3.9 Hz, CHαthiopro), 4.77 (1 H, d, J 9.2 Hz, NCH$_A$H$_B$S), 4.56 (1 H, dt, J 8.3, 5.4 Hz, CHαPh), 4.37 (1 H, d, J 9.3 Hz, NCH$_A$H$_B$S), 3.24 (1 H, dd, J 11.5, 7.4 Hz, CHCH$_A$H$_B$S), 3.15 (1 H, dd, J 14.1, 5.4 Hz, CHCH$_A$H$_B$Ar), 2.99 (1 H, dd, J 11.6, 3.9 Hz, CHCH$_A$H$_B$S), 2.98 (1 H, dd, J 14.1, 8.4 Hz, CHCH$_A$H$_B$Ar) and 1.98 (3 H, COCH$_3$); m/z (ESI, 27 V) 323 (MH+).

EXAMPLE 39

N-Acetyl-D-thioproline-N-methyl-N'-(3,5-dichloro-isonicotinoyl)-L-4-aminophenylalanine from Intermediate 51 and N-acetyl-D-thioproline. δH (DMSO-d$^6$, 420K) 10.39 (1 H, br s, CONH) 8.67 (2 H, s, PyrH), 7.54 (2 H, d, J 7.7 Hz, ArH), 7.25 (2 H, d, J 8.1 Hz, ArH), 5.14 (1 H, dd,CHα), 5.03 (1 H, dd, CHα), 3.35–3.23 (2 H, m, 2×CHCH$_A$H$_B$), 3.05 (1 H, dd, J 14.6, 10.2 Hz, CHCH$_A$H$_B$), 2.93 (3 H, s, NMe), 2.8–2.7 (1 H, br m, CHCH$_A$H$_B$) and 1.91 (3 H, br s, COCH$_3$); m/z (ESI,70 V) 525 (MH+).

EXAMPLE 40

N-Acetyl-D-thioproline-4-(2-hydroxyhexafluoroisopropyl)-DL-phenyl alanine from Intermediate 67 and N-acetyl-D-thioproline δH (DMSO-d$^6$, 390K) 7.90–7.75 (1 H, m, NH), 7.59 (2 H, d, J 7.9 Hz, ArH), 7.35 (2 H, dd, J 8.5, 3.3 Hz, ArH), 4.90–4.80 (1 H, m, NCH$_A$H$_B$S), 4.74 (1 H, dd, J 9.2, 7.3 Hz, NCH$_A$H$_B$S), 4.67–4.55 (1 H, m, α-CH), 4.33 (1 H, dd, J 11.1 and 9.2 Hz, α-CH), 3.29–2.89 (4 H, m, CH$_2$Ar and SCH$_2$CH) and 1.96 (s) and 1.93 (s); together (3 H, COCH$_3$); m/z (ESI, 60 V) 489 (MH+).

EXAMPLE 41

N-Acetyl-D-thioproline-4-(trifluoromethyl)-DL-phenylalanine from 4-(trifluoromethyl)-DL-phenylalanine methyl ester and N-acetyl-D-thioproline δH (DMSO-d$^6$) 8.56–8.12 (1 H, m,NH), 7.68–7.55 (2 H, m, ArH), 7.51–7.37 (2 H, m, ArH),4.85–4.15 (4 H, m, NCH$_2$S and 2×α-CH), 3.40–2.65 (4 H, m,SCH$_2$CH and CH$_2$Ar),2.06 (s) and 2.04 (s) and 1.80(s) and 1.71 (s); together (3 H, COCH$_3$); m/z (ESI, 60 V), 391 (MH+).

EXAMPLE 42

N-Acetyl-D-thioproline-4-(tert-butyl)-DL-phenylalanine from 4-(tert-butyl)-DL-phenlalanine methyl ester and N-acetyl-D-thioproline δH (DMSO-d$^6$) 8.45–8.03 (1 H, m, NH), 7.33–7.07 (4 H, m, ArH), 4.87–4.17 (4 H, m, NCH$_2$S and 2×α-CH), 3.90–2.51 (4 H, m, CH$_2$Ar and SCH$_2$CH), 2.07 (s) and 1.99 (s) and 1.79 (s) and 1.69 (s); together (3 H, COCH$_3$) and 1.25 (9 H, s, $^t$Bu). m/z (ESI, 60 V) 379 (MH+).

EXAMPLE 43

N-Acetyl-D-thioproline-4-{[(2,6-dichlorophenyl)sulphonyl]methyl} phenylalanine from Intermediate 71 and N-acetyl-D-thioproline δH (DMSO-d$^6$) 8.60–8.14 (1 H, m, NH), 7.73–7.61 (2 H, m, ArH), 7.54–7.37 (5 H, m, ArH), 4.87 (2 H,s, CH$_2$SO$_2$), 4.80–4.16 (4 H, m, 2×α-CH and NCH$_2$S), 3.40–2.72 (4 H, m, SCH$_2$CH and CH$_2$Ar), 2.12–1.80 (3 H, m, COCH$_3$) m/z (ESI, 60 V) 545 (MH+).

EXAMPLE 44

N-Acetyl-D-thioproline-4-[(2,6-dichlorobenzyl)-sulphonyl] phenylalanine from Intermediate 72 and N-acetyl-D-thioproline δH (DMSO-d$^6$) 8.46–8.05 (1 H, m, NH), 7.65–7.61 (3 H, m, ArH), 7.20–7.10 (4 H, m, ArH), 4.82–4.61 (4 H, m, SO$_2$CHO and SCH$_2$N), 4.44–4.37 (1 H, m, α-CH), 4.23 (1 H, dd, J 18.7, 9.8 Hz, α-CH), 3.50–2.72 (4 H, m, SCH$_2$CH and CH$_2$Ar) and 2.06 (s) and 2.05 (s) and 1.82 (s) and 1.77 (s) together (3 H, COCH$_3$); m/z (ESI, 60 V) 545 (MH+).

EXAMPLE 45

N-Acetyl-D-thioproline-4-([3,5-dichlorophenyl]carboxamido)phenyl alanine from Intermediate 30 and N-acetyl-D-thioproline. δH (DMSO-d$^6$, 390K) 10.1 (1 H, br s), 7.9–7.8 (4 H,m), 7.76 (1 H, v br s), 7.39 (2 H, m), 7.21 (1 H, t, J 1.9 Hz), 4.82 (1 H, br m), 4.77 (d, J 9.2 Hz) and 4.75 (d, J 9.2 Hz) together (1 H), 4.62 (1 H, br m), 4.37 (1 H, d, J 9.2 Hz), 3.28–3.20 (2 H, br m), 3.12–2.98 (2 H, br m) and 1.99 (s) and 1.67 (s) together (3 H). m/z (ESI, 60 V) 510 (MH+).

EXAMPLE 46

N-Acetyl-D-thioproline (N'-acetyl)-L-4-amino phenylalanine from 4-(N-acetyl)-L—4-amino phenylalanine methylester and N-acetyl-D-thioproline δH (DMSO-d$^6$, 390K) 9.37 (1 H, br s, NH), 7.8–7.62 (1 H, m, NH), 7.44 (2 H, d, J 8.5 Hz, ArH), 7.10 (2 H, d, J 8.5 Hz, ArH), 4.88–4.71 (2 H, m, NCH$_2$S), 4.58–4.45 (1 H, m, α-CH), 4.36 (1 H, d, J 9.2 Hz, α-CH), 3.24 (1 H, dd,J 11.5, 7.4 Hz), 3.07 (1 H, dd, J 14.1, 5.4 Hz), 3.00 (1 H, dd, J 11.5, 3.9 Hz), 2.92 (1 H, dd, J 14.1, 8.4 Hz), and 2.02 (3 H, s, COCH$_3$) and 1.98 (3 H, s, COCH$_3$); m/z (ESI, 60 V), 380 (MH+),

EXAMPLE 47

N-Acetyl-D-thioproline-(N'-2,.6-dimethoxybenzoyl)-L—4-amino phenylalanine from (N-2,6-dimethoxybenzoyl)-L-4-amino-phenylalanine methyl ester and N-acetyl-D-thioproline 5 H (DMSO-d$^6$) 10.10 (1 H, s, NH), 8.44 (d, J 7.9 Hz) and 8.12 (d, J 8.3 Hz); together (1 H,NH), 7.56–7.54 (2 H, m, ArH), 7.33 (1 H, t, J 8.4 Hz, Ar(OMe)$_2$H), 7.20–7.05 (2 H,m, ArH), 6.71 (2 H, d, J 8.4 Hz,Ar(OMe)$_2$H), 4.88–4.20 (4 H, m, NCH$_2$S and 2×α-CH), 3.75 (6 H, S, OMe), 3.40–2.79 (4 H,m, CH$_2$Ar and SCH$_2$CH) and 2.07 (s) and 1.87 (s); together (3 H,COCH$_3$); m/z (ESI, 60 V) 502 (MH+).

EXAMPLE 48

N-Acetyl-D-thioproline (N'-benzoyl)-L-4-amino phenylalanine from (N-benzoyl)-L-4-amino phenylalanine methyl ester and N-acetyl-D-thioproline δH (DMSO-d$^6$,390K) 9.72 (1 H, s,NH), 7.66 (2 H,d,J 8.5 Hz, ArH),7.68–7.49 (6 H, m, ArH and NH), 7.19 (2 H, d, J 8.5 Hz, ArH), 4.85 (1 H, dd, J 7.4, 3.9 Hz, CHα-thiopro), 4.78 (1 H, d, J 9.2 Hz, NCH$_A$H$_B$S), 4.55 (1 H, ddd, J 8.2, 8.2, 5.5 Hz, CHα-Ph), 4.39 (1 H, d, J 9.2 Hz, NCH$_A$H$_B$S),3.27 (1 H, dd, J 11.7, 7.4 Hz, SCH$_A$H$_B$CH), 3.13 (1 H, dd, J 14.1, 5.4 Hz, CH$_A$H$_B$Ar),3.06 (1 H, dd, J 11.5, 3.9 Hz, SCH$_A$H$_B$CH), 2.99 (1 H, dd, J 14.1, 8.2 Hz, CH$_A$H$_B$Ar) and 2.01 (3 H, s, COCH$_3$); m/z (ESI, 60 V) 442 (MH+).

EXAMPLE 49

N-Acetyl-D-thioproline-(N'-2,6-dimethylbenzoyl)-L-4-amino phenylalanine from (N-2,6-dimethylbenzoyl)-L-4-amino-phenylalanine methyl ester and N-acetyl-D-thioproline δH (DMSO-d$^6$) 10.29 (1 H, s, NH),8.44 (d, J 8.0 Hz) and 8.15 (d, J 8.3 Hz) together (1 H, NH), 7.62 (2 H, d, J 6.5 Hz, ArH), 7.29–7.02 (5 H, m, ArH), 4.86–4.18 (4 H, m, NCH$_2$S and 2×α-CH), 3.22–2.71 (4 H, m, SCH$_2$CH and CH$_2$Ar), 2.26 (6 H, s, CH$_3$) and 2.06 (s) and 1.84 (s) together (3 H, COCH$_3$); m/z (ESI, 60 V) 470 (MH+).

EXAMPLE 50

N-Acetyl-D-thioproline-(N'-isonicotinoyl)-L-4-amino-phenylalanine from (N-isonicotinoyl)-L-4-amino phenylalanine methyl ester and N-acetyl-D-thioproline δH (DMSO-d$^6$,390K,) 10.00 (1 H, s, NH), 8.73 (2 H, d, J 6.0 Hz,ArH), 7.83 (2 H, d, J 6.0 Hz, ArH), 7.54 (2 H,d,J 8.5 Hz,ArH), 7.37 (1 H, brs, NH), 7.17 (2 H, d, J 8.5 Hz, ArH), 4.85–4.73 (2 H, m, NCH$_2$S), 4.36 (1 H, d, J 9.3 Hz, α-CH), 4,00 (1 H, br s, α-CH), 3.22 1 H, dd, J 11.3, 7.2 Hz), 3.16–3.05 (2 H,m), 3.10 (1 H, dd, J 13.5,5.2 Hz) and 1.96 (3 H, s,COCH$_3$); m/z (ESI, 60 V) 443 (MH+).

EXAMPLE 51

N-Acetyl-D-thioproline-(N'-tert-butylcarbonyl)-L-4-amino phenylalanine from (N-tert-butylcarbonyl)-L-4-amino phenylalanine methyl ester and N-acetyl-D-thioproline 6 H (DMSO-d$^6$) 9.10 (1 H,s,NH), 8.40 (d, J 8.0 Hz) and 8.10 (d, J 8.2 Hz) together (1 H, NH), 7.52 (2 H, d,J 7.9 Hz, ArH), 7.10 (2 H, app.dd. J 9.3, 8.9 Hz, ArH), 4.85–4.18 (4 H, m, NCH$_2$S and 2×α-CH), 3.29–2.76 (4 H, m, CH$_2$Ar and SCH$_2$CH), 2.06 (s) and 11.5 (s) together (3 H, COCH$_3$) and 1.21 (9 H, s,$^t$Bu); m/z (ESI, 60 V) 422 (MH+).

EXAMPLE 52

N-Acetyl-D-thioproline-(N'-2,6-dichloropheylacetyl)-L-4-amino phenylalanine from (N-2,6-dichlorophenylacetyl)-L-4-amino phenylalanine methyl ester and N-acetyl-D-thioproline δH (DMSO-d$^6$) 10.22 (1 H, s, NH), 8.42 (d, J 8.2 Hz) and 8.12 (d, J 8.4

Hz) together (1 H, NH), 7.55–7.30 (5 H, m, ArH), 7.13 (2 H, dd, J 9.1, 9.1 Hz,ArH), 4.87–4.14 (4 H, m, NCH$_2$S and 2×α-CH), 4.03 (2 H, s,COCH$_2$Ar), 3.45–2.72 (4 H, m,CHCH$_2$Ar and SCH$_2$CH) and 2.05 (s) and 1.84 (s); together (3 H, COCH$_3$); m/z (ESI, 60 V) 524 (MH+).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

α$_4$β$_1$ Integrin-dependent Jurkat cell adhesion to VCAM-1 g 96 well NUNC plates were coated with F(ab)$_2$ fragment goat anti-human IgG Fcδ-specific antibody [Jackson Immuno Research 109-006-098: 100 μl at 2 μg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-1 g diluted in PBS/1% BSA was added and the plates left for 60 minutes at room temperature on a rocking platform. The plates were washed (3× in PBS) and the assay then performed at 37° for 30 min in a total volume of 200 μl containing 2.5×10$^5$ Jurkat cells in the presence or absence of titrated test compounds.

Each plate was washed (2×) with medium and the adherent cells were fixed with 100 μl methanol for 10 minutes followed by another wash. 1 00111 0.25% Rose Bengal (Sigma R4507) in PBS was added for 5 minutes at room temperature and the plates washed (3×) in PBS. 100 μl 50% (v/v) ethanol in PBS was added and the plates left for 60 min after which the absorbance (570 nm) was measured.

α$_4$β$_7$ Integrin-dependent JY cell adhesion to MAdCAM-Ig

This assay was performed in the same manner as the α$_4$β$_1$ assay except that MAdCAM-Ig (150 ng/ml) was used in place of 2d VCAM-1 g and a subline of the β-lympho blastoid cell-line JY was used in place of Jurkat cells. The IC$_{50}$ value for each test compound was determined as described in the α$_4$β$_1$ integrin assay.

α$_5$β$_1$ Integrin-dependent K562 cell adhesion to fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at room temperature on a rocking platform. The blocked plates were washed (3× in PBS) and the assay then performed at 37° C. in a total volume of 200 μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the α$_4$β$_1$ assay above.

α$_m$β$_2$-dependent human polymorphonuclear neutrophils adhesion to plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 μg/ml TMB (Boehringer Mannheim) in 0.1M sodium acetate/citrate buffer, pH 6.0 and absorbance measured at 630 nm.

α$_1$/β$_3$ -dependent human platelet aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (giliter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays the compounds of the invention generally have IC$_{50}$ values in the α$_4$β$_1$ and α$_4$β$_7$ assays of 1 μM and below. The compounds of the Examples typically had IC$_{50}$ values of 500 nM and below in these assays. In the other assays featuring a integrins of other subgroups the same compounds had IC$_{50}$ values of 50 μM and above thus demonstrating the potency and selectivity of their action against α$_4$ integrins.

What is claimed is:

1. A compound of formula (1):

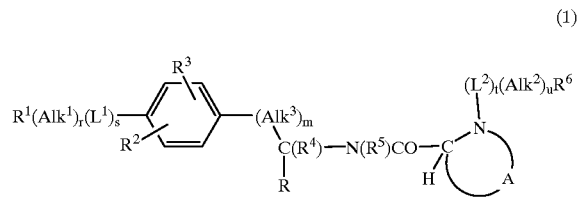

wherein
R$^1$ is a hydrogen atom or an optionally substituted cycloaliphatic, polycycloaliphatic, heterocycloaliphatic, polyheterocycloaliphatic, aromatic or heteroaromatic group;

Alk$^1$ and Alk$^2$, which may be the same or different, is each an optionally substituted aliphatic or heteroaliphatic chain;

L$^1$ is a linker atom or group;

r, s, t and u is each zero or an integer 1;

Alk$^3$ is a straight or branched alkylene chain;

m is zero or an integer 1;

R$^4$ is a hydrogen atom or a methyl group;

R$^5$ is a hydrogen atom or a straight or branched alkyl group;

A is a chain {C(R$^7$)(R$^8$)}$_p$Y{C(R$^9$(R$^{10}$)}$_q$— in which Y is a sulphur atom or a —SO— or —S(O)$_2$— group, R$^7$, $R^8$, $R^9$ an $R^{10}$, which may be the same or different is each a hydrogen atom or a straight or branched alkyl or optionally substituted aromatic group, or $R^7$ and $R^8$, together with the carbon atom to which they are attached, or $R^9$ and $R^{10}$, together with the carbon atom to which they are attached, each forms a $C_{1-7}$cycloalkyl group, and p and q, which may be the same or different is each zero or an integer 1 or 2, provided that when one of p or q is zero the other is an integer 1 or 2;

$L^1$ is a linker group selected from —C(O)—, —C(O)O—, —C(S)—, —S(O)$_2$—, —CON($R^{11}$)—, (where $R^{11}$ is a hydrogen atom or a straight or branched alkyl group), —CSN($R^{11}$)—, —SON($R^{11}$)— or —SO$_2$N($R^{11}$)—;

$R^2$ and $R^3$, which may be the same or different is each an atom or group, —$L^3$(CH$_2$)$_p$L$^4$(R$^{2a}$), in which $L^3$ and $L^4$ is each a covalent bond or a linker atom or group, p is zero or the integer 1, q is an integer 1, 2, or 3 and $R^{2a}$ is a hydrogen or halogen atomn or a group selected from straight or branched alkyl, —OR$^{12}$ (where $R^{12}$ is a hydrogen atom or an optionally substituted straight or branched alkyl group), —SR$^{12}$, NR$^{12}$R$^{13}$ (where $R^{13}$ is as just defined for $R^{12}$ and may be the same or different), —NO$_2$, —CN, CO$_2$R$^{12}$, SO$_3$H, —SO$_2$R$^{12}$, —OCO$_2$R$^{12}$, —CON$^{12}$R$^{13}$, —OCONR$^{12}$R$^{13}$, —CSNR$^{12}$R$^{13}$, —COR$^{12}$, —N(R$^{12}$)COR$^{13}$, —N(R$^{12}$) CSR$^{13}$, —SO$_2$N(R$^{12}$)(R$^{13}$), —N(R$^{12}$)SO$_2$R$^{13}$, —N(R$^{12}$)CON(R$^{13}$)(R$^{14}$), (where $R^{14}$ is a hydrogen atom or an optionally substituted straight or branched alkyl group), —N(R$^{12}$)CSN(R$^{13}$)(R$^{14}$) or —N(R$^{12}$) SO$_2$N(R$^{13}$)(R$^{14}$);

R is a carboxylic acid or a derivative thereof;

$R^6$ is a hydrogen atom or an optionally substituted cycloaliphatic, polycycloaliphatic, heterocycloaliphatic, polyheterocycloaliphatic, aromatic or heteroaromatic group, provided that:

(1) when —R$^1$(Alk$^1$)$_r$(L$^1$)$_s$ is —R$^1$(Alk$^1$)$_r$O—, —R$^1$(Alk$^1$)$_r$C(O)O—, —R$^1$(Alk$^1$)$_r$NHC(O)O— or —R$^1$(Alk$^1$)$_r$S(O)$_2$O—, (in which $R^1$ is a hydrogen atom or an optionally substituted aromatic group and Alk$^1$ is an optionally substituted alkyl group) and R$^6$(Alk$^2$)$_u$(L$^2$)$_t$— is R$^6$(Alk$^2$)$_u$CO—, R$^6$(Alk$^2$)$_u$C(O) O—, R$^6$(Alk$^2$)$_u$NHCO— or R$^6$(Alk$^2$)$_u$S(O)$_2$— (in which Alk$^2$ is an optionally substituted alkyl chain), then $R^6$ is an optionally substituted cycloaliphatic, polycycloaliphatic, heterocycloaliphatic or heteroaromatic group, and (2) Alk$^2$, when present, is not a —(CH$_2$)$_n$S—, —(CH$_2$)$_n$SS— or —(CH$_2$)$_n$SC(O)— chain, where n is an integer 1, 2 or 3;

when A is a sulphur atom, m, p, q, r and s are 1 $R^2$, $R^3$, $R^4$ and $R^5$ are H, and Alk$^3$ is CH, $R^1$ is not H:

and the salts, solvates and hydrates thereof.

2. A compound according to claim 1 in which R is a —CO$_2$H group.

3. A compound according to claim 1 in which Alk$^3$ is a —CH$_2$— chain and m is an integer 1.

4. A compound according to claim 1 in which $R^4$ and $R^5$ is each a hydrogen atom.

5. A compound according to claim 1 in which the chain A is a —C(R$^7$)(R$^8$)SC(R$^9$)(R$^{10}$)— chain.

6. A compound according to claim 1 in which $R^1$ is an optionally substituted aromatic or heteroaromatic group.

7. A compound according to claim 6 in which $R^1$ is an optionally substituted phenyl, pyridyl or pyrimidyl group.

8. A compound according to claim 1 in which t is an integer 1.

9. A compound according to claim 1 in which R$^1$(Alk$^1$)$_r$(L$^1$)$_s$— is a R$^1$CH$_2$L$^1$ or R$^1$L$^1$ group where $R^1$ is an optionally substituted aromatic or heteroaromatic group, Alk$^3$ is a —CH$_2$— chain, m is an integer 1, R is a —CO$_2$H group, $R^4$ and $R^5$ is each a hydrogen atom and —(L$^2$)$_t$(Alk$^2$)$_u$R$^6$ is a —L$^2$CH$_2$R$^6$ group where $R^6$ is a hydrogen atom or an optionally substituted aromatic or heteroaromatic group.

10. A compound according to claim 9 in which R$^1$(Alk$^1$)$_r$(L$^1$)$_s$— is a R$^1$CSN(R$^{11}$)—, R$^1$N(R$^{11}$)—, R$^1$N(R$^{11}$)CO—, R$^1$N(R$^{11}$)CS—, R$^1$S(O)N(R$^{11}$)—, R$^1$S(O)$_2$N(R$^{11}$)—, R$^1$N(R$^{11}$)SO—, R$^1$N(R$^{11}$)S(O)$_2$— or R$^1$CON(R$^{11}$)— group.

11. A compound according to claim 9 wherein R$^1$(Alk$^1$)$_r$(L$^1$)$_s$— is a R$^1$CON(R$^{11}$)— group.

12. A compound according to claim 9 wherein $R^6$ is an optionally substituted heteroaromatic group.

13. A compound according to claim 1 which has the formula (1a):

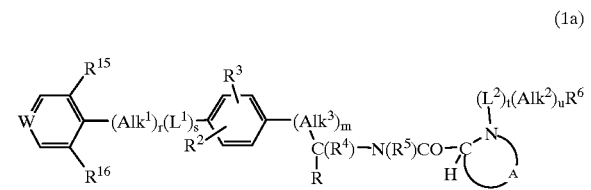

(1a)

wherein:
—W= is —CH= or —N=; and
$R^{15}$ and $R^{16}$, which may be the same or different, is each an atom or group —L$^3$(CH$_2$)$_p$L$^4$(R$^{2a}$)$_q$;
and the salts, solvates, hydrates, and N-oxides thereof.

14. A compound according to claim 13 wherein R is a —CO$_2$H group, Alk$^3$ is a —CH$_2$— chain, m is an integer 1, $R^4$ and $R^5$ is each a hydrogen atom, —(L$^2$)$_t$(Alk$^2$)$_u$R$^6$ is a L$^2$CH$_2$R$^6$ group where $R^6$ is a hydrogen atom or an optionally substituted aromatic or heteroaromatic group and the chain A is a —C(R$^7$)(R$^8$)SC(R$^9$)(R$^{10}$)— chain.

15. A compound according to claim 13 wherein (Alk$^1$)$_r$(L$^1$)$_s$ is a —SO$_2$NH—, —C(O)O—, —NH— or —CONH— group.

16. A compound according to claim 13 wherein each of $R^{15}$ and $R^{16}$ is a substituent —L$^3$(CH$_2$)$_p$L$^4$(R$^{2a}$)$_q$ in which $R^{2a}$ is not a hydrogen atom when $L^3$ and $L^4$ is each a covalent bond and p is zero.

17. A compound which is:
N-(Pyrid-3-ylacetyl)-D-thioproline-(N'-2,6-dichlorobenzoyl)-L-4-aminophenylalanine;
N-Acetyl-D-thioproline-(N'-3,5-dichloroisonicotinoyl)-L-4-amino phenylalanine;
N-(Pyrid-3-ylacetyl)-D-thioproline-O-(2,4,6-trichlorobenzyl)-L-tyrosine;
N-(Pyrid-3-ylacetyl)-D-thioproline-(O-2,4,6-trichlorobenzoyl)-L-tyrosine;
N-(Pyrid-3-ylacetyl)-D-thioproline-(O-2,6-dichlorobenzoyl)-L-tyrosine;
N-Acetyl-D-thioproline-(N'-2,6-dichlorobenzoyl)-L-4-aminophenylalanine;
N-Acetyl-D-thioproline-[N'-2-fluoro-6-(trifluoromethyl)benzoyl]-L-4-aminophenylalanine;
N-Acetyl-D-thioproline-(N'-2,4,6-trichlorobenzoyl)-L-4-aminophenylalanine;
N-Acetyl-D-thioproline-(N'-2,6-trichlorobenzyl)-L-4-aminophenylalanine; and the salts, solvates, hydrates and N-oxides thereof.

18. A pharmaceutical composition comprising a compound according to claim 1 together with one or more pharmaceutically acceptable carriers, excipients or diluents.

19. A method for the prophylaxis or treatment of a disease or disorder in a mammal in which the extravasation of leukocytes plays a role, comprising administering to a mammal suffering from such a disease or disorder a therapeutically effective amount of a compound according to claim 1.

20. A method according to claim 19 wherein said disease or disorder is selected from the group consisting of inflammatory arthritis, multiple sclerosis, allograft rejection, diabetes, inflammatory dermatoses, asthma and inflammatory bowel disease.

21. A method according to claim 20 wherein said inflammatory arthritis is selected from the group consisting of rheumatoid arthritis vasculitis and polydermatomyositis.

22. A method according to claim 21 wherein said inflammatory dermatoses are selected from the group consisting of psoriasis and dermatitis.

23. A method for inhibiting, in a mammal, the binding of U4 integrins to the ligands thereof, comprising administering to the mammal an effective amount of a compound according to claim 1.

24. A method according to claim 23 wherein the a4 integrins are selected from the group consisting of $\alpha_4\beta_1$ and $\alpha_4\beta_7$ integrins.

* * * * *

UNITED STATES PATENT AND TRADEMARK OFFICE
CERTIFICATE OF CORRECTION

PATENT NO. : 6,197,794 B1
DATED : March 6, 2001
INVENTOR(S) : John Clifford Head et al.

It is certified that error appears in the above-identified patent and that said Letters Patent is hereby corrected as shown below:

Column 2,
Line 41, change "ax" to -- α4 --.

Column 13,
Line 51, change "suit able" to -- suitable --.

Column 17,
Line 62, change "D4hioproline" to -- D-thioproline --.

Column 19,
Line 35, change "5H" to -- δH --.

Column 21,
Line 6, change "AH" to -- δH --.
Line 54, change "8H" to -- δH --.

Column 22,
Line 7, change "5H" to -- δH --.

Column 23,
Line 5, change "AH" to -- δH --.
Line 24, change "6H" to -- δH --.

Column 24,
Line 34, change "AH" to -- δH --.

Column 25,
Line 4, change "chromaography" to -- chromatography --.
Line 63, change "900" to -- 90° --.

Column 30,
Line 62, change "5H" to -- δH --.

Column 33,
Line 10, "At" is not in the application.

Column 34,
Line 53, change "6H" to -- δH --.

UNITED STATES PATENT AND TRADEMARK OFFICE
CERTIFICATE OF CORRECTION

PATENT NO. : 6,197,794 B1
DATED : March 6, 2001
INVENTOR(S) : John Clifford Head et al.

It is certified that error appears in the above-identified patent and that said Letters Patent is hereby corrected as shown below:

Column 38,
Line 49, change "NIH" to -- N$\underline{H}$ --;
Line 49, change "NiH" to -- N$\underline{H}$ --.

Column 41,
Line 41, after "ddd" change the "1" to -- $\underline{J}$ --.

Column 43,
Line 46, change "8H" to -- δH --.

Column 46,
Line 66, change "5H" to -- δH --.

Column 50,
Line 6, change "Mlz" to -- m/z --.
Line 10, change "5H" to -- δH --.
Line 15, change "CH (xathipro)" to -- CHαthiopro) --.
Lines 15 and 16, change "NCHAHBS" to -- NCH$_A$H$_B$S --.
Line 17, change "CHCHAHB" to -- CHCH$_A$H$_B$ --;
Line 17, change "CHCHAHB" to -- CHCH$_A$H$_B$ --.
Line 22, change "6H" to -- δH --.
Line 24, change "Chanthiopro" to -- Chαthiopro --.

Column 51,
Line 2, "thloproline" should be -- thioproline --.
Line 64, "5 H" should be -- δH --.

Column 53,
Line 18, change "Fcδ - specific" to -- Fcγ-specific --.
Line 33, change "1 00111" to -- 100γL --.

Column 54,
Line 24, "(giliter:" should be -- g/liter --.
Line 34, "a" should be -- α --.

Column 55,
Line 6, "$C_{1-7}$" should be -- $C_{3-7}$ --.
Line 18, change "atomn" to -- atom --.
Line 24, change "CON$^{12}$R$^{13}$" to -- CONR$^{12}$R$^{13}$ --.

UNITED STATES PATENT AND TRADEMARK OFFICE
CERTIFICATE OF CORRECTION

PATENT NO.   : 6,197,794 B1
DATED        : March 6, 2001
INVENTOR(S)  : John Clifford Head et al.

It is certified that error appears in the above-identified patent and that said Letters Patent is hereby corrected as shown below:

Column 58,
Line 8, change "U4" to -- α4 --.
Line 10, change "a4" to -- a4 --.

Signed and Sealed this

Sixteenth Day of April, 2002

Attest:

JAMES E. ROGAN
*Director of the United States Patent and Trademark Office*

*Attesting Officer*